United States Patent
Vandike et al.

(10) Patent No.: US 11,849,671 B2
(45) Date of Patent: *Dec. 26, 2023

(54) CROP STATE MAP GENERATION AND CONTROL SYSTEM

(71) Applicant: Deere & Company, Moline, IL (US)

(72) Inventors: Nathan R. Vandike, Geneseo, IL (US); Bhanu Kiran Reddy Palla, Bettendorf, IA (US); Noel W. Anderson, Fargo, ND (US); Federico Pardina-Malbran, Fort Collins, CO (US)

(73) Assignee: Deere & Company, Moline, IL (US)

( * ) Notice: Subject to any disclaimer, the term of this patent is extended or adjusted under 35 U.S.C. 154(b) by 433 days.

This patent is subject to a terminal disclaimer.

(21) Appl. No.: 17/067,025

(22) Filed: Oct. 9, 2020

(65) Prior Publication Data
US 2022/0110247 A1   Apr. 14, 2022

(51) Int. Cl.
*A01B 79/00*   (2006.01)
*A01D 41/127*   (2006.01)
(Continued)

(52) U.S. Cl.
CPC ........ *A01D 41/127* (2013.01); *G01B 11/0608* (2013.01); *G01N 33/0098* (2013.01);
(Continued)

(58) Field of Classification Search
CPC ........... G05D 1/02; G01C 21/32; A01B 79/00
See application file for complete search history.

(56) References Cited

U.S. PATENT DOCUMENTS

| 3,568,157 A | 3/1971 | Downing et al. |
| 3,580,257 A | 5/1971 | Teague |

(Continued)

FOREIGN PATENT DOCUMENTS

| AR | 108898 A1 | 10/2018 |
| AU | 20100224431 A1 | 4/2011 |

(Continued)

OTHER PUBLICATIONS

Prosecution History for U.S. Appl. No. 16/380,691 including: Notice of Allowance dated Mar. 10, 2021 and Application and Drawings filed Apr. 10, 2019, 46 pages.
(Continued)

*Primary Examiner* — Tan Q Nguyen
(74) *Attorney, Agent, or Firm* — Joseph R. Kelly; Kelly, Holt & Christenson PLLC

(57) ABSTRACT

One or more information maps are obtained by an agricultural work machine. The one or more information maps map one or more agricultural characteristic values at different geographic locations of a field. An in-situ sensor on the agricultural work machine senses an agricultural characteristic as the agricultural work machine moves through the field. A predictive map generator generates a predictive map that predicts a predictive agricultural characteristic at different locations in the field based on a relationship between the values in the one or more information maps and the agricultural characteristic sensed by the in-situ sensor. The predictive map can be output and used in automated machine control.

20 Claims, 11 Drawing Sheets

(51) Int. Cl.
  *G01B 11/06* (2006.01)
  *G01S 19/01* (2010.01)
  *G06N 20/00* (2019.01)
  *G01N 33/00* (2006.01)
  *G05D 1/02* (2020.01)
  *A01D 41/14* (2006.01)

(52) U.S. Cl.
  CPC .............. *G01S 19/01* (2013.01); *G06N 20/00* (2019.01); *A01D 41/1278* (2013.01); *A01D 41/141* (2013.01)

(56) References Cited

U.S. PATENT DOCUMENTS

| | | | |
|---|---|---|---|
| 3,599,543 | A | 8/1971 | Kerridge |
| 3,775,019 | A | 11/1973 | Konig et al. |
| 3,856,754 | A | 12/1974 | Habermeier et al. |
| 4,129,573 | A | 12/1978 | Bellus et al. |
| 4,166,735 | A | 9/1979 | Pilgram et al. |
| 4,183,742 | A | 1/1980 | Sasse et al. |
| 4,268,679 | A | 5/1981 | Lavanish |
| 4,349,377 | A | 9/1982 | Dürr et al. |
| 4,360,677 | A | 11/1982 | Doweyko et al. |
| 4,435,203 | A | 3/1984 | Funaki et al. |
| 4,493,726 | A | 1/1985 | Burdeska et al. |
| 4,527,241 | A | 7/1985 | Sheehan et al. |
| 4,566,901 | A | 1/1986 | Martin et al. |
| 4,584,013 | A | 4/1986 | Brunner |
| 4,687,505 | A | 8/1987 | Sylling et al. |
| 4,857,101 | A | 8/1989 | Musco et al. |
| 4,911,751 | A | 3/1990 | Nyffeler et al. |
| 5,059,154 | A | 10/1991 | Reyenga |
| 5,089,043 | A | 2/1992 | Hayase et al. |
| 5,246,164 | A | 9/1993 | McCann et al. |
| 5,246,915 | A | 9/1993 | Lutz et al. |
| 5,250,690 | A | 10/1993 | Turner et al. |
| 5,296,702 | A | 3/1994 | Beck et al. |
| 5,300,477 | A | 4/1994 | Tice |
| 5,416,061 | A | 5/1995 | Hewett et al. |
| 5,477,459 | A | 12/1995 | Clegg et al. |
| 5,488,817 | A | 2/1996 | Paquet et al. |
| 5,563,112 | A | 10/1996 | Barnes III |
| 5,585,626 | A | 12/1996 | Beck et al. |
| 5,586,033 | A | 12/1996 | Hall |
| 5,592,606 | A | 1/1997 | Myers |
| 5,606,821 | A | 3/1997 | Sadjadi et al. |
| 5,666,793 | A | 9/1997 | Bottinger |
| 5,712,782 | A | 1/1998 | Weigelt et al. |
| 5,721,679 | A | 2/1998 | Monson |
| 5,767,373 | A | 6/1998 | Ward et al. |
| 5,771,169 | A | 6/1998 | Wendte |
| 5,789,741 | A | 8/1998 | Kinter et al. |
| 5,809,440 | A | 9/1998 | Beck et al. |
| 5,841,282 | A | 11/1998 | Christy et al. |
| 5,849,665 | A | 12/1998 | Gut et al. |
| 5,878,821 | A | 3/1999 | Flenker et al. |
| 5,899,950 | A | 5/1999 | Milender et al. |
| 5,902,343 | A | 5/1999 | Hale et al. |
| 5,915,492 | A | 6/1999 | Yates et al. |
| 5,957,304 | A | 9/1999 | Dawson |
| 5,974,348 | A | 10/1999 | Rocks |
| 5,978,723 | A | 11/1999 | Hale et al. |
| 5,991,687 | A | 11/1999 | Hale et al. |
| 5,991,694 | A | 11/1999 | Gudat et al. |
| 5,995,859 | A | 11/1999 | Takahashi |
| 5,995,894 | A | 11/1999 | Wendte |
| 5,995,895 | A * | 11/1999 | Watt .................. B60K 31/0066 56/10.2 G |
| 6,004,076 | A | 12/1999 | Cook et al. |
| 6,016,713 | A | 1/2000 | Hale |
| 6,029,106 | A | 2/2000 | Hale et al. |
| 6,041,582 | A | 3/2000 | Tiede et al. |
| 6,073,070 | A | 6/2000 | Diekhans |
| 6,073,428 | A | 6/2000 | Diekhans |
| 6,085,135 | A | 7/2000 | Steckel |
| 6,119,442 | A | 9/2000 | Hale |
| 6,119,531 | A | 9/2000 | Wendte et al. |
| 6,128,574 | A | 10/2000 | Diekhans |
| 6,141,614 | A | 10/2000 | Janzen et al. |
| 6,178,253 | B1 | 1/2001 | Hendrickson et al. |
| 6,185,990 | B1 | 2/2001 | Missotten et al. |
| 6,188,942 | B1 | 2/2001 | Corcoran et al. |
| 6,199,000 | B1 | 3/2001 | Keller et al. |
| 6,204,856 | B1 | 3/2001 | Wood et al. |
| 6,205,381 | B1 | 3/2001 | Motz et al. |
| 6,205,384 | B1 | 3/2001 | Diekhans |
| 6,216,071 | B1 | 4/2001 | Motz |
| 6,236,924 | B1 | 5/2001 | Motz et al. |
| 6,266,595 | B1 * | 7/2001 | Greatline ............... G01C 21/00 701/50 |
| 6,272,819 | B1 | 8/2001 | Wendte et al. |
| 6,327,569 | B1 | 12/2001 | Reep |
| 6,374,173 | B1 | 4/2002 | Ehlbeck |
| 6,380,745 | B1 | 4/2002 | Anderson et al. |
| 6,431,790 | B1 | 8/2002 | Anderegg et al. |
| 6,451,733 | B1 | 9/2002 | Pidskalny et al. |
| 6,505,146 | B1 | 1/2003 | Blackmer |
| 6,505,998 | B1 | 1/2003 | Bullivant |
| 6,539,102 | B1 | 3/2003 | Anderson et al. |
| 6,549,849 | B2 | 4/2003 | Lange et al. |
| 6,584,390 | B2 | 6/2003 | Beck |
| 6,591,145 | B1 | 7/2003 | Hoskinson et al. |
| 6,591,591 | B2 | 7/2003 | Coers et al. |
| 6,592,453 | B2 | 7/2003 | Coers et al. |
| 6,604,432 | B1 | 8/2003 | Hamblen et al. |
| 6,681,551 | B1 | 1/2004 | Sheidler et al. |
| 6,682,416 | B2 | 1/2004 | Behnke et al. |
| 6,687,616 | B1 | 2/2004 | Peterson et al. |
| 6,729,189 | B2 | 5/2004 | Paakkinen |
| 6,735,568 | B1 | 5/2004 | Buckwalter et al. |
| 6,834,550 | B2 | 12/2004 | Upadhyaya et al. |
| 6,838,564 | B2 | 1/2005 | Edmunds et al. |
| 6,846,128 | B2 | 1/2005 | Sick |
| 6,932,554 | B2 | 8/2005 | Isfort et al. |
| 6,999,877 | B1 | 2/2006 | Dyer et al. |
| 7,073,374 | B2 | 7/2006 | Berkman |
| 7,167,797 | B2 | 1/2007 | Faivre et al. |
| 7,167,800 | B2 | 1/2007 | Faivre et al. |
| 7,191,062 | B2 | 3/2007 | Chi et al. |
| 7,194,965 | B2 | 3/2007 | Hickey et al. |
| 7,211,994 | B1 | 5/2007 | Mergen et al. |
| 7,248,968 | B2 | 7/2007 | Reid |
| 7,255,016 | B2 | 8/2007 | Burton |
| 7,261,632 | B2 | 8/2007 | Pirro et al. |
| 7,302,837 | B2 | 12/2007 | Wendte |
| 7,308,326 | B2 | 12/2007 | Maertens et al. |
| 7,313,478 | B1 | 12/2007 | Anderson et al. |
| 7,318,010 | B2 | 1/2008 | Anderson |
| 7,347,168 | B2 | 3/2008 | Reckels et al. |
| 7,408,145 | B2 | 8/2008 | Holland |
| 7,480,564 | B2 | 1/2009 | Metzler et al. |
| 7,483,791 | B2 | 1/2009 | Anderegg et al. |
| 7,537,519 | B2 | 5/2009 | Huster et al. |
| 7,557,066 | B2 | 7/2009 | Hills et al. |
| 7,628,059 | B1 | 12/2009 | Scherbring |
| 7,687,435 | B2 | 3/2010 | Witschel et al. |
| 7,703,036 | B2 | 4/2010 | Satterfield et al. |
| 7,725,233 | B2 | 5/2010 | Hendrickson et al. |
| 7,733,416 | B2 | 6/2010 | Gal |
| 7,756,624 | B2 | 7/2010 | Diekhans et al. |
| 7,798,894 | B2 | 9/2010 | Isfort |
| 7,827,042 | B2 | 11/2010 | Jung et al. |
| 7,915,200 | B2 | 3/2011 | Epp et al. |
| 7,945,364 | B2 | 5/2011 | Schricker et al. |
| 7,993,188 | B2 | 8/2011 | Ritter |
| 8,024,074 | B2 | 9/2011 | Stelford et al. |
| 8,060,283 | B2 | 11/2011 | Mott et al. |
| 8,107,681 | B2 | 1/2012 | Gaal |
| 8,145,393 | B2 | 3/2012 | Foster et al. |
| 8,147,176 | B2 | 4/2012 | Coers et al. |
| 8,152,610 | B2 | 4/2012 | Harrington |
| 8,190,335 | B2 | 5/2012 | Vik et al. |
| 8,195,342 | B2 | 6/2012 | Anderson |
| 8,195,358 | B2 | 6/2012 | Anderson |

(56) References Cited

U.S. PATENT DOCUMENTS

| | | |
|---|---|---|
| 8,213,964 B2 | 7/2012 | Fitzner et al. |
| 8,224,500 B2 | 7/2012 | Anderson |
| 8,252,723 B2 | 8/2012 | Jakobi et al. |
| 8,254,351 B2 | 8/2012 | Fitzner et al. |
| 8,321,365 B2 | 11/2012 | Anderson |
| 8,329,717 B2 | 12/2012 | Minn et al. |
| 8,332,105 B2 | 12/2012 | Laux |
| 8,338,332 B1 | 12/2012 | Hacker et al. |
| 8,340,862 B2 | 12/2012 | Baumgarten et al. |
| 8,407,157 B2 | 3/2013 | Anderson |
| 8,428,829 B2 | 4/2013 | Brunnert et al. |
| 8,478,493 B2 | 7/2013 | Anderson |
| 8,488,865 B2 | 7/2013 | Hausmann et al. |
| 8,494,727 B2 | 7/2013 | Green et al. |
| 8,527,157 B2 | 9/2013 | Imhof et al. |
| 8,544,397 B2 | 10/2013 | Bassett |
| 8,577,561 B2 | 11/2013 | Green et al. |
| 8,606,454 B2 | 12/2013 | Wang et al. |
| 8,626,406 B2 | 1/2014 | Schleicher et al. |
| 8,635,903 B2 | 1/2014 | Oetken et al. |
| 8,649,940 B2 | 2/2014 | Bonefas |
| 8,656,693 B2 | 2/2014 | Madsen et al. |
| 8,662,972 B2 | 3/2014 | Behnke et al. |
| 8,671,760 B2 | 3/2014 | Wallrath et al. |
| 8,677,724 B2 | 3/2014 | Chaney et al. |
| 8,738,238 B2 | 5/2014 | Rekow |
| 8,738,244 B2 | 5/2014 | Lenz |
| 8,755,976 B2 | 6/2014 | Peters et al. |
| 8,781,692 B2 | 7/2014 | Kormann |
| 8,789,563 B2 | 7/2014 | Wenzel |
| 8,814,640 B2 | 8/2014 | Behnke et al. |
| 8,843,269 B2 | 9/2014 | Anderson et al. |
| 8,849,523 B1 * | 9/2014 | Chan .................. A01G 25/167 |
| | | 701/50 |
| 8,868,304 B2 | 10/2014 | Bonefas |
| 8,909,389 B2 | 12/2014 | Meyer |
| 8,942,860 B2 | 1/2015 | Morselli |
| 8,962,523 B2 | 2/2015 | Rosinger et al. |
| 9,002,591 B2 | 4/2015 | Wang et al. |
| 9,008,918 B2 | 4/2015 | Missotten et al. |
| 9,009,087 B1 | 4/2015 | Mewes et al. |
| 9,011,222 B2 | 4/2015 | Johnson et al. |
| 9,014,901 B2 | 4/2015 | Wang et al. |
| 9,043,096 B2 | 5/2015 | Zielke et al. |
| 9,043,129 B2 | 5/2015 | Bonefas et al. |
| 9,066,465 B2 | 6/2015 | Hendrickson et al. |
| 9,072,227 B2 | 7/2015 | Wenzel |
| 9,095,090 B2 | 8/2015 | Casper et al. |
| 9,119,342 B2 | 9/2015 | Bonefas |
| 9,127,428 B2 | 9/2015 | Meier |
| 9,131,644 B2 | 9/2015 | Osborne |
| 9,152,938 B2 | 10/2015 | Lang et al. |
| 9,173,339 B2 | 11/2015 | Sauder et al. |
| 9,179,589 B2 | 11/2015 | Bischoff |
| 9,188,518 B2 | 11/2015 | Snyder et al. |
| 9,188,986 B2 | 11/2015 | Baumann |
| 9,226,449 B2 | 1/2016 | Bischoff |
| 9,234,317 B2 | 1/2016 | Chi |
| 9,235,214 B2 | 1/2016 | Anderson |
| 9,301,447 B2 | 4/2016 | Kormann |
| 9,301,466 B2 | 4/2016 | Kelly |
| 9,313,951 B2 | 4/2016 | Herman et al. |
| 9,326,443 B2 | 5/2016 | Zametzer et al. |
| 9,326,444 B2 | 5/2016 | Bonefas |
| 9,392,746 B2 | 7/2016 | Darr et al. |
| 9,405,039 B2 | 8/2016 | Anderson |
| 9,410,840 B2 | 8/2016 | Acheson et al. |
| 9,439,342 B2 | 9/2016 | Pasquier |
| 9,457,971 B2 | 10/2016 | Bonefas et al. |
| 9,463,939 B2 | 10/2016 | Bonefas et al. |
| 9,485,905 B2 | 11/2016 | Jung et al. |
| 9,489,576 B2 | 11/2016 | Johnson et al. |
| 9,497,898 B2 | 11/2016 | Dillon |
| 9,510,508 B2 | 12/2016 | Jung |
| 9,511,633 B2 | 12/2016 | Anderson et al. |
| 9,511,958 B2 | 12/2016 | Bonefas |
| 9,516,812 B2 | 12/2016 | Baumgarten et al. |
| 9,521,805 B2 | 12/2016 | Muench et al. |
| 9,522,791 B2 | 12/2016 | Bonefas et al. |
| 9,522,792 B2 | 12/2016 | Bonefas et al. |
| 9,523,180 B2 | 12/2016 | Deines |
| 9,529,364 B2 | 12/2016 | Foster et al. |
| 9,532,504 B2 | 1/2017 | Herman et al. |
| 9,538,714 B2 | 1/2017 | Anderson |
| 9,563,492 B2 | 2/2017 | Bell et al. |
| 9,563,848 B1 | 2/2017 | Hunt |
| 9,563,852 B1 | 2/2017 | Wiles et al. |
| 9,578,808 B2 | 2/2017 | Dybro et al. |
| 9,629,308 B2 | 4/2017 | SchøLer et al. |
| 9,631,964 B2 | 4/2017 | Gelinske et al. |
| 9,642,305 B2 | 5/2017 | Nykamp et al. |
| 9,648,807 B2 | 5/2017 | Escher et al. |
| 9,675,008 B1 | 6/2017 | Rusciolelli et al. |
| 9,681,605 B2 | 6/2017 | Noonan et al. |
| 9,694,712 B2 | 7/2017 | Healy |
| 9,696,162 B2 | 7/2017 | Anderson |
| 9,699,967 B2 | 7/2017 | Palla et al. |
| 9,714,856 B2 | 7/2017 | Myers |
| 9,717,178 B1 | 8/2017 | Sauder et al. |
| 9,721,181 B2 | 8/2017 | Guan et al. |
| 9,723,790 B2 | 8/2017 | Berry et al. |
| 9,740,208 B2 | 8/2017 | Sugumaran et al. |
| 9,767,521 B2 | 9/2017 | Stuber et al. |
| 9,807,934 B2 | 11/2017 | Rusciolelli et al. |
| 9,807,940 B2 | 11/2017 | Roell et al. |
| 9,810,679 B2 | 11/2017 | Kimmel |
| 9,829,364 B2 | 11/2017 | Wilson et al. |
| 9,848,528 B2 | 12/2017 | Werner et al. |
| 9,856,609 B2 | 1/2018 | Dehmel |
| 9,856,612 B2 | 1/2018 | Oetken |
| 9,861,040 B2 | 1/2018 | Bonefas |
| 9,872,433 B2 | 1/2018 | Acheson et al. |
| 9,903,077 B2 | 2/2018 | Rio |
| 9,903,979 B2 | 2/2018 | Dybro et al. |
| 9,904,963 B2 | 2/2018 | Rupp et al. |
| 9,915,952 B2 | 3/2018 | Dollinger et al. |
| 9,922,405 B2 | 3/2018 | Sauder et al. |
| 9,924,636 B2 | 3/2018 | Lisouski et al. |
| 9,928,584 B2 | 3/2018 | Jens et al. |
| 9,933,787 B2 | 4/2018 | Story |
| 9,974,226 B2 | 5/2018 | Rupp et al. |
| 9,982,397 B2 | 5/2018 | Korb et al. |
| 9,984,455 B1 | 5/2018 | Fox et al. |
| 9,992,931 B2 | 6/2018 | Bonefas et al. |
| 9,992,932 B2 | 6/2018 | Bonefas et al. |
| 10,004,176 B2 | 6/2018 | Mayerle |
| 10,015,928 B2 | 7/2018 | Nykamp et al. |
| 10,019,018 B2 | 7/2018 | Hulin |
| 10,019,790 B2 | 7/2018 | Bonefas et al. |
| 10,025,983 B2 | 7/2018 | Guan et al. |
| 10,028,435 B2 | 7/2018 | Anderson et al. |
| 10,028,451 B2 | 7/2018 | Rowan et al. |
| 10,034,427 B2 | 7/2018 | Krause et al. |
| 10,039,231 B2 | 8/2018 | Anderson et al. |
| 10,064,331 B2 | 9/2018 | Bradley |
| 10,064,335 B2 | 9/2018 | Byttebier et al. |
| 10,078,890 B1 | 9/2018 | Tagestad et al. |
| 10,085,372 B2 | 10/2018 | Noyer et al. |
| 10,091,925 B2 | 10/2018 | Aharoni et al. |
| 10,126,153 B2 | 11/2018 | Bischoff et al. |
| 10,129,528 B2 | 11/2018 | Bonefas et al. |
| 10,143,132 B2 | 12/2018 | Inoue et al. |
| 10,152,035 B2 | 12/2018 | Reid et al. |
| 10,154,624 B2 | 12/2018 | Guan et al. |
| 10,165,725 B2 | 1/2019 | Sugumaran et al. |
| 10,178,823 B2 | 1/2019 | Kovach et al. |
| 10,183,667 B2 | 1/2019 | Anderson et al. |
| 10,188,037 B2 | 1/2019 | Bruns et al. |
| 10,201,121 B1 | 2/2019 | Wilson |
| 10,209,179 B2 | 2/2019 | Hollstein |
| 10,231,371 B2 | 3/2019 | Dillon |
| 10,254,147 B2 | 4/2019 | Vermue et al. |
| 10,254,765 B2 | 4/2019 | Rekow |
| 10,255,670 B1 | 4/2019 | Wu et al. |

(56) References Cited

U.S. PATENT DOCUMENTS

| | | |
|---|---|---|
| 10,275,550 B2 | 4/2019 | Lee |
| 10,295,703 B2 | 5/2019 | Dybro et al. |
| 10,310,455 B2 | 6/2019 | Blank et al. |
| 10,314,232 B2 | 6/2019 | Isaac et al. |
| 10,315,655 B2 | 6/2019 | Blank et al. |
| 10,317,272 B2 | 6/2019 | Bhavsar et al. |
| 10,351,364 B2 | 7/2019 | Green et al. |
| 10,368,488 B2 | 8/2019 | Becker et al. |
| 10,398,084 B2 | 9/2019 | Ray et al. |
| 10,408,545 B2 | 9/2019 | Blank et al. |
| 10,412,889 B2 | 9/2019 | Palla et al. |
| 10,426,086 B2 | 10/2019 | Van de Wege et al. |
| 10,437,243 B2 | 10/2019 | Blank et al. |
| 10,477,756 B1 | 11/2019 | Richt et al. |
| 10,485,178 B2 | 11/2019 | Mayerle |
| 10,521,526 B2 | 12/2019 | Haaland et al. |
| 10,537,061 B2 | 1/2020 | Farley et al. |
| 10,568,316 B2 | 2/2020 | Gall et al. |
| 10,631,462 B2 | 4/2020 | Bonefas |
| 10,677,637 B1 | 6/2020 | Von Muenster |
| 10,681,872 B2 | 6/2020 | Viaene et al. |
| 10,703,277 B1 | 7/2020 | Schroeder |
| 10,729,067 B2 | 8/2020 | Hammer et al. |
| 10,740,703 B2 | 8/2020 | Story |
| 10,745,868 B2 | 8/2020 | Laugwitz et al. |
| 10,760,946 B2 | 9/2020 | Meier et al. |
| 10,809,118 B1 | 10/2020 | Von Muenster |
| 10,830,634 B2 | 11/2020 | Blank et al. |
| 10,866,109 B2 | 12/2020 | Madsen et al. |
| 10,890,922 B2 | 1/2021 | Ramm et al. |
| 10,909,368 B2 | 2/2021 | Guo et al. |
| 10,912,249 B1 | 2/2021 | Wilson |
| 2002/0011061 A1 | 1/2002 | Lucand et al. |
| 2002/0083695 A1 | 7/2002 | Behnke et al. |
| 2002/0091458 A1 | 7/2002 | Moore |
| 2002/0099471 A1 | 7/2002 | Benneweis |
| 2002/0133309 A1 | 9/2002 | Hardt |
| 2002/0173893 A1 | 11/2002 | Blackmore et al. |
| 2002/0193928 A1 | 12/2002 | Beck |
| 2002/0193929 A1 | 12/2002 | Beck |
| 2002/0198654 A1 | 12/2002 | Lange et al. |
| 2003/0004630 A1 | 1/2003 | Beck |
| 2003/0014171 A1 | 1/2003 | Ma et al. |
| 2003/0015351 A1 | 1/2003 | Goldman et al. |
| 2003/0024450 A1 | 2/2003 | Juptner |
| 2003/0060245 A1 | 3/2003 | Coers et al. |
| 2003/0069680 A1 | 4/2003 | Cohen et al. |
| 2003/0075145 A1 | 4/2003 | Sheidler et al. |
| 2003/0174207 A1 | 9/2003 | Alexia et al. |
| 2003/0182144 A1 | 9/2003 | Pickett et al. |
| 2003/0187560 A1 | 10/2003 | Keller et al. |
| 2003/0216158 A1 | 11/2003 | Bischoff |
| 2003/0229432 A1 | 12/2003 | Ho et al. |
| 2003/0229433 A1 | 12/2003 | van den Berg et al. |
| 2003/0229435 A1 | 12/2003 | Van der Lely |
| 2004/0004544 A1 | 1/2004 | William Knutson |
| 2004/0054457 A1 | 3/2004 | Kormann |
| 2004/0073468 A1 | 4/2004 | Vyas et al. |
| 2004/0193348 A1 | 9/2004 | Gray et al. |
| 2005/0059445 A1 | 3/2005 | Niermann et al. |
| 2005/0066738 A1 | 3/2005 | Moore |
| 2005/0149235 A1 | 7/2005 | Seal et al. |
| 2005/0150202 A1 | 7/2005 | Quick |
| 2005/0197175 A1 | 9/2005 | Anderson |
| 2005/0241285 A1 | 11/2005 | Maertens et al. |
| 2005/0283314 A1 | 12/2005 | Hall |
| 2005/0284119 A1 | 12/2005 | Brunnert |
| 2006/0014489 A1 | 1/2006 | Fitzner et al. |
| 2006/0014643 A1 | 1/2006 | Hacker et al. |
| 2006/0047377 A1 | 3/2006 | Ferguson et al. |
| 2006/0058896 A1 | 3/2006 | Pokorny et al. |
| 2006/0074560 A1 | 4/2006 | Dyer et al. |
| 2006/0155449 A1 | 7/2006 | Dammann |
| 2006/0162631 A1 | 7/2006 | Hickey et al. |
| 2006/0196158 A1 | 9/2006 | Faivre et al. |
| 2006/0200334 A1 | 9/2006 | Faivre et al. |
| 2007/0005209 A1 | 1/2007 | Fitzner et al. |
| 2007/0021948 A1 | 1/2007 | Anderson |
| 2007/0056258 A1 | 3/2007 | Behnke |
| 2007/0068238 A1 | 3/2007 | Wendte |
| 2007/0073700 A1 | 3/2007 | Wippersteg et al. |
| 2007/0089390 A1 | 4/2007 | Hendrickson et al. |
| 2007/0135190 A1 | 6/2007 | Diekhans et al. |
| 2007/0185749 A1 | 8/2007 | Anderson et al. |
| 2007/0199903 A1 | 8/2007 | Denny |
| 2007/0208510 A1 | 9/2007 | Anderson et al. |
| 2007/0233348 A1 | 10/2007 | Diekhans et al. |
| 2007/0233374 A1 | 10/2007 | Diekhans et al. |
| 2007/0239337 A1 | 10/2007 | Anderson |
| 2007/0282523 A1 | 12/2007 | Diekhans et al. |
| 2007/0298744 A1 | 12/2007 | Fitzner et al. |
| 2008/0030320 A1 | 2/2008 | Wilcox et al. |
| 2008/0098035 A1 | 4/2008 | Wippersteg et al. |
| 2008/0140431 A1 | 6/2008 | Anderson et al. |
| 2008/0177449 A1 | 7/2008 | Pickett et al. |
| 2008/0248843 A1 | 10/2008 | Birrell et al. |
| 2008/0268927 A1 | 10/2008 | Farley et al. |
| 2008/0269052 A1 | 10/2008 | Rosinger et al. |
| 2008/0289308 A1 | 11/2008 | Brubaker |
| 2008/0312085 A1 | 12/2008 | Kordes et al. |
| 2009/0044505 A1 | 2/2009 | Huster et al. |
| 2009/0074243 A1 | 3/2009 | Missotten et al. |
| 2009/0143941 A1 | 6/2009 | Tarasinski et al. |
| 2009/0192654 A1 | 7/2009 | Wendte et al. |
| 2009/0216410 A1 | 8/2009 | Allen et al. |
| 2009/0226036 A1 | 9/2009 | Gaal |
| 2009/0259483 A1 | 10/2009 | Hendrickson et al. |
| 2009/0265098 A1 | 10/2009 | Dix |
| 2009/0306835 A1 | 12/2009 | Ellermann et al. |
| 2009/0311084 A1 | 12/2009 | Coers et al. |
| 2009/0312919 A1 | 12/2009 | Foster et al. |
| 2009/0312920 A1 | 12/2009 | Boenig et al. |
| 2009/0325658 A1 | 12/2009 | Phelan et al. |
| 2010/0036696 A1 | 2/2010 | Lang et al. |
| 2010/0042297 A1 | 2/2010 | Foster et al. |
| 2010/0063626 A1 | 3/2010 | Anderson |
| 2010/0063648 A1 | 3/2010 | Anderson |
| 2010/0063651 A1 | 3/2010 | Anderson |
| 2010/0063664 A1 | 3/2010 | Anderson |
| 2010/0063954 A1 | 3/2010 | Anderson |
| 2010/0070145 A1 | 3/2010 | Foster et al. |
| 2010/0071329 A1 | 3/2010 | Hindryckx et al. |
| 2010/0094481 A1 | 4/2010 | Anderson |
| 2010/0121541 A1 | 5/2010 | Behnke et al. |
| 2010/0137373 A1 | 6/2010 | Hungenberg et al. |
| 2010/0145572 A1 | 6/2010 | Steckel et al. |
| 2010/0152270 A1 | 6/2010 | Suty-Heinze et al. |
| 2010/0152943 A1 | 6/2010 | Matthews |
| 2010/0217474 A1 | 8/2010 | Baumgarten et al. |
| 2010/0268562 A1 | 10/2010 | Anderson |
| 2010/0268679 A1 | 10/2010 | Anderson |
| 2010/0285964 A1 | 11/2010 | Waldraff et al. |
| 2010/0317517 A1 | 12/2010 | Rosinger et al. |
| 2010/0319941 A1 | 12/2010 | Peterson |
| 2010/0332051 A1 | 12/2010 | Kormann |
| 2011/0056178 A1 | 3/2011 | Sauerwein et al. |
| 2011/0059782 A1 | 3/2011 | Harrington |
| 2011/0072773 A1 | 3/2011 | Schroeder et al. |
| 2011/0084851 A1 | 4/2011 | Peterson et al. |
| 2011/0086684 A1 | 4/2011 | Luellen et al. |
| 2011/0160961 A1 | 6/2011 | Wollenhaupt et al. |
| 2011/0213531 A1 | 9/2011 | Farley et al. |
| 2011/0224873 A1 | 9/2011 | Reeve et al. |
| 2011/0227745 A1 | 9/2011 | Kikuchi et al. |
| 2011/0257850 A1 | 10/2011 | Reeve et al. |
| 2011/0270494 A1 | 11/2011 | Imhof et al. |
| 2011/0270495 A1 | 11/2011 | Knapp |
| 2011/0295460 A1 | 12/2011 | Hunt et al. |
| 2011/0307149 A1 | 12/2011 | Pighi et al. |
| 2012/0004813 A1 | 1/2012 | Baumgarten et al. |
| 2012/0029732 A1 | 2/2012 | Meyer et al. |
| 2012/0087771 A1 | 4/2012 | Wenzel |
| 2012/0096827 A1 | 4/2012 | Chaney et al. |
| 2012/0143642 A1 | 6/2012 | O'Neil |

(56) References Cited

U.S. PATENT DOCUMENTS

| | | |
|---|---|---|
| 2012/0215378 A1 | 8/2012 | Sprock et al. |
| 2012/0215379 A1 | 8/2012 | Sprock et al. |
| 2012/0253611 A1 | 10/2012 | Zielke et al. |
| 2012/0263560 A1 | 10/2012 | Diekhans et al. |
| 2012/0265412 A1 | 10/2012 | Diekhans et al. |
| 2012/0271489 A1 | 10/2012 | Roberts et al. |
| 2012/0323452 A1 | 12/2012 | Green et al. |
| 2013/0019580 A1 | 1/2013 | Anderson et al. |
| 2013/0022430 A1 | 1/2013 | Anderson et al. |
| 2013/0046419 A1 | 2/2013 | Anderson et al. |
| 2013/0046439 A1 | 2/2013 | Anderson et al. |
| 2013/0046525 A1 | 2/2013 | Ali et al. |
| 2013/0103269 A1 | 4/2013 | Hellgen et al. |
| 2013/0124239 A1 | 5/2013 | Rosa et al. |
| 2013/0184944 A1 | 7/2013 | Missotten et al. |
| 2013/0197767 A1 | 8/2013 | Lenz |
| 2013/0205733 A1 | 8/2013 | Peters et al. |
| 2013/0210505 A1 | 8/2013 | Bischoff |
| 2013/0231823 A1 | 9/2013 | Wang et al. |
| 2013/0319941 A1 | 12/2013 | Schneider |
| 2013/0325242 A1 | 12/2013 | Cavender-Bares et al. |
| 2013/0332003 A1 | 12/2013 | Murray et al. |
| 2014/0002489 A1 | 1/2014 | Sauder et al. |
| 2014/0019017 A1 | 1/2014 | Wilken et al. |
| 2014/0021598 A1 | 1/2014 | Sutardja |
| 2014/0050364 A1 | 2/2014 | Brueckner et al. |
| 2014/0067745 A1 | 3/2014 | Avey |
| 2014/0121882 A1 | 5/2014 | Gilmore et al. |
| 2014/0129048 A1 | 5/2014 | Baumgarten et al. |
| 2014/0172222 A1 | 6/2014 | Nickel |
| 2014/0172224 A1 | 6/2014 | Matthews et al. |
| 2014/0172225 A1 | 6/2014 | Matthews et al. |
| 2014/0208870 A1 | 7/2014 | Quaderer et al. |
| 2014/0215984 A1 | 8/2014 | Bischoff |
| 2014/0230391 A1 | 8/2014 | Hendrickson et al. |
| 2014/0230392 A1 | 8/2014 | Dybro et al. |
| 2014/0236381 A1 | 8/2014 | Anderson et al. |
| 2014/0236431 A1 | 8/2014 | Hendrickson et al. |
| 2014/0257911 A1 | 9/2014 | Anderson |
| 2014/0262547 A1 | 9/2014 | Acheson et al. |
| 2014/0277960 A1 | 9/2014 | Blank et al. |
| 2014/0297242 A1 | 10/2014 | Sauder et al. |
| 2014/0303814 A1 | 10/2014 | Burema et al. |
| 2014/0324272 A1 | 10/2014 | Madsen et al. |
| 2014/0331631 A1 | 11/2014 | Sauder et al. |
| 2014/0338298 A1 | 11/2014 | Jung et al. |
| 2014/0350802 A1 | 11/2014 | Biggerstaff et al. |
| 2014/0360148 A1 | 12/2014 | Wienker et al. |
| 2015/0049088 A1 | 2/2015 | Snyder et al. |
| 2015/0088785 A1 | 3/2015 | Chi |
| 2015/0095830 A1 | 4/2015 | Massoumi et al. |
| 2015/0101519 A1 | 4/2015 | Blackwell et al. |
| 2015/0105984 A1 | 4/2015 | Birrell et al. |
| 2015/0124054 A1 | 5/2015 | Darr et al. |
| 2015/0168187 A1 | 6/2015 | Myers |
| 2015/0211199 A1 | 7/2015 | Corcoran et al. |
| 2015/0230403 A1 | 8/2015 | Jung et al. |
| 2015/0242799 A1 | 8/2015 | Seki et al. |
| 2015/0243114 A1 | 8/2015 | Tanabe et al. |
| 2015/0254800 A1 | 9/2015 | Johnson et al. |
| 2015/0264863 A1 | 9/2015 | Muench et al. |
| 2015/0276794 A1 | 10/2015 | Pistrol et al. |
| 2015/0278640 A1 | 10/2015 | Johnson et al. |
| 2015/0285647 A1 | 10/2015 | Meyer zu Helligen et al. |
| 2015/0293029 A1 | 10/2015 | Acheson et al. |
| 2015/0302305 A1 | 10/2015 | Rupp et al. |
| 2015/0305238 A1 | 10/2015 | Klausmann et al. |
| 2015/0305239 A1 | 10/2015 | Jung |
| 2015/0327440 A1 | 11/2015 | Dybro et al. |
| 2015/0351320 A1 | 12/2015 | Takahara et al. |
| 2015/0370935 A1 | 12/2015 | Starr |
| 2015/0373902 A1 | 12/2015 | Pasquier |
| 2015/0379785 A1 | 12/2015 | Brown, Jr. et al. |
| 2016/0025531 A1 | 1/2016 | Bischoff et al. |
| 2016/0029558 A1 | 2/2016 | Dybro et al. |
| 2016/0052525 A1 | 2/2016 | Tuncer et al. |
| 2016/0057922 A1 | 3/2016 | Freiberg et al. |
| 2016/0066505 A1 | 3/2016 | Bakke et al. |
| 2016/0073573 A1 | 3/2016 | Ethington et al. |
| 2016/0078375 A1 | 3/2016 | Ethington et al. |
| 2016/0078570 A1 | 3/2016 | Ethington et al. |
| 2016/0088794 A1 | 3/2016 | Baumgarten et al. |
| 2016/0106038 A1 | 4/2016 | Boyd et al. |
| 2016/0084813 A1 | 5/2016 | Anderson et al. |
| 2016/0146611 A1 | 5/2016 | Matthews |
| 2016/0202227 A1 | 7/2016 | Mathur et al. |
| 2016/0203657 A1 | 7/2016 | Bell et al. |
| 2016/0212939 A1 | 7/2016 | Ouchida et al. |
| 2016/0215994 A1 | 7/2016 | Mewes et al. |
| 2016/0232621 A1 | 8/2016 | Ethington et al. |
| 2016/0247075 A1 | 8/2016 | Mewes et al. |
| 2016/0247082 A1 | 8/2016 | Stehling |
| 2016/0260021 A1 | 9/2016 | Marek |
| 2016/0286720 A1 | 10/2016 | Heitmann et al. |
| 2016/0286721 A1 | 10/2016 | Heitmann et al. |
| 2016/0286722 A1 | 10/2016 | Heitmann et al. |
| 2016/0309656 A1 | 10/2016 | Wilken et al. |
| 2016/0327535 A1 | 11/2016 | Cotton et al. |
| 2016/0330906 A1 | 11/2016 | Acheson et al. |
| 2016/0338267 A1 | 11/2016 | Anderson et al. |
| 2016/0342915 A1 | 11/2016 | Humphrey |
| 2016/0345485 A1 | 12/2016 | Acheson et al. |
| 2016/0360697 A1 | 12/2016 | Diaz |
| 2017/0013773 A1 | 1/2017 | Kirk et al. |
| 2017/0031365 A1 | 2/2017 | Sugumaran et al. |
| 2017/0034997 A1 | 2/2017 | Mayerle |
| 2017/0049045 A1 | 2/2017 | Wilken et al. |
| 2017/0055433 A1 | 3/2017 | Jamison |
| 2017/0082442 A1 | 3/2017 | Anderson |
| 2017/0083024 A1 | 3/2017 | Reijersen Van Buuren |
| 2017/0086381 A1 | 3/2017 | Roell et al. |
| 2017/0089741 A1 | 3/2017 | Takahashi et al. |
| 2017/0089742 A1 | 3/2017 | Bruns et al. |
| 2017/0090068 A1 | 3/2017 | Xiang et al. |
| 2017/0105331 A1 | 4/2017 | Herlitzius et al. |
| 2017/0105335 A1 | 4/2017 | Xu et al. |
| 2017/0112049 A1 | 4/2017 | Weisberg et al. |
| 2017/0112061 A1 | 4/2017 | Meyer |
| 2017/0115862 A1 | 4/2017 | Stratton et al. |
| 2017/0118915 A1 | 5/2017 | Middelberg et al. |
| 2017/0124463 A1 | 5/2017 | Chen et al. |
| 2017/0127606 A1 | 5/2017 | Horton |
| 2017/0160916 A1 | 6/2017 | Baumgarten et al. |
| 2017/0161627 A1 | 6/2017 | Xu et al. |
| 2017/0185086 A1 | 6/2017 | Sauder et al. |
| 2017/0188515 A1 | 7/2017 | Baumgarten et al. |
| 2017/0192431 A1 | 7/2017 | Foster et al. |
| 2017/0208742 A1 | 7/2017 | Ingibergsson et al. |
| 2017/0213141 A1 | 7/2017 | Xu et al. |
| 2017/0215330 A1 | 8/2017 | Missotten et al. |
| 2017/0223947 A1 | 8/2017 | Gall et al. |
| 2017/0227969 A1 | 8/2017 | Murray et al. |
| 2017/0235471 A1 | 8/2017 | Scholer et al. |
| 2017/0245434 A1 | 8/2017 | Jung et al. |
| 2017/0251600 A1 | 9/2017 | Anderson et al. |
| 2017/0270446 A1 | 9/2017 | Starr et al. |
| 2017/0270616 A1 | 9/2017 | Basso |
| 2017/0316692 A1 | 11/2017 | Rusciolelli et al. |
| 2017/0318743 A1 | 11/2017 | Sauder et al. |
| 2017/0322550 A1 | 11/2017 | Yokoyama |
| 2017/0332551 A1 | 11/2017 | Todd et al. |
| 2017/0336787 A1 | 11/2017 | Pichlmaier et al. |
| 2017/0370765 A1 | 12/2017 | Meier et al. |
| 2018/0000011 A1 | 1/2018 | Schleusner et al. |
| 2018/0014452 A1 | 1/2018 | Starr |
| 2018/0022559 A1 | 1/2018 | Knutson |
| 2018/0024549 A1 | 1/2018 | Hurd |
| 2018/0035622 A1 | 2/2018 | Gresch et al. |
| 2018/0054955 A1 | 3/2018 | Oliver |
| 2018/0060975 A1 | 3/2018 | Hassanzadeh |
| 2018/0070534 A1 | 3/2018 | Mayerle |
| 2018/0077865 A1 | 3/2018 | Gallmeier |
| 2018/0084709 A1 | 3/2018 | Wieckhorst et al. |
| 2018/0084722 A1 | 3/2018 | Wieckhorst et al. |

(56) References Cited

U.S. PATENT DOCUMENTS

| | | |
|---|---|---|
| 2018/0092301 A1 | 4/2018 | Vandike et al. |
| 2018/0092302 A1 | 4/2018 | Vandike et al. |
| 2018/0108123 A1 | 4/2018 | Baurer et al. |
| 2018/0120133 A1 | 5/2018 | Blank et al. |
| 2018/0121821 A1 | 5/2018 | Parsons et al. |
| 2018/0124992 A1 | 5/2018 | Koch et al. |
| 2018/0128933 A1 | 5/2018 | Koch et al. |
| 2018/0129879 A1 | 5/2018 | Achtelik et al. |
| 2018/0132422 A1 | 5/2018 | Hassanzadeh et al. |
| 2018/0136664 A1 | 5/2018 | Tomita et al. |
| 2018/0146612 A1 | 5/2018 | Sauder et al. |
| 2018/0146624 A1 | 5/2018 | Chen et al. |
| 2018/0153084 A1 | 6/2018 | Calleija et al. |
| 2018/0177125 A1 | 6/2018 | Takahara et al. |
| 2018/0181893 A1 | 6/2018 | Basso |
| 2018/0196438 A1 | 7/2018 | Newlin et al. |
| 2018/0196441 A1 | 7/2018 | Muench et al. |
| 2018/0211156 A1 | 7/2018 | Guan et al. |
| 2018/0232674 A1 | 8/2018 | Bilde |
| 2018/0242523 A1 | 8/2018 | Kirchbeck et al. |
| 2018/0249641 A1 | 9/2018 | Lewis et al. |
| 2018/0257657 A1 | 9/2018 | Blank et al. |
| 2018/0271015 A1 | 9/2018 | Redden et al. |
| 2018/0279599 A1 | 10/2018 | Struve |
| 2018/0295771 A1 | 10/2018 | Peters |
| 2018/0310474 A1 | 11/2018 | Posselius et al. |
| 2018/0317381 A1 | 11/2018 | Bassett |
| 2018/0317385 A1 | 11/2018 | Wellensiek et al. |
| 2018/0325012 A1 | 11/2018 | Ferrari et al. |
| 2018/0325014 A1 | 11/2018 | Debbaut |
| 2018/0332767 A1 | 11/2018 | Muench et al. |
| 2018/0338422 A1 | 11/2018 | Brubaker |
| 2018/0340845 A1 | 11/2018 | Rhodes et al. |
| 2018/0359917 A1 | 12/2018 | Blank et al. |
| 2018/0359919 A1 | 12/2018 | Blank et al. |
| 2018/0364726 A1 | 12/2018 | Foster et al. |
| 2019/0021226 A1 | 1/2019 | Dima et al. |
| 2019/0025175 A1 | 1/2019 | Laugwitz |
| 2019/0041813 A1 | 2/2019 | Horn et al. |
| 2019/0050948 A1 | 2/2019 | Perry et al. |
| 2019/0057460 A1 | 2/2019 | Sakaguchi et al. |
| 2019/0066234 A1 | 2/2019 | Bedoya et al. |
| 2019/0069470 A1 | 3/2019 | Pfeiffer et al. |
| 2019/0075727 A1 | 3/2019 | Duke et al. |
| 2019/0085785 A1 | 3/2019 | Abolt |
| 2019/0090423 A1 | 3/2019 | Escher et al. |
| 2019/0098825 A1 | 4/2019 | Neitemeier et al. |
| 2019/0104722 A1 | 4/2019 | Slaughter et al. |
| 2019/0108413 A1 | 4/2019 | Chen et al. |
| 2019/0114847 A1 | 4/2019 | Wagner et al. |
| 2019/0124819 A1 | 5/2019 | Madsen et al. |
| 2019/0129430 A1 | 5/2019 | Madsen et al. |
| 2019/0136491 A1 | 5/2019 | Martin et al. |
| 2019/0138962 A1 | 5/2019 | Ehlmann et al. |
| 2019/0147094 A1 | 5/2019 | Zhan et al. |
| 2019/0147249 A1 | 5/2019 | Kiepe et al. |
| 2019/0156255 A1 | 5/2019 | Carroll |
| 2019/0174667 A1 | 6/2019 | Gresch et al. |
| 2019/0183047 A1 | 6/2019 | Dybro et al. |
| 2019/0200522 A1 | 7/2019 | Hansen et al. |
| 2019/0230855 A1 | 8/2019 | Reed et al. |
| 2019/0239416 A1 | 8/2019 | Green et al. |
| 2019/0261550 A1 | 8/2019 | Damme et al. |
| 2019/0261559 A1 | 8/2019 | Heitmann et al. |
| 2019/0261560 A1 | 8/2019 | Jelenkovic |
| 2019/0313570 A1 | 10/2019 | Owechko |
| 2019/0327889 A1 | 10/2019 | Borgstadt |
| 2019/0327892 A1 | 10/2019 | Fries et al. |
| 2019/0335662 A1 | 11/2019 | Good et al. |
| 2019/0335674 A1 | 11/2019 | Basso |
| 2019/0343035 A1 | 11/2019 | Smith et al. |
| 2019/0343043 A1 | 11/2019 | Bormann et al. |
| 2019/0343044 A1 | 11/2019 | Bormann et al. |
| 2019/0343048 A1 | 11/2019 | Farley et al. |
| 2019/0351765 A1 | 11/2019 | Rabusic |
| 2019/0354081 A1 | 11/2019 | Blank et al. |
| 2019/0364733 A1 | 12/2019 | Laugen et al. |
| 2019/0364734 A1 | 12/2019 | Kriebel et al. |
| 2020/0000006 A1 | 1/2020 | McDonald et al. |
| 2020/0008351 A1 | 1/2020 | Zielke et al. |
| 2020/0015416 A1 | 1/2020 | Barther et al. |
| 2020/0019159 A1 | 1/2020 | Kocer et al. |
| 2020/0024102 A1 | 1/2020 | Brill et al. |
| 2020/0029488 A1 | 1/2020 | Bertucci et al. |
| 2020/0034759 A1 | 1/2020 | Dumstorff et al. |
| 2020/0037491 A1 | 2/2020 | Schoeny et al. |
| 2020/0053961 A1 | 2/2020 | Dix et al. |
| 2020/0064144 A1 | 2/2020 | Tomita et al. |
| 2020/0064863 A1 | 2/2020 | Tomita et al. |
| 2020/0074023 A1 | 3/2020 | Nizami et al. |
| 2020/0084963 A1 | 3/2020 | Gururajan et al. |
| 2020/0084966 A1 | 3/2020 | Corban et al. |
| 2020/0090094 A1 | 3/2020 | Blank |
| 2020/0097851 A1 | 3/2020 | Alvarez et al. |
| 2020/0113142 A1 | 4/2020 | Coleman et al. |
| 2020/0125822 A1 | 4/2020 | Yang et al. |
| 2020/0128732 A1 | 4/2020 | Chaney |
| 2020/0128733 A1 | 4/2020 | Vandike et al. |
| 2020/0128734 A1 | 4/2020 | Brammeier et al. |
| 2020/0128735 A1 | 4/2020 | Bonefas et al. |
| 2020/0128737 A1 | 4/2020 | Anderson et al. |
| 2020/0128738 A1 | 4/2020 | Suleman et al. |
| 2020/0128740 A1 | 4/2020 | Suleman |
| 2020/0133262 A1 | 4/2020 | Suleman et al. |
| 2020/0141784 A1 | 5/2020 | Lange et al. |
| 2020/0146203 A1 | 5/2020 | Deng |
| 2020/0150631 A1 | 5/2020 | Frieberg et al. |
| 2020/0154639 A1 | 5/2020 | Takahara et al. |
| 2020/0163277 A1 | 5/2020 | Cooksey et al. |
| 2020/0183406 A1 | 6/2020 | Borgstadt |
| 2020/0187409 A1 | 6/2020 | Meyer Zu Helligen |
| 2020/0196526 A1 | 6/2020 | Koch et al. |
| 2020/0202596 A1 | 6/2020 | Kitahara et al. |
| 2020/0221632 A1 | 7/2020 | Strnad et al. |
| 2020/0221635 A1 | 7/2020 | Hendrickson et al. |
| 2020/0221636 A1 | 7/2020 | Boydens et al. |
| 2020/0265527 A1 | 8/2020 | Rose et al. |
| 2020/0278680 A1 | 9/2020 | Schulz et al. |
| 2020/0317114 A1 | 10/2020 | Hoff |
| 2020/0319632 A1 | 10/2020 | Desai et al. |
| 2020/0319655 A1 | 10/2020 | Desai et al. |
| 2020/0323133 A1 | 10/2020 | Anderson et al. |
| 2020/0323134 A1 | 10/2020 | Darr et al. |
| 2020/0326674 A1 | 10/2020 | Palla et al. |
| 2020/0326727 A1 | 10/2020 | Palla et al. |
| 2020/0333278 A1 | 10/2020 | Locken et al. |
| 2020/0337232 A1 | 10/2020 | Blank et al. |
| 2020/0352099 A1 | 11/2020 | Meier et al. |
| 2020/0359547 A1 | 11/2020 | Sakaguchi et al. |
| 2020/0359549 A1 | 11/2020 | Sakaguchi et al. |
| 2020/0363256 A1 | 11/2020 | Meier et al. |
| 2020/0375083 A1 | 12/2020 | Anderson et al. |
| 2020/0375084 A1 | 12/2020 | Sakaguchi et al. |
| 2020/0378088 A1 | 12/2020 | Anderson |
| 2020/0404842 A1 | 12/2020 | Dugas et al. |
| 2021/0015041 A1 | 1/2021 | Bormann et al. |
| 2021/0129853 A1 | 5/2021 | Appleton et al. |
| 2021/0176916 A1 | 6/2021 | Sidon et al. |
| 2021/0176918 A1 | 6/2021 | Franzen et al. |
| 2021/0289687 A1 | 9/2021 | Heinold et al. |
| 2021/0321567 A1 | 10/2021 | Sidon et al. |

FOREIGN PATENT DOCUMENTS

| | | |
|---|---|---|
| BR | MU6800140 U | 12/1989 |
| BR | PI0502658 A | 2/2007 |
| BR | PI0802384 A2 | 3/2010 |
| BR | 102014007178 A2 | 8/2016 |
| CA | 1165300 A | 4/1984 |
| CA | 2283767 A1 | 3/2001 |
| CA | 2330979 A1 | 8/2001 |
| CN | 2451633 Y | 10/2001 |
| CN | 101236188 A | 8/2008 |
| CN | 101303338 A | 11/2008 |

(56) References Cited

FOREIGN PATENT DOCUMENTS

| | | |
|---|---|---|
| CN | 101363833 A | 2/2009 |
| CN | 201218789 Y | 4/2009 |
| CN | 101839906 A | 9/2010 |
| CN | 101929166 A | 12/2010 |
| CN | 102080373 A | 6/2011 |
| CN | 102277867 B | 12/2011 |
| CN | 202110103 U | 1/2012 |
| CN | 202119772 U | 1/2012 |
| CN | 202340435 U | 7/2012 |
| CN | 103181263 A | 7/2013 |
| CN | 203053961 U | 7/2013 |
| CN | 203055121 U | 7/2013 |
| CN | 203206739 U | 9/2013 |
| CN | 102277867 B | 10/2013 |
| CN | 204435344 U | 7/2015 |
| CN | 204475304 U | 7/2015 |
| CN | 105205248 A | 12/2015 |
| CN | 204989174 U | 1/2016 |
| CN | 105432228 A | 3/2016 |
| CN | 105741180 A | 7/2016 |
| CN | 106053330 A | 10/2016 |
| CN | 106198877 A | 12/2016 |
| CN | 106198879 A | 12/2016 |
| CN | 106226470 A | 12/2016 |
| CN | 106248873 A | 12/2016 |
| CN | 106290800 A | 1/2017 |
| CN | 106327349 A | 1/2017 |
| CN | 106644663 A | 5/2017 |
| CN | 206330815 U | 7/2017 |
| CN | 206515118 U | 9/2017 |
| CN | 206515119 U | 9/2017 |
| CN | 206616118 U | 11/2017 |
| CN | 206696107 | 12/2017 |
| CN | 206696107 U | 12/2017 |
| CN | 107576674 | 1/2018 |
| CN | 107576674 A | 1/2018 |
| CN | 206906093 U | 1/2018 |
| CN | 206941558 | 1/2018 |
| CN | 206941558 U | 1/2018 |
| CN | 107736088 A | 2/2018 |
| CN | 107795095 A | 3/2018 |
| CN | 207079558 | 3/2018 |
| CN | 107941286 A | 4/2018 |
| CN | 107957408 A | 4/2018 |
| CN | 207567744 U | 7/2018 |
| CN | 108614089 A | 10/2018 |
| CN | 208013131 U | 10/2018 |
| CN | 109357804 A | 2/2019 |
| CN | 109485353 A | 3/2019 |
| CN | 109633127 A | 4/2019 |
| CN | 109763476 A | 5/2019 |
| CN | 109961024 A | 7/2019 |
| CN | 110262287 A | 9/2019 |
| CN | 111201879 A | 5/2020 |
| CN | 111406505 A | 7/2020 |
| CS | 247426 B1 | 12/1986 |
| CS | 248318 B1 | 2/1987 |
| CZ | 17266 U1 | 2/2007 |
| CZ | 20252 U1 | 11/2009 |
| DE | 441597 C | 3/1927 |
| DE | 504035 C | 7/1930 |
| DE | 2354828 A1 | 5/1975 |
| DE | 152380 A1 | 11/1981 |
| DE | 3728669 A1 | 3/1989 |
| DE | 19509496 A1 | 9/1996 |
| DE | 19718455 A1 | 11/1997 |
| DE | 19705842 A1 | 8/1998 |
| DE | 19828355 A1 | 1/2000 |
| DE | 10050224 A1 | 4/2002 |
| DE | 10120173 A1 | 10/2002 |
| DE | 202004015141 U1 | 12/2004 |
| DE | 102005000770 B3 | 7/2006 |
| DE | 102005000771 A1 | 8/2006 |
| DE | 102008021785 A1 | 11/2009 |
| DE | 102009041646 A1 | 3/2011 |
| DE | 102010004648 A1 | 7/2011 |
| DE | 102010038661 A1 | 2/2012 |
| DE | 102011005400 A1 | 9/2012 |
| DE | 202012103730 U1 | 10/2012 |
| DE | 102011052688 A1 | 2/2013 |
| DE | 102012211001 A1 | 1/2014 |
| DE | 102012220109 | 5/2014 |
| DE | 102012223768 | 6/2014 |
| DE | 102013212151 A1 | 12/2014 |
| DE | 102013019098 B3 | 1/2015 |
| DE | 102014108449 A1 | 2/2015 |
| DE | 2014201203 A1 | 7/2015 |
| DE | 102014208068 A1 | 10/2015 |
| DE | 102015006398 B3 | 5/2016 |
| DE | 102015109799 A1 | 12/2016 |
| DE | 112015002194 T5 | 1/2017 |
| DE | 102017204511 A1 | 9/2018 |
| DE | 102019206734 A1 | 11/2020 |
| DE | 102019114872 A1 | 12/2020 |
| EP | 845198 B2 | 6/1998 |
| EP | 1444879 A1 | 8/2004 |
| EP | 1219159 B1 | 6/2005 |
| EP | 1219153 B1 | 2/2006 |
| EP | 1692928 A2 | 8/2006 |
| EP | 1574122 B1 | 2/2008 |
| EP | 1943877 A2 | 7/2008 |
| EP | 1598586 B1 | 9/2009 |
| EP | 1731983 B1 | 9/2009 |
| EP | 2146307 A2 | 1/2010 |
| EP | 0845198 B2 | 2/2010 |
| EP | 2186389 A1 | 5/2010 |
| EP | 2267566 A2 | 12/2010 |
| EP | 3491192 A2 | 12/2010 |
| EP | 2057884 B1 | 1/2011 |
| EP | 2146307 B1 | 5/2012 |
| EP | 2446732 A1 | 5/2012 |
| EP | 2524586 A2 | 11/2012 |
| EP | 2529610 A1 | 12/2012 |
| EP | 2174537 B1 | 5/2013 |
| EP | 2592919 A1 | 5/2013 |
| EP | 1674324 B2 | 5/2014 |
| EP | 2764764 B1 | 8/2014 |
| EP | 2191439 B1 | 3/2015 |
| EP | 2921042 A1 | 9/2015 |
| EP | 2944725 A1 | 11/2015 |
| EP | 2997805 A1 | 3/2016 |
| EP | 3000302 A1 | 3/2016 |
| EP | 2868806 B1 | 7/2016 |
| EP | 3085221 A1 | 10/2016 |
| EP | 3095310 A1 | 11/2016 |
| EP | 3097759 A1 | 11/2016 |
| EP | 2452551 B1 | 5/2017 |
| EP | 3175691 A1 | 6/2017 |
| EP | 3195719 A1 | 7/2017 |
| EP | 3195720 A1 | 7/2017 |
| EP | 3259976 A1 | 12/2017 |
| EP | 3262934 A1 | 1/2018 |
| EP | 3491192 A1 | 1/2018 |
| EP | 3287007 A1 | 2/2018 |
| EP | 3298876 A1 | 3/2018 |
| EP | 3300579 A1 | 4/2018 |
| EP | 3315005 A1 | 5/2018 |
| EP | 3316208 A1 | 5/2018 |
| EP | 2829171 B1 | 6/2018 |
| EP | 2508057 | 7/2018 |
| EP | 2508057 B1 | 7/2018 |
| EP | 3378298 A1 | 9/2018 |
| EP | 3378299 A1 | 9/2018 |
| EP | 2997805 A1 | 10/2018 |
| EP | 3384754 A1 | 10/2018 |
| EP | 3289853 B1 | 3/2019 |
| EP | 3456167 A1 | 3/2019 |
| EP | 3466239 A1 | 4/2019 |
| EP | 3469878 A1 | 4/2019 |
| EP | 3289852 B1 | 6/2019 |
| EP | 3491192 A1 | 6/2019 |
| EP | 3494770 A1 | 6/2019 |
| EP | 3498074 A1 | 6/2019 |
| EP | 3000302 B1 | 8/2019 |

(56) References Cited

FOREIGN PATENT DOCUMENTS

| | | | |
|---|---|---|---|
| EP | 3533314 A1 | 9/2019 |
| EP | 3569049 A1 | 11/2019 |
| EP | 3000307 B1 | 12/2019 |
| EP | 3586592 A2 | 1/2020 |
| EP | 3593613 A1 | 1/2020 |
| EP | 3593620 A1 | 1/2020 |
| EP | 3613272 A1 | 2/2020 |
| EP | 3243374 B1 | 3/2020 |
| EP | 3626038 A1 | 3/2020 |
| EP | 3259976 B1 | 4/2020 |
| EP | 3635647 A1 | 4/2020 |
| EP | 3378298 B1 | 5/2020 |
| EP | 3646699 A1 | 5/2020 |
| EP | 3662741 A1 | 6/2020 |
| EP | 3685648 A1 | 7/2020 |
| EP | 2995191 B2 | 10/2020 |
| ES | 2116215 A1 | 7/1998 |
| ES | 2311322 A1 | 2/2009 |
| FI | 5533 A | 11/1913 |
| FR | 1451480 A | 1/1966 |
| FR | 2817344 A1 | 5/2002 |
| FR | 2901291 A | 11/2007 |
| FR | 2901291 A1 | 11/2007 |
| GB | 901081 A | 7/1962 |
| GB | 201519517 A1 | 5/2017 |
| IN | 1632DE2014 A | 8/2016 |
| IN | 201641027017 A | 10/2016 |
| IN | 202041039250 A | 9/2020 |
| JP | 7079681 A | 11/1982 |
| JP | S60253617 A | 12/1985 |
| JP | S63308110 A | 12/1988 |
| JP | H02196960 A | 8/1990 |
| JP | H02215311 A | 8/1990 |
| JP | H0779681 A | 3/1995 |
| JP | H1066436 A | 3/1998 |
| JP | H10191762 A | 7/1998 |
| JP | 2000352044 A | 12/2000 |
| JP | 2001057809 A | 3/2001 |
| JP | 2002186348 A | 7/2002 |
| JP | 2005227233 A | 8/2005 |
| JP | 2006166871 A | 6/2006 |
| JP | 2011205967 A | 10/2011 |
| JP | 2015070812 A | 4/2015 |
| JP | 2015219651 A | 12/2015 |
| JP | 2016071726 A | 5/2016 |
| JP | 2016160808 A | 9/2016 |
| JP | 6087258 B2 | 3/2017 |
| JP | 2017136035 A | 8/2017 |
| JP | 2017137729 A | 8/2017 |
| JP | 2017195804 A | 11/2017 |
| JP | 2018068284 A | 5/2018 |
| JP | 2018102154 A | 7/2018 |
| JP | 2018151388 A | 9/2018 |
| JP | 2019004796 A | 1/2019 |
| JP | 2019129744 A | 8/2019 |
| JP | 2019146506 A | 9/2019 |
| JP | 2019216744 A | 12/2019 |
| JP | 2020018255 A | 2/2020 |
| JP | 2020031607 A | 3/2020 |
| JP | 2020113062 A | 7/2020 |
| JP | 2020127405 A | 8/2020 |
| KR | 100974892 | 8/2010 |
| KR | 100974892 B1 | 8/2010 |
| KR | 20110018582 A | 2/2011 |
| KR | 101067576 B | 9/2011 |
| KR | 101067576 B1 | 9/2011 |
| KR | 101134075 B1 | 4/2012 |
| KR | 101447197 B1 | 10/2014 |
| KR | 101653750 | 9/2016 |
| KR | 20170041377 A | 4/2017 |
| KR | 200485051 Y | 11/2017 |
| KR | 200485051 Y1 | 11/2017 |
| KR | 101873657 B | 8/2018 |
| MX | GT06000012 A | 1/2008 |
| PL | 178299 B1 | 4/2000 |
| RO | 130713 | 11/2015 |
| RU | 1791767 C | 1/1993 |
| RU | 2005102554 A | 7/2006 |
| RU | 2421744 C | 6/2011 |
| RU | 2421744 C1 | 6/2011 |
| RU | 2447640 C1 | 4/2012 |
| RU | 2502047 C | 12/2013 |
| RU | 2502047 C1 | 12/2013 |
| RU | 164128 | 8/2016 |
| RU | 2017114139 A | 4/2017 |
| RU | 2017114139 A | 10/2018 |
| RU | 2017114139 A3 | 5/2019 |
| SU | 834514 A1 | 5/1981 |
| SU | 887717 A1 | 12/1981 |
| SU | 1052940 A1 | 11/1983 |
| SU | 1134669 A1 | 1/1985 |
| SU | 1526588 A1 | 12/1989 |
| SU | 1540053 A1 | 1/1991 |
| SU | 1761864 A1 | 9/1992 |
| WO | 1986005353 A1 | 9/1986 |
| WO | 2001052160 A1 | 7/2001 |
| WO | 2002015673 A1 | 2/2002 |
| WO | 2003005803 A1 | 1/2003 |
| WO | 2007050192 A2 | 5/2007 |
| WO | 2009156542 A1 | 12/2009 |
| WO | 2010003421 A1 | 1/2010 |
| WO | 2011104085 A1 | 9/2011 |
| WO | 2012041621 A1 | 4/2012 |
| WO | 2012110508 A1 | 8/2012 |
| WO | 2012110544 A1 | 8/2012 |
| WO | 2013063106 A2 | 5/2013 |
| WO | 2013079247 A1 | 6/2013 |
| WO | 2013086351 A1 | 6/2013 |
| WO | 2013087275 A1 | 6/2013 |
| WO | 2014046685 A1 | 3/2014 |
| WO | 2014093814 A1 | 6/2014 |
| WO | 2014195302 A1 | 12/2014 |
| WO | 2015038751 A1 | 3/2015 |
| WO | 2015153809 A1 | 10/2015 |
| WO | 2016020595 A1 | 2/2016 |
| WO | 2016118686 A1 | 7/2016 |
| WO | 2017008161 A1 | 1/2017 |
| WO | 2017060168 A1 | 4/2017 |
| WO | 2017077113 A1 | 5/2017 |
| WO | 2017096489 A1 | 6/2017 |
| WO | 2017099570 A1 | 6/2017 |
| WO | 2017116913 A1 | 7/2017 |
| WO | 2017170507 A1 | 10/2017 |
| WO | 2017205406 A1 | 11/2017 |
| WO | 2017205410 A1 | 11/2017 |
| WO | 2018043336 A1 | 3/2018 |
| WO | 2018073060 A1 | 4/2018 |
| WO | 2018081759 A1 | 5/2018 |
| WO | 2018112615 | 6/2018 |
| WO | 2018116772 A1 | 6/2018 |
| WO | 2018142768 A1 | 8/2018 |
| WO | 2018200870 A1 | 11/2018 |
| WO | 2018206587 A1 | 11/2018 |
| WO | 2018220159 A1 | 12/2018 |
| WO | 2018226139 A1 | 12/2018 |
| WO | 2018235486 A1 | 12/2018 |
| WO | 2018235942 A1 | 12/2018 |
| WO | WO18235486 A1 | 12/2018 |
| WO | 2019034213 A1 | 2/2019 |
| WO | 2019079205 A1 | 4/2019 |
| WO | 2019081349 A1 | 5/2019 |
| WO | 2019091535 A1 | 5/2019 |
| WO | 2019109191 A1 | 6/2019 |
| WO | 2019124174 A1 | 6/2019 |
| WO | 2019124217 A1 | 6/2019 |
| WO | 2019124225 A1 | 6/2019 |
| WO | 2019124273 A1 | 6/2019 |
| WO | 2019129333 A1 | 7/2019 |
| WO | 2019129334 A1 | 7/2019 |
| WO | 2019129335 A1 | 7/2019 |
| WO | 2019215185 A1 | 11/2019 |
| WO | 2019230358 A1 | 12/2019 |
| WO | 2020026578 A1 | 2/2020 |
| WO | 2020026650 A1 | 2/2020 |

(56) References Cited

FOREIGN PATENT DOCUMENTS

| WO | 2020026651 A1 | 2/2020 |
| --- | --- | --- |
| WO | 2020031473 A1 | 2/2020 |
| WO | 2020038810 A1 | 2/2020 |
| WO | 2020039312 A1 | 2/2020 |
| WO | 2020039671 A1 | 2/2020 |
| WO | 2020044726 A1 | 3/2020 |
| WO | 2020082182 A1 | 4/2020 |
| WO | 2020100810 A1 | 5/2020 |
| WO | 2020110920 A1 | 6/2020 |
| WO | 2020195007 A1 | 10/2020 |
| WO | 2020206941 A1 | 10/2020 |
| WO | 2020206942 A1 | 10/2020 |
| WO | 2020210607 A1 | 10/2020 |
| WO | 2020221981 A1 | 11/2020 |
| WO | 2021262500 A1 | 12/2021 |

OTHER PUBLICATIONS

U.S. Appl. No. 16/831,216 Application and Drawings filed Mar. 26, 2020, 56 pages.
Notice of Allowance for U.S. Appl. No. 16/380,531 dated Apr. 5, 2021, 5 pages.
Martin et al. Breakage Susceptibiltiy and Hardness of Corn Kernels of Various Sizes and Shapes, vol. 3(): May 1087, 10 pages, https://pdfs.semanticscholar.org/e579/1b5363b6a78efd44adfb97755a0cdd14f7ca.pdf.
Hoff, "Combine Adjustments" (https://smallfarmersjournal.com/combine-adjustments/), Mar. 1943, 9 pages.
Optimizing Crop Profit Across Multiple Grain Attributes and Stover, Electronic Publication Date May 26, 2009, 17 pages.
Unglesbee, Soybean Pod Shatter—Bad Enough to Scout Before Harvest—DTN, Oct. 17, 2018, 11 pages. Susceptibility to shatter (https://agfax.com/2018/10/17/soybean-pod-shatter-bad-enough-to-scout-before-harvest-dtn/).
GIS Maps for Agricultural, accessed on May 10, 2022, 7 pages, https://www.satimagingcorp.com/services/geographic-information-systems/gis-maps-agriculture-mapping.
https://wingtra.com/drone-mapping-applications/use-of-drones-in-agriculture, accessed on May 10, 2022. 19 pages.
Energy Requirement Model for a Combine Harvester: Part 1: Development of Component Models, Published online Dec. 22, 2004, 17 pages.
Energy Requirement Model for a Combine Harvester, Part 2: Integration of Component Models, Published online Jan. 18, 2005, 11 pages.
Pioneer on reducing soybean harvest losses including combine adjustments (last accessed Jul. 23, 2020) (https://www.pioneer.com/us/agronomy/reducing_harvest_losses_in_soybeans.html), 5 pages.
Extended European Search Report and Written Opinion issued in European Patent Application No. 20208171.7, dated May 11, 2021, in 05 pages.
Cordoba, M.A., Bruno, C.I. Costa, J.L. Peralta, N.R. and Balzarini, M.G., 2016, Protocol for multivariate homogeneous zone delineation in precision agriculture, biosystems engineering, 143, pp. 95-107.
Pioneer Estimator, "Corn Yield Estimator" accessed on Feb. 13, 2018, 1 page. retrieved from: https://www.pioneer.com/home/site/us/tools-apps/growing-tools/corn-yield-estimator/.
Guindin, N. "Estimating Maize Grain Yield From Crop Biophysical Parameters Using Remote Sensing", Nov. 4, 2013, 19 pages.
EP Application No. 19203883.4-1004 Office Action dated May 3, 2021, 4 pages.
Iowa State University Extension and Outreach, "Harvest Weed Seed Control", Dec. 13, 2018, 6 pages. https://crops.extension.iastate.edu/blog/bob-hartzler/harvest-weed-seed-control.
Getting Rid of WeedsThrough Integrated Weed Management, accessed on Jun. 25, 2021, 10 pages. https://integratedweedmanagement.org/index.php/iwm-toolbox/the-harrington-seed-destructor.
The Importance of Reducing Weed Seeds, Jul. 2018, 2 pages. https://www.aphis.usda.gov/plant_health/soybeans/soybean-handouts.pdf.
Alternative Crop Guide, Published by the Jefferson Institute, "Buckwheat", Revised Jul. 2002. 4 pages.
Application and Drawings for U.S. Appl. No. 16/175,993, filed Oct. 31, 2018, 28 pages.
Application and Drawings for U.S. Appl. No. 16/380,623, filed Apr. 10, 2019, 36 pages.
Application and Drawings for U.S. Appl. No. 16/783,511, filed Feb. 6, 2020, 55 pages.
"Automated Weed Detection With Drones" dated May 25, 2017, retrieved at: <<https://www.precisionhawk.com/blog/media/topic/automated-weed-identification-with-drones>>, retrieved on Jan. 21, 2020, 4 pages.
F. Forcella, "Estimating the Timing of Weed Emergence", Site-Specific Management Guidelines, retrieved at: <<http://www.ipni.net/publication/ssmg.nsf/0/D26EC9A906F9B8C9852579E500773936/$FILE/SSMG-20.pdf>>, retrieved on Jan. 21, 2020, 4 pages.
Chauhan et al., "Emerging Challenges and Opportunities for Education and Research in Weed Science", frontiers in Plant Science. Published online Sep. 5, 2017, 22 pages.
Apan, A., Wells ,N., Reardon-Smith, K, Richardson, L, McDougall, K, and Basnet, B.B., 2008. Predictive mapping of blackberry in the Condamine Catchment using logistic regression and spatial analysis. In Proceedings of the 2008 Queensland Spatial Conference: Global Warning: What's Happening in Paradise. Spatial Sciences Institute, 11 pages.
Jarnevich, C.S., Holcombe, T.R., Barnett, D.T., Stohlgren, T.J. and Kartesz, J.T., 2010. Forecasting weed distributions using climate data: a GIS early warning tool. Invasive Plant Science and Management. 3(4), pp. 365-375.
Sa et al., "WeedMap: A Large-Scale Semantic Weed Mapping Framework Using Aerial Multispectral Imaging and Deep Neural Network for Precision Farming", Sep. 6, 2018, 25 pages.
Pflanz et al., "Weed Mapping with UAS Imagery and a Bag of Visual Words Based Image Classifier", Published Sep. 24, 2018, 28 pages.
Provisional Application and Drawings for U.S. Appl. No. 62/928,964, filed Oct. 31, 2019, 14 pages.
Application and Drawings for U.S. Appl. No. 16/783,475, filed Feb. 6, 2020, 55 pages.
U.S. Appl. No. 17/067,483 Application and Drawings as filed on Oct. 9, 2020, 63 pages.
U.S. Appl. No. 17/066,442 Application and Drawings as filed on Oct. 8, 2020, 65 pages.
U.S. Appl. No. 16/380,550, filed Apr. 10, 2019, Application and Drawings, 47 pages.
U.S. Appl. No. 17/066,999 Application and Drawings as filed on Oct. 9, 2020, 67 pages.
U.S. Appl. No. 17/066,444 Application and Drawings as filed on Oct. 8, 2020, 102 pages.
Extended Search Report for European Patent Application No. 20167930.5 dated Sep. 15, 2020, 8 pages.
Extended Search Report for European Patent Application No. 19205901.2 dated Mar. 17, 2020, 6 pages.
Notice of Allowance for U.S. Appl. No. 16/171,978, dated Dec. 15, 2020, 21 pages.
Zhigen et al., "Research of the Combine Harvester Load Feedback Control System Using Multi-Signal Fusion Method and Fuzzy Algorithm," 2010, Publisher: IEEE, 5 pages.
Dan et al., "On-the-go Throughput Prediction in a Combine Harvester Using Sensor Fusion," 2017, Publisher: IEEE, 6 pages.
Fernandez-Quintanilla et al., "Is the current state of the art of weed monitoring sutible for site-specific weed management in arable crops?", First Published May 1, 2018, 4 pages.
Dionysis Bochtis et al. "Field Operations Planning for Agricultural Vehicles: A Hierarchical Modeling Framework." Agricultural Engineering International: the CIGR Ejournal. Manuscript PM 06 021. vol. IX. Feb. 2007, pp. 1-11.
U.S. Appl. No. 16/432,557, filed Jun. 5, 2019, 61 pages.
European Search Report issued in counterpart European Patent Application No. 19205142.3 dated Feb. 28, 2020 (6 pages).

(56) References Cited

OTHER PUBLICATIONS

Mei-Ju et al., "Two paradigms in cellular Internet-of-Things access for energy-harvesting machine-to-machine devices: push-based versus pull-based," 2016, vol. 6, 9 pages.
Yi et al., "An Efficient MAC Protocol With Adaptive Energy Harvesting for Machine-to-Machine Networks," 2015, vol. 3, Publisher: IEEE, 10 pages.
Application and Drawings for U.S. Appl. No. 16/171,978, filed Oct. 26, 2018, 53 pages.
European Search Report issued in European Patent Application No. 19203883.4 dated Mar. 23, 2020 (10 pages).
Notice of Allowance for U.S. Appl. No. 16/171,978 dated Oct. 28, 2020, 5 pages.
Notice of Allowance for U.S. Appl. No. 16/171,978, dated Aug. 7, 2020, 9 pages.
K.R. Manjunath et al., "Developing Spectral Library of Major Plant Species of Western Himalayas Using Ground Observations", J. Indian Soc Remote Sen (Mar. 2014) 42(a):201-216, 17 pages.
U.S. Appl. No. 16/380,564 Application and Drawings as filed on Apr. 10, 2019, 55 pages.
S. Veenadhari et al., "Machine Learning Approach For Forecasting Crop Yield Based on Climatic Parameters", 2014 International Conference on Computer Communication and Informatics (ICCCI—2014) Jan. 3-6, 2014, Coimbatore, India, 5 pages.
Non-Final Office Action for U.S. Appl. No. 16/380,531 dated Oct. 21, 2020, 10 pages.
U.S. Appl. No. 16/380,531 Application and Drawings as filed Apr. 10, 2019, 46 pages.
Lamsal et al. "Sugarcane Harvest Logistics in Brazil" Iowa Research Online, Sep. 11, 2013, 27 pages.
Jensen, "Algorithms for Operational Planning of Agricultural Field Operations", Mechanical Engineering Technical Report ME-TR-3, Nov. 9, 2012, 23 pages.
Chauhan, "Remote Sensing of Crop Lodging", Nov. 16, 2020, 16 pages.
Notice of Allowance for U.S. Appl. No. 16/432,557 dated Mar. 22, 2021, 9 pages.
Zhao, L., Yang, J., Li, P. and Zhang, L., 2014. Characteristics analysis and classification of crop harvest patterns by exploiting high-frequency multipolarization SAR data. IEEE Journal of Selected Topics in Applied Earth Observations and Remote Sensing, 7(9), pp. 3773-3783.
Feng-jie, X., Er-da, W. and Feng-yuan, X., Crop area yield risk evaluation and premium rates calculation—Based on nonparametric kernel density estimation. In 2009 International Conference on Management Science and Engineering, 7 pages.
Liu, R. and Bai, X., 2014, May. Random fuzzy production and distribution plan of agricultural products and its PSO algorithm. In 2014 IEEE International Conference on Progress in Informatics and Computing (pp. 32-36). IEEE.
Notice of Allowance for U.S. Appl. No. 16/171,978 dated Mar. 31, 2021, 6 pages.
Application and Drawings for U.S. Appl. No. 17/067,383, filed Oct. 9, 2020, 61 pages.
Apan et al., "Predictive Mapping of Blackberry in the Condamine Catchment Using Logistic Regressiona dn Spatial Analysis", Jan. 2008, 12 pages.
Robson, "Remote Sensing Applications for the Determination of Yield, Maturity and Aflatoxin Contamination in Peanut", Oct. 2007, 275 pages.
Bhattarai et al., "Remote Sensing Data to Detect Hessian Fly Infestation in Commercial Wheat Fields", Apr. 16, 2019, 8 pages.
Towery, et al., "Remote Sensing of Crop Hail Damage", Jul. 21, 1975, 31 pages.
Sa et al., "WeedMap: A Large-Scale Semantic Weed Mapping Framework Using Aerial Multispectral Imaging and Deep Neural Network for Precision Farming", Sep. 7, 2018, 25 pages.
Mathyam et al., "Remote Sensing of Biotic Stress in Crop Plants and Its Applications for Pest Management", Dec. 2011, 30 pages.
Martinez-Feria et al., "Evaluating Maize and Soybean Grain Dry-Down In the Field With Predictive Algorithms and Genotype-by-Environmental Analysis", May 9, 2019, 13 pages.
"GIS Maps for Agriculture", Precision Agricultural Mapping, Retrieved Dec. 11, 2020, 6 pages.
Paul, "Scabby Wheat Grain? Increasing Your Fan Speed May Help", https://agcrops.osu.edu/newsletter/corn-newsletter/2015-20/scabby-wheat-grain-increasing-yourfan-speed-may-help, C.O.R.N Newsletter//2015-20, 3 pages.
Clay et al., "Scouting for Weeds", SSMG-15, 4 pages, 2002.
Taylor et al., "Sensor-Based Variable Rate Application for Cotton", 8 pages, 2010.
Christiansen et al., "Designing and Testing a UAV Mapping System for Agricultural Field Surveying", Nov. 23, 2017, 19 pages.
Haung et al., "AccurateWeed Mapping and Prescription Map Generation Based on Fully Convolutional Networks Using UAV Imagery", Oct. 1, 2018, 12 pages.
Ma et al., Identification of Fusarium Head Blight in Winter Wheat Ears Using Continuous Wavelet Analysis, Dec. 19, 2019, 15 pages.
Morrison, "Should You Use Tillage to Control Resistant Weeds", Aug. 29, 2014, 9 pages.
Morrison, "Snow Trapping Snars Water", Oct. 13, 2005, 3 pages.
"Soil Zone Index", https://www.satimagingcorp.com/applications/natural-resources/agricultu . . . , Retrieved Dec. 11, 2020, 5 pages.
Malvic, "Soybean Cyst Nematode", University of Minnesota Extension, Oct. 19, 2020, 3 pages.
Unglesbee, "Soybean Pod Shatter—Bad Enough to Scout Before Harvest?—DTN", Oct. 17, 2018, 4 pages.
Tao, "Standing Crop Residue Can Reduce Snow Drifting and Increase Soil Moisture", 2 pages, last accessed Jul. 14, 2020.
Berglund, et al., "Swathing and Harvesting Canola", Jul. 2019, 8 pages.
Bell et al., "Synthetic Aperture Radar and Optical Remote Sensing of Crop Damage Attributed to Severe Weather in the Central United States", Jul. 25, 2018, 1 page.
Rosencrance, "Tabletop Grapes in India to Be Picked by Virginia Tech Robots", Jul. 23, 2020, 8 pages.
Lofton, et al., The Potential of Grazing Grain Sorghum Residue Following Harvest, May 13, 2020, 11 pages.
Beal et al., "Time Shift Evaluation to Improve Yield Map Quality", Published in Applied Engineering in Agriculture vol. 17(3): 385-390 (© 2001 American Society of Agricultural Engineers), 9 pages.
"Tips and Tricks of Harvesting High Moisture Grain", https://www.koenigequipment.com/blog/tips-and-tricks-of-harvesting-highmoisture-grain, 7 pages, last accessed Jul. 14, 2020.
Ransom, "Tips for Planting Winter Wheat and Winter Rye (for Grain) (Aug. 15, 2019)", 2017, 3 pages.
AgroWatch Tree Grading Maps, "The Grading Maps and Plant Count Reports", https://www.satimagingcorp.com/applications/natural-resources/agricultu . . . , Retrieved Dec. 11, 2020, 4 pages.
Ackley, "Troubleshooting Abnormal Corn Ears", Jul. 23, 2020, 25 pages.
Smith, "Understanding Ear Flex", Feb. 25, 2019, 17 pages.
Carroll et al., "Use of Spectral Vegetation Indicies Derived from Airborne Hyperspectral Imagery for Detection of European Corn Borer Infestation in Iowa Com Plots", Nov. 2008, 11 pages.
Agriculture, "Using drones in agriculture and capturing actionable data", Retrieved Dec. 11, 2020, 18 pages.
Bentley et al., "Using Landsatto Identify Thunderstorm Damage in Agricultural Regions", Aug. 28, 2001, 14 pages.
Duane Grant and the Idaho Wheat Commission, "Using Remote Sensing to Manage Wheat Grain Protein", Jan. 2, 2003, 13 pages.
Zhang et al., "Using satellite multispectral imagery for damage mapping of armyworm (Spodoptera frugiperda) in maize at a regional scale", Apr. 10, 2015, 14 pages.
Booker, "VIDEO: Canadian cage mill teams up with JD", Dec. 19, 2019, 6 pages.
AgTalk Home, "Best Combine to Handle Weeds", Posted Nov. 23, 2018, 9 pages.
"Volunteer corn can be costly for soybeans", Jun. 2, 2016, 1 page.
Pflanz, et al., "Weed Mapping with UAS Imagery and a Bag of Visual Words Based Image Classifier", Published Sep. 24, 2018, 17 pages.

(56) References Cited

OTHER PUBLICATIONS

Hartzler, "Weed seed predation in agricultural fields", 9 pages, 2009.
Sa et al., "Weedmap: A Large-Scale Sematnic Weed Mapping Framework Using Aerial Multispectral Imaging and Deep Neural Netowrk for Precision Farming", Sep. 6, 2018, 25 pages.
Nagelkirk, Michigan State University-Extension, "Wheat Harvest: Minimizing the Risk of Fusarium Head Scab Losses", Jul. 11, 2013, 4 pages.
Saskatchewan, "Wheat: Winter Wheat", (https://www.saskatchewan.ca/business/agriculture-natural-resources-and-industry/agribusiness-farmers-and-ranchers/crops-and-irrigation/field-crops/cereals-barley-wheat-oats-triticale/wheat-winter-wheat) 5 pages, last accessed Jul. 14, 2020.
Quora, "Why would I ever use sport mode in my automatic transmission car? Will this incrase fuel efficiency or isit simply a feature that makes form more fun when driving?", Aug. 10, 2020, 5 pages.
Wade, "Using a Drone's Surface Model to Estimate Crop Yields & Assess Plant Health", Oct. 19, 2015, 14 pages.
Mathyam et al., "Remote Sensing of Biotic Stress in Crop Plants and Its Applications for Pest Stress", Dec. 2011, 30 pages.
"Four Helpful Weed-Management Tips for Harvest Time", 2 pages, Sep. 4, 2019.
Franz et al., "The role of topography, soil, and remotely sensed vegetation condition towards predicting crop yield", University of Nebraska—Lincoln, Mar. 23, 2020, 44 pages.
Peiffer et al., The Genetic Architecture of Maize Stalk Strength:, Jun. 20, 2013, 14 pages.
7 Combine Tweaks to Boost Speed (https://www.agriculture.com/machinery/harvest-equipment/7-combine-tweaks-to-boost-speed_203-ar33059) 8 pages, Aug. 19, 2018.
Managing corn harvest this fall with variable corn conditions (https://www.ocj.com/2019/10/managing-corn-harvest-this-fall-with-variable-corn-conditions/), 4 pages, Oct. 10, 2019.
Reducing Aflatoxin in Corn During Harvest and Storage (https://extension.uga.edu/publications/detail.html?number=B1231&title=Reducing%20Aflatoxin%20in%20Corn%20During%20Harvest%20and%20Storage), 9 pages, Published with Full Review on Apr. 19, 2017.
Variable Rate Applications to Optimize Inputs (https://www.cotton.org/tech/physiology/cpt/miscpubs/upload/CPT-v9No2-98-REPOP.pdf), 8 pages, Nov. 2, 1998.
Robin Booker, VIDEO: Canadian cage mill teams up with JD (https://www.producer.com/2019/12/video-canadian-cage-mill-teams-up-with-jd/) , 6 pages, Dec. 19, 2019.
Jarnevich, et al. "Forecasting Weed Distributions using Climate Data: A GIS Early Warning Tool", Invasive Plant Science and Management, 11 pages, Jan. 20, 2017.
Burks, "Classification of Weed Species Using Color Texture Features and Discriminant Analysis" (http://citeseerx.ist.psu.edu/viewdoc/download?doi=10.1.1.468.5833&rep=rep1&type=pdf), 8 pages, 2000.
John Deere, https://www.youtube.com/watch?v=1Gq77CfdGI4&list=PL1KGsSJ4CWk4rShNb3-sTMOIiL8meHBL5 (last accessed Jul. 14, 2020), Jun. 15, 2020, 5 pages.
Combine Adjustments (http://corn.agronomy.wisc.edu/Management/L036.aspx), 2 pages, Originally written Feb. 1, 2006; last updated Oct. 18, 2018.
Ardekani, "Off- and on-ground GPR techniques for field-scale soil moisture mapping" Jun. 2013, 13 pages.
Does an Adaptive Gearbox Really Learn How You Drive? (https://practicalmotoring.com.au/voices/does-an-adaptive-gearbox-really-learn-how-you-drive/), Oct. 30, 2019, 8 pages.
https://www.researchgate.net/publication/222527694_Energy_Requirement_Model_for_a_Combine_Harvester_Part_I_Development_of_Component _Models, Abstract Only, Jan. 2005.
http://canola.okstate.edu/cropproduction/harvesting, 8 pages, Aug. 2011.
"Tips and Tricks of Harvesting High Moisture Grain", https://www.koenigequipment.com/blog/tips-and-tricks-of-harvesting-highmoisture-grain, 5 pages, last accessed Feb. 11, 2021.
Hoff, Combine Adjustements, Mar. 1943, 8 pages.
Haung et al., "Accurate Weed Mapping and Prescription Map Generation Based onFully Convolutional Networks Using UAV Imagery", 14 pages, Oct. 1, 2018.
Thompson, "Morning glory can make it impossible to harvest corn", Feb. 19, 2015, 4 pages.
Martin et al., "Breakage Susceptibility and Harness of Corn Kernels of Various Sizes and Shapes", May 1987, 10 pages.
Jones et al., "Brief history of agricultural systems modeling" Jun. 21, 2016, 15 pages.
Dan Anderson, "Brief history of agricultural systems modeling" 1 pages. Aug. 13, 2019.
A.Y. Şeflek, "Determining the Physico-Mechanical Characteristics of Maize Stalks Fordesigning Harvester", The Journal of Animal & Plant Sciences, 27(3): 2017, p. 855-860 ISSN: 1018-7081, Jun. 1, 2017.
Carmody, Paul, "Windrowing and harvesting", 8 pages Date: Feb. 3, 2010.
Dabney, et al., "Forage Harvest Representation in RUSLE2", Published Nov. 15, 2013, 17 pages.
John Deere S-Series Combines S760, S770, S780, S790 Brochure, 44 pages, Nov. 15, 2017.
Sekhon et al., "Stalk Bending Strength is Strongly Assoicated with Maize Stalk Lodging Incidence Across Multiple Environments", Jun. 20, 2019, 23 pages.
Thomison et al. "Abnormal Corn Ears", Apr. 28, 2015, 1 page.
Anderson, "Adjust your Combine to Reduce Damage to High Moisture Corn", Aug. 13, 2019, 11 pages.
Sumner et al., "Reducing Aflatoxin in Corn During Harvest and Storage", Reviewed by John Worley, Apr. 2017, 6 pages.
Sick, "Better understanding corn hybrid characteristics and properties can impact your seed decisions", 8 pages, Sep. 21, 2018.
TraCI/Change Vehicle State—SUMO Documentation, 10 pages, Retrieved Dec. 11, 2020.
Arnold, et al., Chapter 8. "Plant Growth Component", Jul. 1995, 41 pages.
Humburg, Chapter: 37 "Combine Adjustments to Reduce Harvest Losses", 2019, South Dakota Board of Regents, 8 pages.
Hoff, "Combine Adjustments", Cornell Extension Bulletin 591, Mar. 1943, 10 pages.
University of Wisconsin, Corn Agronomy, Originally written Feb. 1, 2006 | Last updated Oct. 18, 2018, 2 pages.
University of Nebraska-Lincoln, "Combine Adjustments for Downed Corn—Crop Watch", Oct. 27, 2017, 5 pages.
"Combine Cleaning: Quick Guide To Removing Resistant Weed Seeds (Among Other Things)", Nov. 2006, 5 pages.
Dekalb, "Corn Drydown Rates", 7 pages, Aug. 4, 2020.
Mahmoud et al. Iowa State University, "Corn Ear Orientation Effects on Mechanical Damage and Forces on Concave", 1975, 6 pages.
Sindelar et al., Kansas State University, "Corn Growth & Development" Jul. 17, 2017, 9 pages.
Pannar, "Manage the Growth Stages of the Maize Plant With Pannar", Nov. 14, 2016, 7 pages.
He et al., "Crop residue harvest impacts wind erodibility and simulated soil loss in the Central Great Plains", Sep. 27, 2017, 14 pages.
Blanken, "Designing a Living Snow Fence for Snow Drift Control", Jan. 17, 2018, 9 pages.
Jean, "Drones give aerial boost to ag producers", Mar. 21, 2019, 4 pages.
Zhao et al., "Dynamics modeling for sugarcane sucrose estimation using time series satellite imagery", Jul. 27, 2017, 11 pages.
Brady, "Effects of Cropland Conservation Practices on Fish and Wldlife Habitat", Sep. 1, 2007, 15 pages.
Jasa, et al., "Equipment Adjustments for Harvesting Soybeans at 13%-15% Moisture", Sep. 15, 2017, 2 pages.
Bendig et al., "Estimating Biomass of Barley Using Crop Surface Models (CSMs) Derived from UAV-Based RGB Imaging", Oct. 21, 2014, 18 pages

(56) References Cited

OTHER PUBLICATIONS

Robertson, et al., "Maize Stalk Lodging: Morphological Determinants of Stalk Strength", Mar. 3, 2017, 10 pages.
Macgowan et al. Purdue University, Corn and Soybean Crop Deprediation by Wildlife, Jun. 2006, 14 pages.
Martinez-Feria et al., Iowa State University, "Corn Grain Dry Down in Field From Maturity to Harvest", Sep. 20, 2017, 3 pages.
Wrona, "Precision Agriculture's Value" Cotton Physiology Today, vol. 9, No. 2, 1998, 8 pages.
Zhang et al., "Design of an Optical Weed Sensor Using Plant Spectral Characteristics" Sep. 2000, 12 pages.
Hunt, et al., "What Weeds Can Be Remotely Sensed?", 5 pages, May 2016.
Pepper, "Does An Adaptive Gearbox Really Learn How You Drive?", Oct. 30, 2019, 8 pages.
Eggerl, "Optimization of Combine Processes Using Expert Knowledge and Methods of Artificial Intelligence", Oct. 7, 1982, 143 pages.
Sheely et al., "Image-Based, Variable Rate Plant Growth Regulator Application in Cotton at Sheely Farms in California", Jan. 6-10, 2003 Beltwide Cotton Conferences, Nashville, TN, 17 pages.
Kovacs et al., "Physical characteristics and mechanical behaviour of maize stalks for machine development", Apr. 23, 2019, 1-pages.
Anonymously, "Optimizing Crop Profit Across Multiple Grain Attributes and Stover", ip.com, May 26, 2009, 17 pages.
Breen, "Plant Identification: Examining Leaves", Oregon State University, 2020, 8 pages.
Caglayan et al., A Plant Recognition Approach Using Shape and Color Features in Leaf Images, Sep. 2013, 11 pages.
Casady et al., "Precision Agriculture" Yield Monitors University of Missouri-System, 4 pages, 1998.
Apan et al., "Predicting Grain Protein Content in Wheat Using Hyperspectral Sensing of In-season Crop Canopies and Partial Least Squares Regression" 18 pages, 2006.
Xu et al., "Prediction of Wheat Grain Protein by Coupling Multisource Remote Sensing Imagery and ECMWF Data", Apr. 24, 2020, 21 pages.
Day, "Probability Distributions of Field Crop Yields," American Journal of Agricultural Economics, vol. 47, Issue 3, Aug. 1965, Abstract Only, 1 page.
Butzen, "Reducing Harvest Losses in Soybeans", Pioneer, Jul. 23, 2020, 3 pages.
Martin et al., "Relationship between secondary variables and soybean oil and protein concentration", Abstract Only, 1 page., 2007.
Torres, "Precision Planting of Maize" Dec. 2012, 123 pages.
Leu et al., Grazing Com Residue Using Resources and Reducing Costs, Aug. 2009, 4 pages.
"No-Till Soils", Soil Heath Brochure, 2 pages, last accessed Jul. 14, 2020.
Strickland et al., "Nitrate Toxicity in Livestock" Oklahoma State University, Feb. 2017, 2 pages.
Strickland et al., "Nitrate Toxicity in Livestock" Oklahoma State University, 8 pages, Feb. 2017.
Brownlee, "Neural Networks are Function Approximation Algorithms", Mar. 18, 2020, 13 pages.
Thompson, "Morning glory can make it impossible to harvest corn", Feb. 19, 2015, 3 pages.
Tumlison, "Monitoring Growth Development and Yield Estimation of Maize Using Very High-Resolution Uavimages in Gronau, Germany", Feb. 2017, 63 pages.
Hunt, "Mapping Weed Infestations Using Remote Sensing", 8 pages, Jul. 19, 2005.
Wright, et al., "Managing Grain Protein in Wheat Using Remote Sensing", 12 pages, 2003.
"Malting Barley in Pennsylvania", Agronomy Facts 77, 6 pages, Code EE0179 Jun. 2016.
"Green stem syndrome in soybeans", Agronomy eUpdate Issue 478 Oct. 10, 2014, 3 pages.
"Keep Weed Seed Out of Your Harvest", Aug. 8, 2019, 1 pages.

Hodrius et al., "The Impact of Multi-Sensor Data Assimilation on Plant Parameter Retrieval and Yield Estimation for Sugar Beet", The International Archives of the Photogrammetry, Remote Sensing and Spatial Information Sciences, vol. XL-7/W3, 2015, 36th International Symposium on Remote Sensing of Environment, May 11-15, 2015, Berlin, Germany, 7 pages.
Fernandez-Quintanilla et al., "Is the current state of the art of weed monitoring suitable for site-specific weed management in arable crops?", Feb. 2018, 35 pages.
Anonymously, "Improved System and Method for Controlling Agricultural Vehicle Operation Using Historical Data", Dec. 16, 2009, 8 pages.
Anonymously, "System and Method for Controlling Agricultural Vehicle Operation Using Historical Data", Jun. 30, 2009, 8 pages.
"Leafsnap, a new mobile appthat identifies plants by leaf shape, is launched by Smithsonian and collaborators", May 2, 2011, 5 pages.
Insect Gallery, Department of Entomology, Kansas State University, Oct. 19, 2020, 8 pages.
Licht, "Influence of Corn Seeding Rate, Soil Attributes, and Topographic Characteristics on Grain Yield, Yield Components, and Grain Composition", 2015, 107 pages.
"Notice of Retraction Virtual simulation of plant with individual stem based on crop growth model", Mar. 5, 2017, 7 pages.
Leland, "Who Did that? Identifying Insect Damage", Apr. 1, 2015, 4 pages
"How to improve maize protein content" https://www.yara.co.uk/crop-nutrition/forage-maize/improving-maize-protein-content, Sep. 30, 2020, 10 pages.
Hafemeister, "Weed control at harvest, combines are ideal vehicles for spreading weed seeds", Sep. 25, 2019, 3 pages.
"Harvesting Tips", Northern Pulse Growers Association, 9 pages, Jan. 31, 2001.
Wortmann et al., "Harvesting Crop Residues", Aug. 10, 2020, 8 pages.
"Harvesting", Oklahoma State University, Canola Swathing Guide, 2010, 9 pages, last accessed Jul. 14, 2020.
Hanna, "Harvest Tips for Lodged Corn", Sep. 6, 2011, 3 pages.
"Green Weeds Complicate Harvest", Crops, Slider, Sep. 26, 2012, 2 pages.
"Agrowatch Green Vegetation Index", Retrieved Dec. 11, 2020, 4 pages
"Grazing Corn Residues" (http://www.ca.uky.edu), 3 pages, Aug. 24, 2009.
Jarnevich et al., Forecasting Weed Distributions Using Climate Data: A GIS Early Warning Tool, Downloaded on Jul. 13, 2020, 12 pages.
Combine Cutting and Feeding Mechanisms in the Southeast, By J-K Park, Agricultural Research Service, U.S. Dept. of Agriculture, 1963, 1 page.
Hartzler, "Fate of weed seeds in the soil", 4 pages, Jan. 31, 2001.
Digman, "Combine Considerations for a Wet Corn Harvest", Extension SpecialistUW—Madison, 3 pages, Oct. 29, 2009.
S-Series Combine and Front End Equipment Optimization, John Deere Harvester Works, 20 pages Date: Oct. 9, 2017.
Determining yield monitoring system delay time with geostatistical and data segmentation approaches (https://www.ars.usda.gov/ARSUserFiles/50701000/cswq-0036-1 28359.pdf) Jul. 2002, 13 pages.
Precision Agriculture: Yield Monitors (dated Nov. 1998—metadata; last accessed Jul. 16, 2020) (https://extensiondata.missouri.edu/pub/pdf/envqual/wq0451.pdf) 4 pages.
Paul et al., "Effect of soil water status and strength on trafficability" (1979) (https://www.nrcresearchpress.com/doi/pdfplus/10.4141/cjss79-035), 12 pages, Apr. 23, 1979.
Sick, "Better understanding corn hybrid characteristics and properties can impact your seed decisions" (https://emergence.fbn.com/agronomy/corn-hybrid-characteristics-and-properties-impact-seed-decisions) By Steve Sick, FBN Breeding Project Lead | Sep. 21, 2018, 8 pages.
Robertson et al., "Maize Stalk Lodging: Morphological Determinants of Stalk Strength" Mar. 2017, 10 pages.

(56) References Cited

OTHER PUBLICATIONS

Martin, et al., "Breakage Susceptibility and Hardness of Corn Kernels of Various Sizes and Shapes", May 1987, 10 Pages.

* cited by examiner

CROP STATE MAP GENERATION AND CONTROL SYSTEM

FIELD OF THE DESCRIPTION

The present description relates to agricultural machines, forestry machines, construction machines and turf management machines.

BACKGROUND

There are a wide variety of different types of agricultural machines. Some agricultural machines include harvesters, such as combine harvesters, sugar cane harvesters, cotton harvesters, self-propelled forage harvesters, and windrowers. Some harvester can also be fitted with different types of headers to harvest different types of crops.

Agricultural harvesters may operate differently in areas of a field containing downed crop. Downed crop refers to crop plants that have their stalks bent or broken, for example due to wind, rain, hail, or the like. These forces bend or break the stalks the crop plants and cause the plants to have a bent-over and non-vertical orientation. Crop state is an agricultural characteristic indicative of whether a crop plant is standing, down, partially down, stubble, or missing and, if the crop is downed, the compass orientation and magnitude of the downing.

The discussion above is merely provided for general background information and is not intended to be used as an aid in determining the scope of the claimed subject matter.

SUMMARY

A prior vegetative index map, seeding characteristic map, predictive yield map, or predictive biomass map is obtained by an agricultural harvester and shows one of vegetative index, seeding characteristic, predictive yield, or predictive biomass values at different geographic locations of a field and may be particularly useful during harvesting of the field. An in-situ sensor on the agricultural harvester senses a characteristic that has values indicative of the crop state proximate the agricultural harvester as the agricultural harvester moves through the field. A predictive map generator generates a functional predictive map that predicts crop state at different locations in the field based on a relationship between the values in the vegetative index, seeding characteristic, predictive yield, or predictive biomass map and the crop state characteristic sensed by the in-situ sensor. The functional predictive crop state map can be output and used in automated machine control.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to examples that solve any or all disadvantages noted in the background.

DETAILED DESCRIPTION

Figure 1:
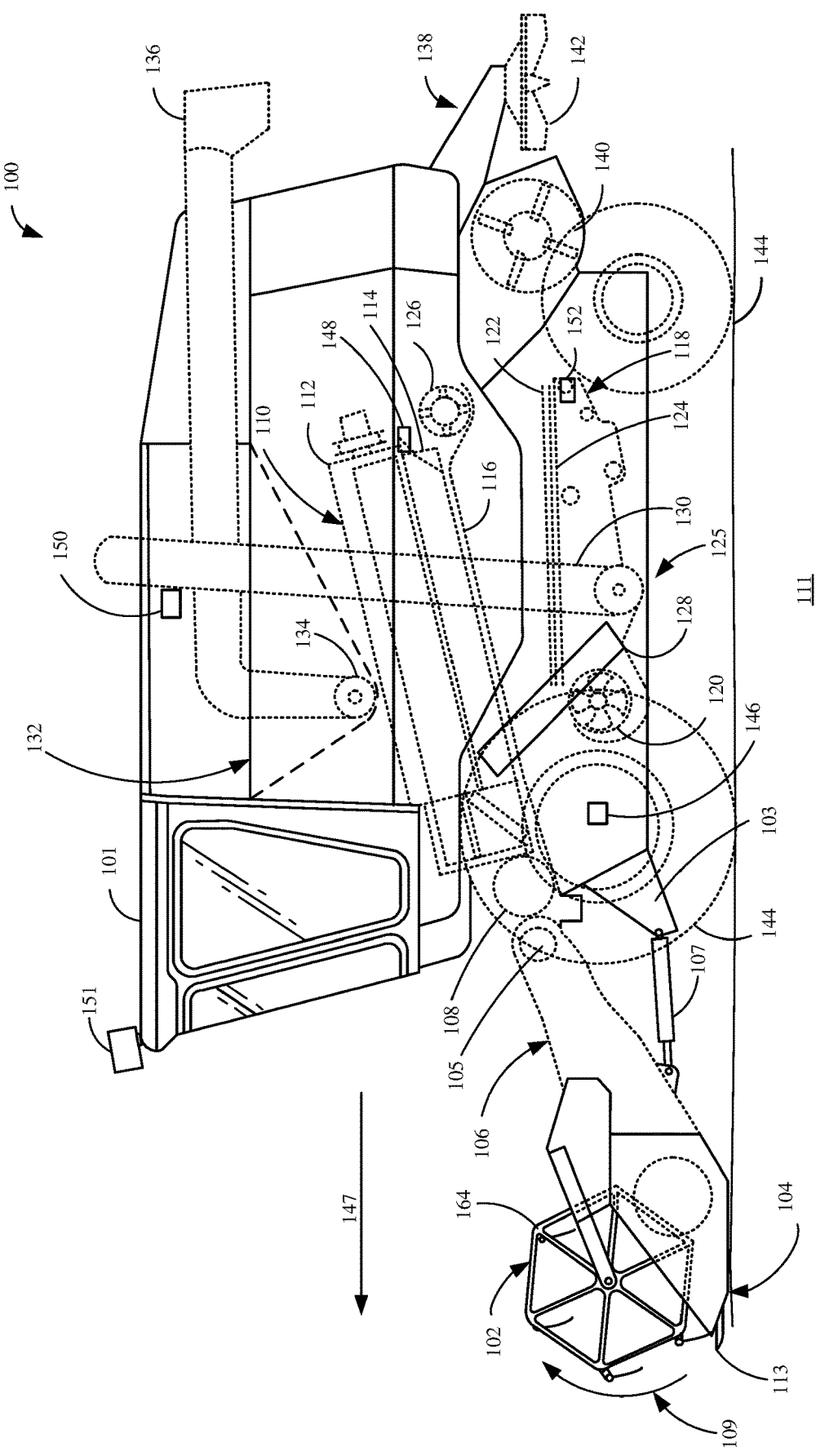
FIG. 1 is a partial pictorial, partial schematic illustration of one example of an agricultural harvester.

For the purposes of promoting an understanding of the principles of the present disclosure, reference will now be made to the examples illustrated in the drawings, and specific language will be used to describe the same. It will nevertheless be understood that no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, and/or steps described with respect to one example may be combined with the features, components, and/or steps described with respect to other examples of the present disclosure.

The present description relates to using in-situ data taken concurrently with an agricultural operation, in combination with prior data, to generate a functional predictive map and, more particularly, a functional predictive crop state map. In some examples, the functional predictive crop state map can be used to control an agricultural work machine, such as an agricultural harvester. Performance of an agricultural harvester may be degraded when the agricultural harvester engages areas of varying crop state unless machine settings are also changed. For instance, in an area of downed crop the agricultural harvester may travel more slowly through the field to prevent grain loss. Or for instance, in an area of down crop, it may be beneficial to direct the agricultural harvester along a path such that the agricultural harvester harvests in a direction opposite the direction the crop is leaning of the down crop. That is, a course of the agricultural harvester is selected so as to drive the agricultural harvester into the crop plants from the opposite direction the plants are downed, such that the harvester reaches the top of the plant first. Or, for instance, in an area of down crop, it may be beneficial to adjust header height or reel positions.

A vegetative index map illustratively maps vegetative index values (which may be indicative of vegetative growth) across different geographic locations in a field of interest. One example of a vegetative index includes a normalized difference vegetation index (NDVI). There are many other vegetative indices, and these other vegetative indices are within the scope of the present disclosure. In some examples, a vegetative index may be derived from sensor readings of one or more bands of electromagnetic radiation reflected by plants. Without limitations, these bands may be in the microwave, infrared, visible, or ultraviolet portions of the electromagnetic spectrum.

A vegetative index map can thus be used to identify the presence and location of vegetation. In some examples, a vegetative index map enables crops to be identified and georeferenced in the presence of bare soil, crop residue, or other plants, including crop or weeds. For instance, towards the beginning of a growing season, when a crop is in a growing state, the vegetative index may show the progress of the crop development. Therefore, if a vegetative index map is generated early in the growing season or midway through the growing season, the vegetative index map may be indicative of the progress of the development of the crop plants. For instance, the vegetative index map may indicate whether the plant is stunted, whether a sufficient canopy is being established, or whether other plant attributes indicative of plant development are present. A vegetative index map can also be indicative of other vegetative characteristics as well such as plant health.

A seeding characteristic map illustratively maps seed locations across different geographic locations in one or more field of interest. These seed maps are typically collected from past seed planting operations. In some examples, the seeding characteristic map may be derived from control signals used by a seeder when planting the seeds or from sensor signals generated by sensors on the seeder that confirm a seed was planted. Seeders can include geographic position sensors that geolocate the locations of where the seeds were planted. This information can be used to determine the seed planting density which correlates to a plant density. Plant density can affect how resistant crop plants are to downing by wind, for example. A seeding characteristic map can also contain other information as well, such as characteristics of the seed used. For example, some characteristics include seed type, genetic stalk strength, genetic green snap susceptibility, seed brand, seed coating, planting date, gemination period, typical growth stage periods, mature plant height, and seed genotype The present discussion also includes predictive maps that predict a characteristic based on an information map and a relationship to sensed data obtained from an in-situ sensor. These predictive maps include a predictive yield map and a predictive biomass map. In one example, the predictive yield map is generated by receiving a prior vegetative index map and sensed yield data obtained from an in-situ yield sensor and determining a relationship between the prior vegetative index map and the sensed yield data obtained from a signal from the in-situ yield sensor, and using the relationship to generate the predictive yield map based on the relationship and the prior vegetative index map. In one example, the predictive biomass map is generated by receiving a prior vegetative index map and sensing a biomass and determining a relationship between the prior vegetative index map and the sensed biomass obtained from a data signal from a biomass sensor, and using the relationship to generate the predictive biomass map based on the relationship and the prior vegetative index map. The predictive yield and biomass maps can be created based on other information maps or generated in other ways as well. For example, the predictive yield or biomass maps can be generated based on satellite images, growth models, weather models, etc. Or for example, a predictive yield map or a predictive biomass map may be based in whole or in part on a topographic map, a soil type map, a soil constituent map, or a soil health map.

The present discussion thus proceeds with respect to examples in which a system receives one or more of a vegetative index, seeding, predictive yield, or predictive biomass map and uses an in-situ sensor that detects a variable indicative of crop state during a harvesting operation. The system generates a model that models a relationship between the vegetative index values, seed characteristic values, predictive yield values, or predictive biomass values from the one or more received maps and in-situ data from the in-situ sensor that represents the variable indicative of crop state. The model is used to generate a functional predictive crop state map that predicts an anticipated crop state in the field. The functional predictive crop state map, generated during the harvesting operation, can be presented to an operator or other user, used in automatically controlling an agricultural harvester during the harvesting operation, or both.

FIG. 1 is a partial pictorial, partial schematic, illustration of a self-propelled agricultural harvester 100. In the illustrated example, agricultural harvester 100 is a combine harvester. Further, although combine harvesters are provided as examples throughout the present disclosure, it will be appreciated that the present description is also applicable to other types of harvesters, such as cotton harvesters, sugarcane harvesters, self-propelled forage harvesters, windrowers, or other agricultural work machines. Consequently, the present disclosure is intended to encompass the various types of harvesters described and is, thus, not limited to combine harvesters. Moreover, the present disclosure is directed to other types of work machines, such as agricultural seeders and sprayers, construction equipment, forestry equipment, and turf management equipment where generation of a predictive map may be applicable. Consequently, the present disclosure is intended to encompass these various types of harvesters and other work machines and is, thus, not limited to combine harvesters.

As shown in FIG. 1, agricultural harvester 100 illustratively includes an operator compartment 101, which can have a variety of different operator interface mechanisms, for controlling agricultural harvester 100. Agricultural harvester 100 includes front-end equipment, such as a header 102, and a cutter generally indicated at 104. Agricultural harvester 100 also includes a feeder house 106, a feed accelerator 108, and a thresher generally indicated at 110. The feeder house 106 and the feed accelerator 108 form part of a material handling subsystem 125. Header 102 is pivotally coupled to a frame 103 of agricultural harvester 100 along pivot axis 105. One or more actuators 107 drive movement of header 102 about axis 105 in the direction generally indicated by arrow 109. Thus, a vertical position of header 102 (the header height) above ground 111 over which the header 102 travels is controllable by actuating actuator 107. While not shown in FIG. 1, agricultural harvester 100 may also include one or more actuators that operate to apply a tilt angle, a roll angle, or both to the header 102 or portions of header 102. Tilt refers to an angle at which the cutter 104 engages the crop. The tilt angle is increased, for example, by controlling header 102 to point a distal edge 113 of cutter 104 more toward the ground. The tilt angle is decreased by controlling header 102 to point the distal edge 113 of cutter 104 more away from the ground. The roll angle refers to the orientation of header 102 about the front-to-back longitudinal axis of agricultural harvester 100.

Thresher 110 illustratively includes a threshing rotor 112 and a set of concaves 114. Further, agricultural harvester 100 also includes a separator 116. Agricultural harvester 100 also includes a cleaning subsystem or cleaning shoe (collectively referred to as cleaning subsystem 118) that includes a cleaning fan 120, chaffer 122, and sieve 124. The material handling subsystem 125 also includes discharge beater 126, tailings elevator 128, clean grain elevator 130, as well as unloading auger 134 and spout 136. The clean grain elevator moves clean grain into clean grain tank 132. Agricultural harvester 100 also includes a residue subsystem 138 that can include chopper 140 and spreader 142. Agricultural harvester 100 also includes a propulsion subsystem that includes an engine that drives ground engaging components 144, such as wheels or tracks. In some examples, a combine harvester within the scope of the present disclosure may have more than one of any of the subsystems mentioned above. In some examples, agricultural harvester 100 may have left and right cleaning subsystems, separators, etc., which are not shown in FIG. 1.

In operation, and by way of overview, agricultural harvester 100 illustratively moves through a field in the direction indicated by arrow 147. As agricultural harvester 100 moves, header 102 (and the associated reel 164) engages the crop to be harvested and gathers the crop toward cutter 104. An operator of agricultural harvester 100 can be a local human operator, a remote human operator, or an automated system. The operator of agricultural harvester 100 may determine one or more of a height setting, a tilt angle setting, or a roll angle setting for header 102. For example, the operator inputs a setting or settings to a control system, described in more detail below, that controls actuator 107. The control system may also receive a setting from the operator for establishing the tilt angle and roll angle of the header 102 and implement the inputted settings by controlling associated actuators, not shown, that operate to change the tilt angle and roll angle of the header 102. The actuator 107 maintains header 102 at a height above ground 111 based on a height setting and, where applicable, at desired tilt and roll angles. Each of the height, roll, and tilt settings may be implemented independently of the others. The control system responds to header error (e.g., the difference between the height setting and measured height of header 102 above ground 111 and, in some examples, tilt angle and roll angle errors) with a responsiveness that is determined based on a selected sensitivity level. If the sensitivity level is set at a greater level of sensitivity, the control system responds to smaller header position errors, and attempts to reduce the detected errors more quickly than when the sensitivity is at a lower level of sensitivity.

Returning to the description of the operation of agricultural harvester 100, after crops are cut by cutter 104, the severed crop material is moved through a conveyor in feeder house 106 toward feed accelerator 108, which accelerates the crop material into thresher 110. The crop material is threshed by rotor 112 rotating the crop against concaves 114. The threshed crop material is moved by a separator rotor in separator 116 where a portion of the residue is moved by discharge beater 126 toward the residue subsystem 138. The portion of residue transferred to the residue subsystem 138 is chopped by residue chopper 140 and spread on the field by spreader 142. In other configurations, the residue is released from the agricultural harvester 100 in a windrow. In other examples, the residue subsystem 138 can include weed seed eliminators (not shown) such as seed baggers or other seed collectors, or seed crushers or other seed destroyers.

Grain falls to cleaning subsystem 118. Chaffer 122 separates some larger pieces of material from the grain, and sieve 124 separates some of finer pieces of material from the clean grain. Clean grain falls to an auger that moves the grain to an inlet end of clean grain elevator 130, and the clean grain elevator 130 moves the clean grain upwards, depositing the clean grain in clean grain tank 132. Residue is removed from the cleaning subsystem 118 by airflow generated by cleaning fan 120. Cleaning fan 120 directs air along an airflow path upwardly through the sieves and chaffers. The airflow carries residue rearwardly in agricultural harvester 100 toward the residue handling subsystem 138.

Tailings elevator 128 returns tailings to thresher 110 where the tailings are re-threshed. Alternatively, the tailings also may be passed to a separate re-threshing mechanism by a tailings elevator or another transport device where the tailings are re-threshed as well.

FIG. 1 also shows that, in one example, agricultural harvester 100 includes ground speed sensor 146, one or more separator loss sensors 148, a clean grain camera 150, a forward looking image capture mechanism 151, which may be in the form of a stereo or mono camera, and one or more loss sensors 152 provided in the cleaning subsystem 118.

Ground speed sensor 146 senses the travel speed of agricultural harvester 100 over the ground. Ground speed sensor 146 may sense the travel speed of the agricultural harvester 100 by sensing the speed of rotation of the ground engaging components (such as wheels or tracks), a drive shaft, an axel, or other components. In some instances, the travel speed may be sensed using a positioning system, such as a global positioning system (GPS), a dead reckoning system, a long range navigation (LORAN) system, or a wide variety of other systems or sensors that provide an indication of travel speed.

Loss sensors 152 illustratively provide an output signal indicative of the quantity of grain loss occurring in both the right and left sides of the cleaning subsystem 118. In some examples, sensors 152 are strike sensors which count grain strikes per unit of time or per unit of distance traveled to provide an indication of the grain loss occurring at the cleaning subsystem 118. The strike sensors for the right and left sides of the cleaning subsystem 118 may provide individual signals or a combined or aggregated signal. In some examples, sensors 152 may include a single sensor as opposed to separate sensors provided for each cleaning subsystem 118. Separator loss sensor 148 provides a signal indicative of grain loss in the left and right separators, not separately shown in FIG. 1. The separator loss sensors 148 may be associated with the left and right separators and may provide separate grain loss signals or a combined or aggregate signal. In some instances, sensing grain loss in the separators may also be performed using a wide variety of different types of sensors as well.

Agricultural harvester 100 may also include other sensors and measurement mechanisms. For instance, agricultural harvester 100 may include one or more of the following sensors: a header height sensor that senses a height of header 102 above ground 111; stability sensors that sense oscillation or bouncing motion (and amplitude) of agricultural harvester 100; a residue setting sensor that is configured to sense whether agricultural harvester 100 is configured to chop the residue, produce a windrow, etc.; a cleaning shoe fan speed sensor to sense the speed of cleaning fan 120; a concave clearance sensor that senses clearance between the rotor 112 and concaves 114; a threshing rotor speed sensor that senses a rotor speed of rotor 112; a chaffer clearance sensor that senses the size of openings in chaffer 122; a sieve clearance sensor that senses the size of openings in sieve 124; a material other than grain (MOG) moisture sensor that senses a moisture level of the MOG passing through agricultural harvester 100; one or more machine setting sensors configured to sense various configurable settings of agricultural harvester 100; a machine orientation sensor that senses the orientation of agricultural harvester 100; and crop property sensors that sense a variety of different types of crop properties, such as crop type, crop moisture, and other crop properties. Crop property sensors may also be configured to sense characteristics of the severed crop material as the crop material is being processed by agricultural harvester 100. For example, in some instances, the crop property sensors may sense grain quality such as broken grain, MOG levels; grain constituents such as starches and protein; and grain feed rate as the grain travels through the feeder house 106, clean grain elevator 130, or elsewhere in the agricultural harvester 100. The crop property sensors may also sense the feed rate of biomass through feeder house 106, through the separator 116 or elsewhere in agricultural harvester 100. The crop property sensors may also sense the feed rate as a mass flow rate of grain through elevator 130 or through other portions of the agricultural harvester 100 or provide other output signals indicative of other sensed variables. Crop property sensors can include one or more crop state sensors that sense crop state being harvested by agricultural harvester.

Crop state sensors can include a mono-camera or multi-camera system that captures one or more images of crop plants. For example, forward looking image capture mechanism 151 may form a crop state sensor that senses the crop state of crop plants in front of agricultural harvester 100. In another example, a crop state sensor can be placed on agricultural harvester 100 and view in one or more directions other than in front of agricultural harvester 100. Images captured by the crop state sensor can be analyzed to determine whether the crop is standing, has some magnitude of a down condition, is stubble, or is missing. Then, if the crop has some magnitude of a downed condition, then the image can be analyzed to determine the orientation of the downed crop. Some orientations can be relative to agricultural harvester 100, such as, but not limited to "sideways", "towards the machine", "away from the machine", or "random orientations." Some orientations can be absolute (e.g., relative to the earth) such as a numerical compass heading or numeric deviation from gravimetric or surface vertical in degrees. For example, in some instances, the orientation may be provided as a heading relative to magnetic north, relative to true north, relative to a crop row, relative to a harvester heading, or relative to other references.

In another example, a crop state sensor includes a range scanning device, such as, but not limited to radar, lidar, or sonar. A range scanning device can be used to sense the height of the crop. Crop height, while indicative of other things, can also indicate downed crop, the magnitude of a downed crop condition, or an orientation of the downed crop.

Prior to describing how agricultural harvester 100 generates a functional predictive crop state map and uses the functional predictive crop state map for presentation or control, a brief description of some of the items on agricultural harvester 100, and their respective operations, will first be described. The description of FIGS. 2 and 3 describe receiving a general type of information map and combining information from the information map with a georeferenced sensor signal generated by an in-situ sensor, where the sensor signal is indicative of a characteristic in the field, such as characteristics of crop or weeds present in the field. Characteristics of the field may include, but are not limited to, characteristics of a field such as slope, weed intensity, weed type, soil moisture, surface quality; characteristics of crop properties such as crop height, crop moisture, crop density, crop state; characteristics of grain properties such as grain moisture, grain size, grain test weight; and characteristics of machine performance such as loss levels, job quality, fuel consumption, and power utilization. A relationship between the characteristic values obtained from in-situ sensor signals and the information map values is identified, and that relationship is used to generate a new functional predictive map. A functional predictive map predicts values at different geographic locations in a field, and one or more of those values may be used for controlling a machine, such as one or more subsystems of an agricultural harvester. In some instances, a functional predictive map can be presented to a user, such as an operator of an agricultural work machine, which may be an agricultural harvester. A functional predictive map may be presented to a user visually, such as via a display, haptically, or audibly. The user may interact with the functional predictive map to perform editing operations and other user interface operations. In some instances, a functional predictive map can be used for one or more of controlling an agricultural work machine, such as an agricultural harvester, presentation to an operator or other user, and presentation to an operator or user for interaction by the operator or user.

Figure 2:
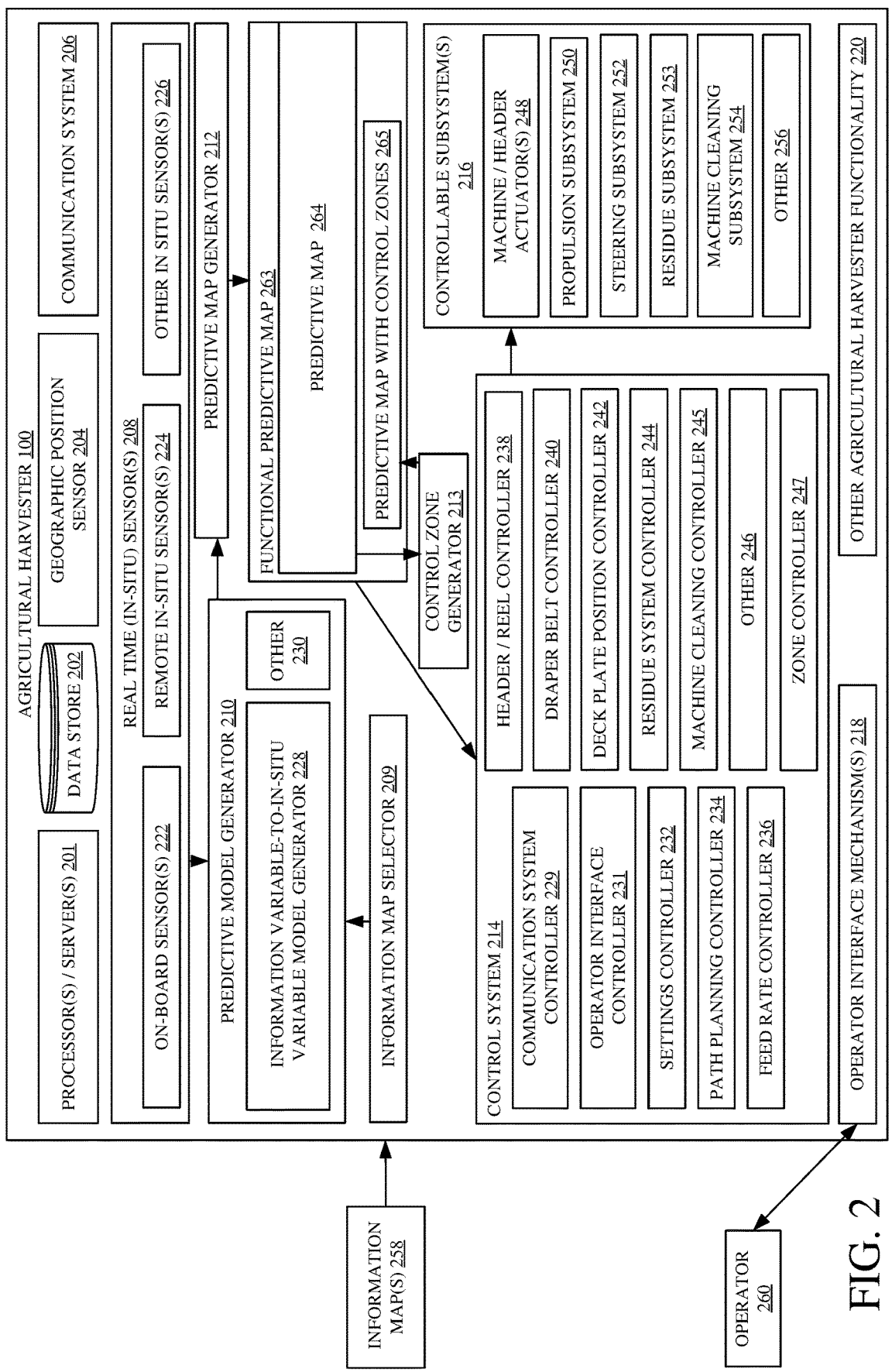
FIG. 2 is a block diagram showing some portions of an agricultural harvester in more detail, according to some examples of the present disclosure.
Figure 3A:
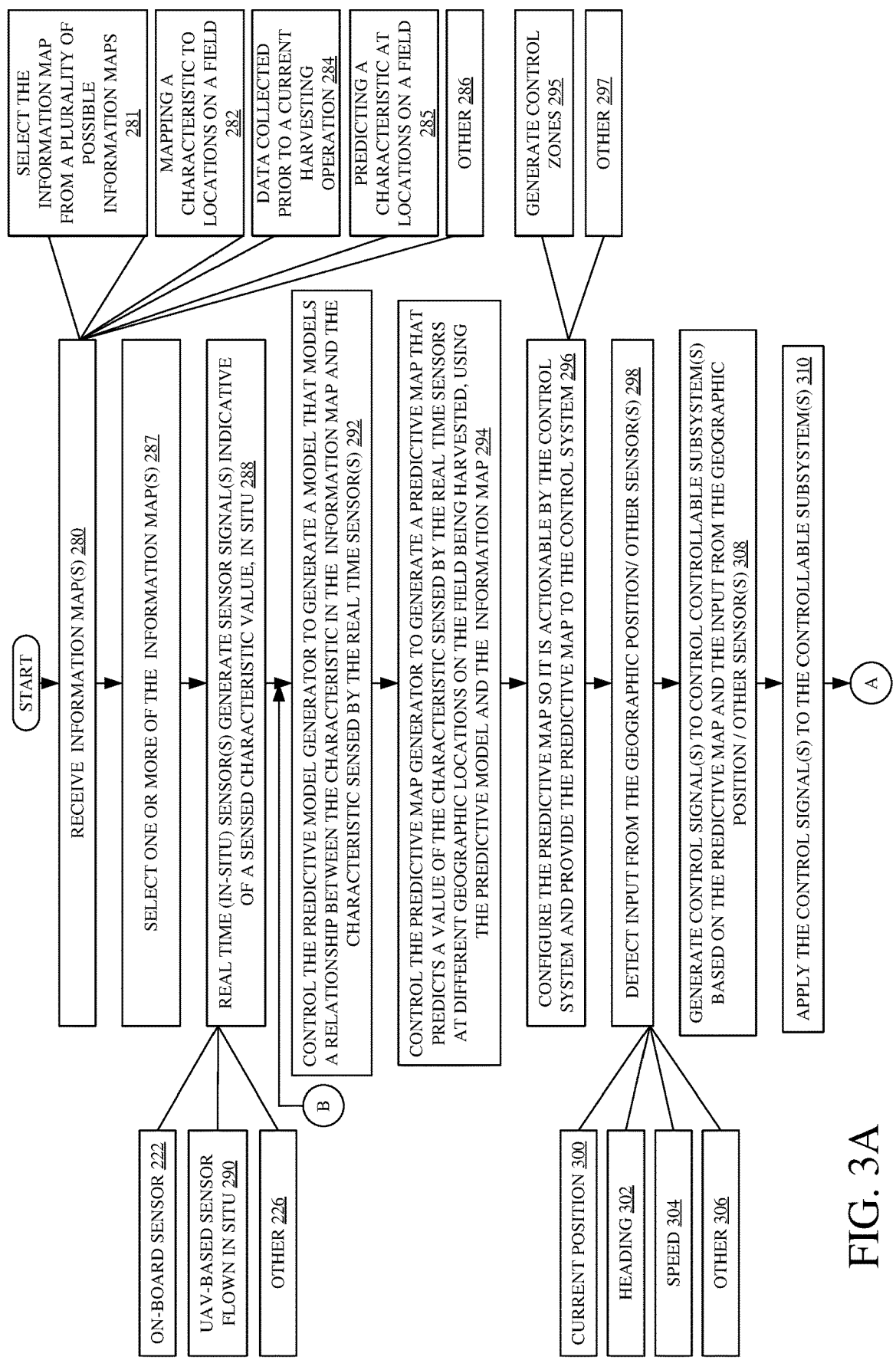
FIGS. 3A-3B (collectively referred to herein as FIG. 3) show a flow diagram illustrating an example of operation of an agricultural harvester in generating a map.
Figure 3B:
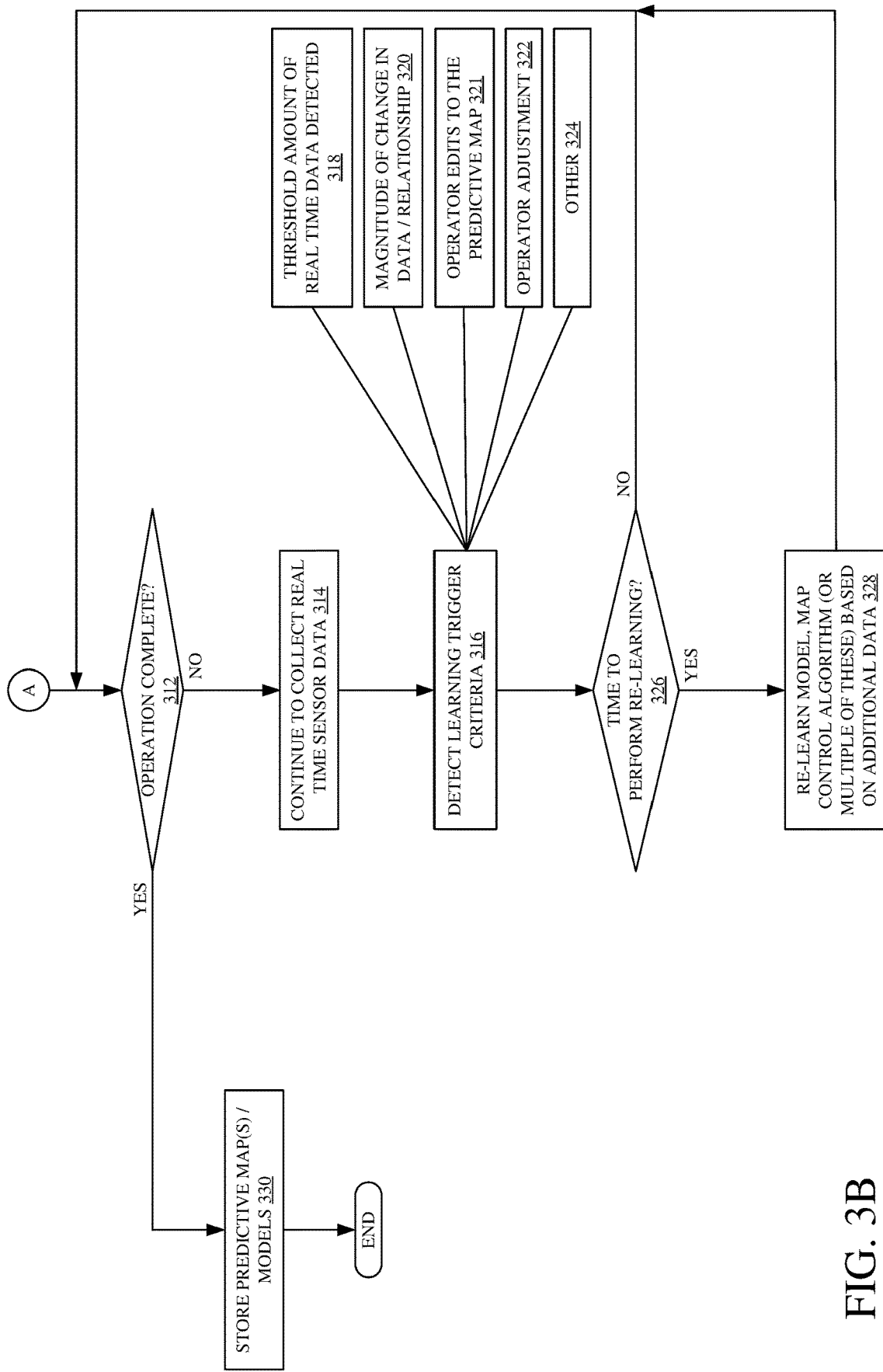
Figure 4:
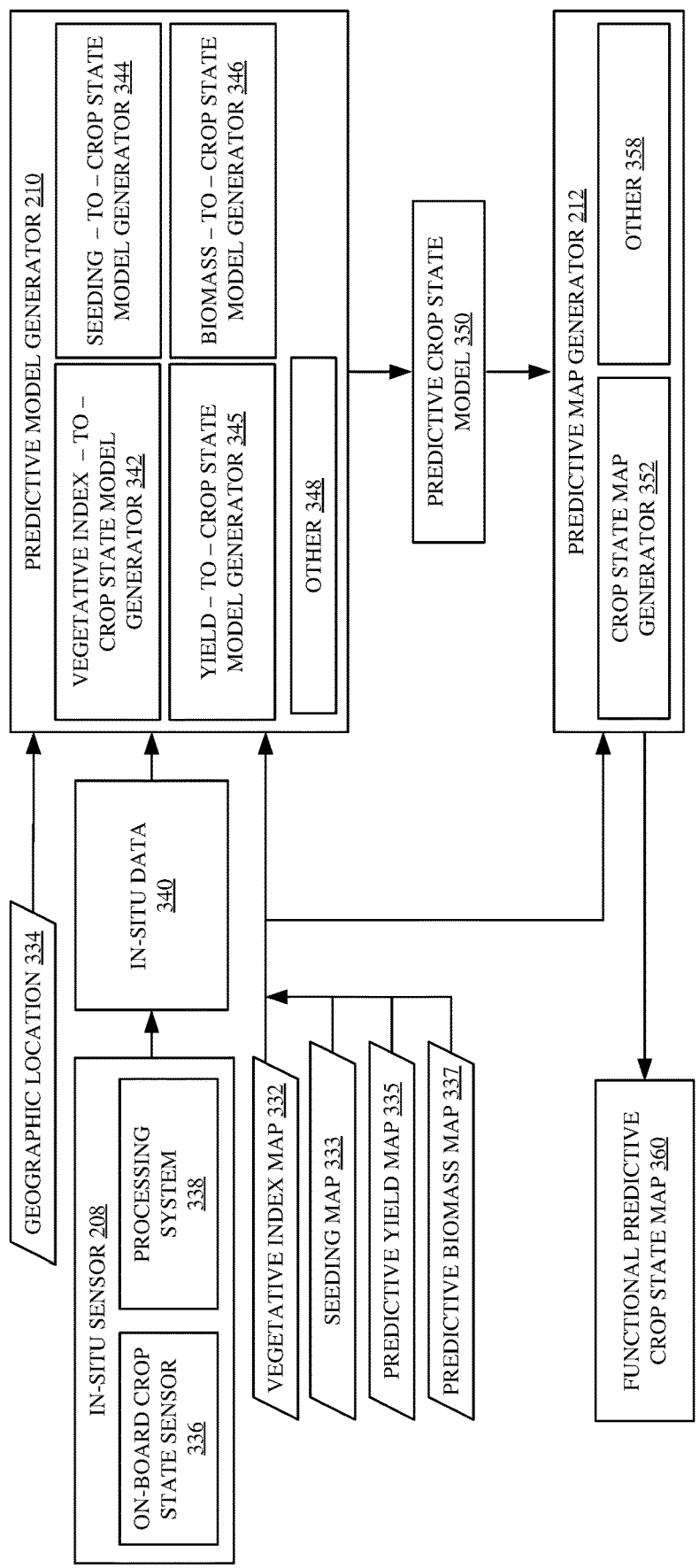
FIG. 4 is a block diagram showing one example of a predictive model generator and a predictive map generator.
Figure 5:
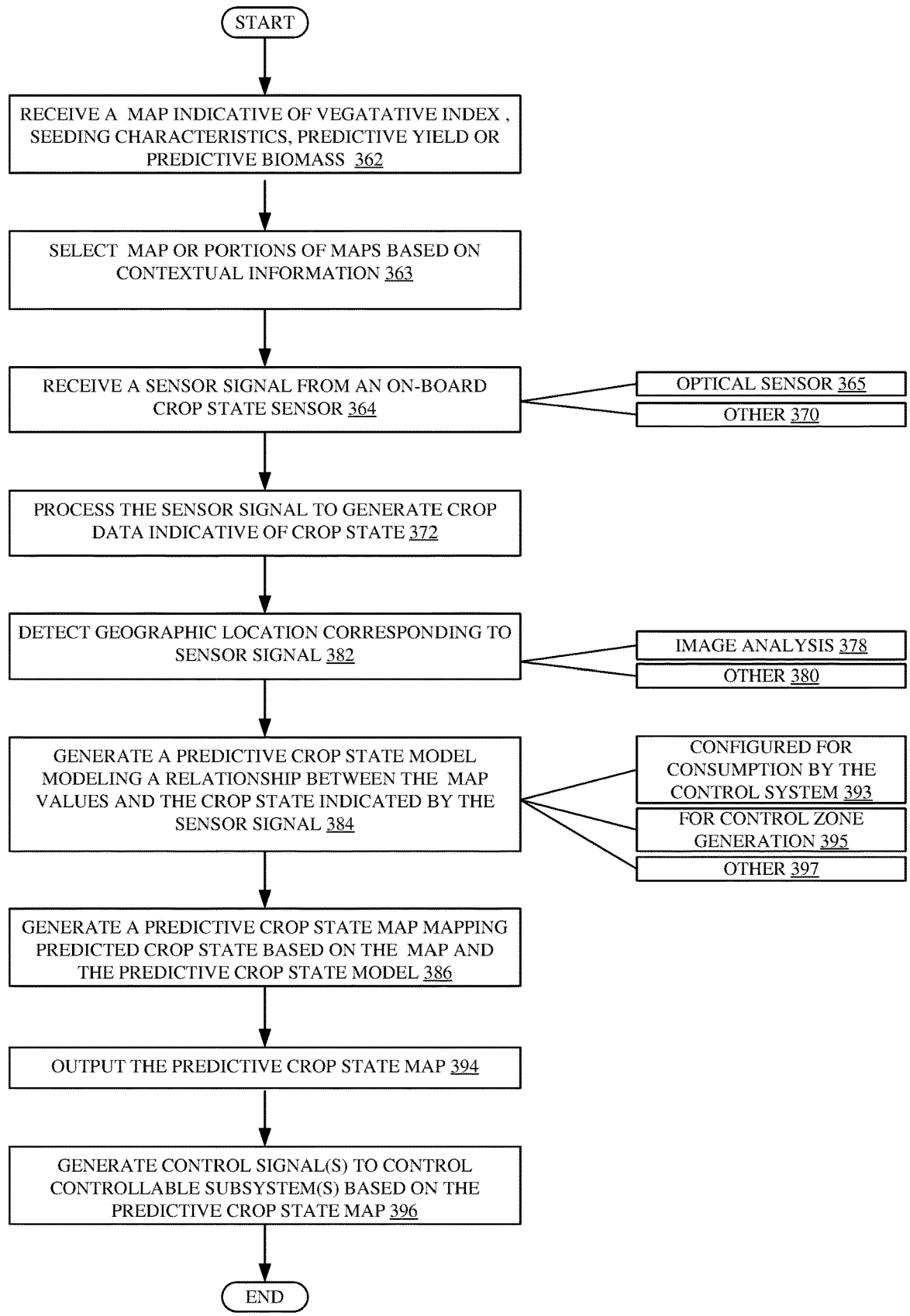
FIG. 5 is a flow diagram showing an example of operation of an agricultural harvester in receiving a vegetative index, seeding characteristic, predictive yield, or predictive biomass map; detecting an in-situ crop state characteristic; and generating a functional predictive crop state map for presentation or use in controlling the agricultural harvester during a harvesting operation or both.

After a general approach is described with respect to FIGS. 2 and 3, a more specific approach for generating a functional predictive crop state map that can be presented to an operator or user, or used to control agricultural harvester 100, or both is described with respect to FIGS. 4 and 5. Again, while the present discussion proceeds with respect to the agricultural harvester and, particularly, a combine harvester, the scope of the present disclosure encompasses other types of agricultural harvesters or other agricultural work machines.

FIG. 2 is a block diagram showing some portions of an example agricultural harvester 100. FIG. 2 shows that agricultural harvester 100 illustratively includes one or more processors or servers 201, data store 202, geographic position sensor 204, communication system 206, and one or more in-situ sensors 208 that sense one or more agricultural characteristics of a field concurrent with a harvesting operation. An agricultural characteristic can include any characteristic that can have an effect of the harvesting operation. Some examples of agricultural characteristics include characteristics of the harvesting machine, the field, the plants on the field, and the weather. Other types of agricultural characteristics are also included. The in-situ sensors 208 generate values corresponding to the sensed characteristics. The agricultural harvester 100 also includes a predictive model or relationship generator (collectively referred to hereinafter as "predictive model generator 210"), predictive map generator 212, control zone generator 213, control system 214, one or more controllable subsystems 216, and an operator interface mechanism 218. The agricultural harvester 100 can also include a wide variety of other agricultural harvester functionality 220. The in-situ sensors 208 include, for example, on-board sensors 222, remote sensors 224, and other sensors 226 that sense characteristics of a field during the course of an agricultural operation. Predictive model generator 210 illustratively includes an information variable-to-in-situ variable model generator 228, and predictive model generator 210 can include other items 230. Control system 214 includes communication system controller 229, operator interface controller 231, a settings controller 232, path planning controller 234, feed rate controller 236, header and reel controller 238, draper belt controller 240, deck plate position controller 242, residue system controller 244, machine cleaning controller 245, zone controller 247, and control system 214 can include other items 246. Controllable subsystems 216 include machine and header actuators 248, propulsion subsystem 250, steering subsystem 252, residue subsystem 138, machine cleaning subsystem 254, and controllable subsystems 216 can include a wide variety of other subsystems 256.

FIG. 2 also shows that agricultural harvester 100 can receive one or more information maps 258. As described below, an information map 258 includes, for example, a vegetative index, seeding characteristic, predictive yield, or predictive biomass map. However, information map 258 may also encompass other types of data that were obtained prior to a harvesting operation, such as contextual information. Contextual information can include, without limitation, one or more of weather conditions over part of or all of a growing season, presence of pests, geographic location, soil types, irrigation, treatment application, etc. Weather conditions can include, without limitation, precipitation over the season, presence of hail capable of crop damage, presence of high winds, direction of high winds, temperature over the season, etc. Some examples of pests broadly include, insects, fungi, weeds, bacteria, viruses, etc. Some examples of treatment applications include herbicide, pesticide, fungicide, fertilizer, mineral supplements, etc. FIG. 2 also shows that an operator 260 may operate the agricultural harvester 100. The operator 260 interacts with operator interface mechanisms 218. In some examples, operator interface mechanisms 218 may include joysticks, levers, a steering wheel, linkages, pedals, buttons, dials, keypads, user actuatable elements (such as icons, buttons, etc.) on a user interface display device, a microphone and speaker (where speech recognition and speech synthesis are provided), among a wide variety of other types of control devices. Where a touch sensitive display system is provided, operator 260 may interact with operator interface mechanisms 218 using touch gestures. These examples described above are provided as illustrative examples and are not intended to limit the scope of the present disclosure. Consequently, other types of operator interface mechanisms 218 may be used and are within the scope of the present disclosure.

Information map 258 may be downloaded onto agricultural harvester 100 and stored in data store 202, using communication system 206 or in other ways. In some examples, communication system 206 may be a cellular communication system, a system for communicating over a wide area network or a local area network, a system for communicating over a near field communication network, or a communication system configured to communicate over any of a variety of other networks or combinations of networks. Communication system 206 may also include a system that facilitates downloads or transfers of information to and from a secure digital (SD) card or a universal serial bus (USB) card, or both.

Geographic position sensor 204 illustratively senses or detects the geographic position or location of agricultural harvester 100. Geographic position sensor 204 can include, but is not limited to, a global navigation satellite system (GNSS) receiver that receives signals from a GNSS satellite transmitter. Geographic position sensor 204 can also include a real-time kinematic (RTK) component that is configured to enhance the precision of position data derived from the GNSS signal. Geographic position sensor 204 can include a dead reckoning system, a cellular triangulation system, or any of a variety of other geographic position sensors.

In-situ sensors 208 may be any of the sensors described above with respect to FIG. 1. In-situ sensors 208 include on-board sensors 222 that are mounted on-board agricultural harvester 100. Such sensors may include, for instance, a perception, image, or optical sensor, such as, a forward looking mono or stereo camera system and image processing system or cameras mounted to view crop plants proximate to agricultural harvester 100 other than forward of agricultural harvester 100. The in-situ sensors 208 may also include remote in-situ sensors 224 that capture in-situ information. In-situ data include data taken from a sensor on-board the agricultural harvester or taken by any sensor where the data are detected during the harvesting operation.

Predictive model generator 210 generates a model that is indicative of a relationship between the values sensed by the in-situ sensor 208 and a characteristic mapped to the field by the information map 258. For example, if the information map 258 maps a vegetative index value to different locations in the field and the in-situ sensor 208 is sensing a value indicative of crop state, then information variable-to-in-situ variable model generator 228 generates a predictive crop state model that models the relationship between the vegetative index values and the crop state values. Predictive map generator 212 uses the predictive crop state model generated by predictive model generator 210 to generate a functional predictive crop state map that predicts the value of crop state, at different locations in the field based upon the information map 258. Predictive map generator 212 can use the vegetative index values in information map 258 and the model generated by predictive model generator 210 to generate a functional predictive map 263 that predicts the crop state at different locations in the field. Predictive map generator 212 thus outputs predictive map 264.

Or for example, if the information map 258 maps a seeding characteristic to different locations in the field and the in-situ sensor 208 is sensing a value indicative of crop state, then information variable-to-in-situ variable model generator 228 generates a predictive crop state model that models the relationship between the seeding characteristics (with or without contextual information) and the in-situ crop state values. Predictive map generator 212 uses the predictive crop state model generated by predictive model generator 210 to generate a functional predictive crop state map that predicts the value of crop state that will be sensed by the in-situ sensors 208, at different locations in the field based upon the information map 258. Predictive map generator 212 can use the seeding characteristic values in information map 258 and the model generated by predictive model generator 210 to generate a functional predictive map 263 that predicts the crop state at different locations in the field. Predictive map generator 212 thus outputs predictive map 264.

In some examples, the type of data in the functional predictive map 263 may be the same as the in-situ data type sensed by the in-situ sensors 208. In some instances, the type of data in the functional predictive map 263 may have different units from the data sensed by the in-situ sensors 208. In some examples, the type of data in the functional predictive map 263 may be different from the data type sensed by the in-situ sensors 208 but has a relationship to data type sensed by the in-situ sensors 208. For example, in some examples, the in-situ data type may be indicative of the type of data in the functional predictive map 263. In some examples, the type of data in the functional predictive map 263 may be different than the data type in the information map 258. In some instances, the type of data in the functional predictive map 263 may have different units from the data in the information map 258. In some examples, the type of data in the functional predictive map 263 may be different from the data type in the information map 258 but has a relationship to the data type in the information map 258. For example, in some examples, the data type in the information map 258 may be indicative of the type of data in the functional predictive map 263. In some examples, the type of data in the functional predictive map 263 is different than one of, or both of the in-situ data type sensed by the in-situ sensors 208 and the data type in the information map 258. In some examples, the type of data in the functional predictive map 263 is the same as one of, or both of, of the in-situ data type sensed by the in-situ sensors 208 and the data type in information map 258. In some examples, the type of data in the functional predictive map 263 is the same as one of the in-situ data type sensed by the in-situ sensors 208 or the data type in the information map 258, and different than the other.

As shown in FIG. 2, predictive map 264 predicts the value of a characteristic sensed by in-situ sensors 208, or a characteristic related to the characteristic sensed by in-situ sensors 208 at various locations across the field based upon an information value in information map 258 at those locations (or locations with similar contextual information) and using the predictive model 350. For example, if predictive model generator 210 has generated a predictive model indicative of a relationship between a vegetative index value and crop state, then, given the vegetative index value at different locations across the field, predictive map generator 212 generates a predictive map 264 that predicts the value of the crop state at different locations across the field. The vegetative index value at those locations obtained from the information map 258 and the relationship between vegetative index value and crop state obtained from the predictive model 350 are used to generate the predictive map 264.

Some variations in the data types that are mapped in the information map 258, the data types sensed by in-situ sensors 208 and the data types predicted on the predictive map 264 will now be described.

In some examples, the data type in the information map 258 is different from the data type sensed by in-situ sensors 208, yet the data type in the predictive map 264 is the same as the data type sensed by the in-situ sensors 208. For instance, the information map 258 may be a vegetative index map, and the variable sensed by the in-situ sensors 208 may be crop state. The predictive map 264 may then be a predictive crop state map that maps predicted crop state values to different geographic locations in the field. In another example, the information map 258 may be a vegetative index map, and the variable sensed by the in-situ sensors 208 may be crop height. The predictive map 264 may then be a predictive crop height map that maps predicted crop height values to different geographic locations in the field.

Also, in some examples, the data type in the information map 258 is different from the data type sensed by in-situ sensors 208, and the data type in the predictive map 264 is different from both the data type in the information map 258 and the data type sensed by the in-situ sensors 208. For instance, the information map 258 may be a vegetative index map, and the variable sensed by the in-situ sensors 208 may be crop height. The predictive map 264 may then be a predictive biomass map that maps predicted biomass values to different geographic locations in the field. In another example, the information map 258 may be a vegetative index map, and the variable sensed by the in-situ sensors 208 may be crop state. The predictive map 264 may then be a predictive speed map that maps predicted harvester speed values to different geographic locations in the field.

In some examples, the information map 258 is from a prior pass through the field during a prior operation and the data type is different from the data type sensed by in-situ sensors 208, yet the data type in the predictive map 264 is the same as the data type sensed by the in-situ sensors 208. For instance, the information map 258 may be a seed population map generated during planting, and the variable sensed by the in-situ sensors 208 may be stalk size. The predictive map 264 may then be a predictive stalk size map that maps predicted stalk size values to different geographic locations in the field. In another example, the information map 258 may be a seeding genotype map, and the variable sensed by the in-situ sensors 208 may be crop state such as standing crop or down crop. The predictive map 264 may then be a predictive crop state map that maps predicted crop state values to different geographic locations in the field.

In some examples, the information map 258 is from a prior pass through the field during a prior operation and the data type is the same as the data type sensed by in-situ sensors 208, and the data type in the predictive map 264 is also the same as the data type sensed by the in-situ sensors 208. For instance, the information map 258 may be a yield map generated during a previous year, and the variable sensed by the in-situ sensors 208 may be yield. The predictive map 264 may then be a predictive yield map that maps predicted yield values to different geographic locations in the field. In such an example, the relative yield differences in the georeferenced information map 258 from the prior year can be used by predictive model generator 210 to generate a predictive model that models a relationship between the relative yield differences on the information map 258 and the yield values sensed by in-situ sensors 208 during the current harvesting operation. The predictive model is then used by predictive map generator 212 to generate a predictive yield map.

In another example, the information map 258 may be a weed intensity map generated during a prior operation, such as from a sprayer, and the variable sensed by the in-situ sensors 208 may be weed intensity. The predictive map 264 may then be a predictive weed intensity map that maps predicted weed intensity values to different geographic locations in the field. In such an example, a map of the weed intensities at time of spraying is geo-referenced recorded and provided to agricultural harvester 100 as an information map 258 of weed intensity. In-situ sensors 208 can detect weed intensity at geographic locations in the field and predictive model generator 210 may then build a predictive model that models a relationship between weed intensity at time of harvest and weed intensity at time of spraying. This is because the sprayer will have impacted the weed intensity at time of spraying, but weeds may still crop up in similar areas again by harvest. However, the weed areas at harvest are likely to have different intensity based on timing of the harvest, weather, weed type, among other things.

In some examples, predictive map 264 can be provided to the control zone generator 213. Control zone generator 213 groups adjacent portions of an area into one or more control zones based on data values of predictive map 264, that are associated with those adjacent portions. A control zone may include two or more contiguous portions of an area, such as a field, for which a control parameter corresponding to the control zone for controlling a controllable subsystem is constant. For example, a response time to alter a setting of controllable subsystems 216 may be inadequate to satisfactorily respond to changes in values contained in a map, such as predictive map 264. In that case, control zone generator 213 parses the map and identifies control zones that are of a defined size to accommodate the response time of the controllable subsystems 216. In another example, control zones may be sized to reduce wear from excessive actuator movement resulting from continuous adjustment. In some examples, there may be a different set of control zones for each controllable subsystem 216 or for groups of controllable subsystems 216. The control zones may be added to the predictive map 264 to obtain predictive control zone map 265. Predictive control zone map 265 can thus be similar to predictive map 264 except that predictive control zone map 265 includes control zone information defining the control zones. Thus, a functional predictive map 263, as described herein, may or may not include control zones. Both predictive map 264 and predictive control zone map 265 are functional predictive maps 263. In one example, a functional predictive map 263 does not include control zones, such as predictive map 264. In another example, a functional predictive map 263 does include control zones, such as predictive control zone map 265. In some examples, multiple crops may be simultaneously present in a field if an intercrop production system is implemented. In that case, predictive map generator 212 and control zone generator 213 are able to identify the location and characteristics of the two or more crops and then generate predictive map 264 and predictive control zone map 265 with control zones accordingly.

It will also be appreciated that control zone generator 213 can cluster values to generate control zones and the control zones can be added to predictive control zone map 265, or a separate map, showing only the control zones that are generated. In some examples, the control zones may be used for controlling or calibrating agricultural harvester 100 or both. In other examples, the control zones may be presented to the operator 260 and used to control or calibrate agricultural harvester 100, and, in other examples, the control zones may be presented to the operator 260 or another user or stored for later use.

Predictive map 264 or predictive control zone map 265 or both are provided to control system 214, which generates control signals based upon the predictive map 264 or predictive control zone map 265 or both. In some examples, communication system controller 229 controls communication system 206 to communicate the predictive map 264 or predictive control zone map 265 or control signals based on the predictive map 264 or predictive control zone map 265 to other agricultural harvesters that are harvesting in the same field. In some examples, communication system controller 229 controls the communication system 206 to send the predictive map 264, predictive control zone map 265, or both to other remote systems.

Operator interface controller 231 is operable to generate control signals to control operator interface mechanisms 218. The operator interface controller 231 is also operable to present the predictive map 264 or predictive control zone map 265 or other information derived from or based on the predictive map 264, predictive control zone map 265, or both to operator 260. Operator 260 may be a local operator or a remote operator. As an example, controller 231 generates control signals to control a display mechanism to display one or both of predictive map 264 and predictive control zone map 265 for the operator 260. Controller 231 may generate operator actuatable mechanisms that are displayed and can be actuated by the operator to interact with the displayed map. The operator can edit the map by, for example, correcting a crop state value displayed on the map based, for instance, on the operator's observation. Settings controller 232 can generate control signals to control various settings on the agricultural harvester 100 based upon predictive map 264, the predictive control zone map 265, or both. For instance, settings controller 232 can generate control signals to control machine and header actuators 248. In response to the generated control signals, the machine and header actuators 248 operate to control, for example, one or more of the sieve and chaffer settings, thresher clearance, rotor settings, cleaning fan speed settings, header height, header functionality, reel speed, reel position, draper functionality (where agricultural harvester 100 is coupled to a draper header), corn header functionality, internal distribution control, and other actuators 248 that affect the other functions of the agricultural harvester 100. Path planning controller 234 illustratively generates control signals to control steering subsystem 252 to steer agricultural harvester 100 according to a desired path. Path planning controller 234 can control a path planning system to generate a route for agricultural harvester 100 and can control propulsion subsystem 250 and steering subsystem 252 to steer agricultural harvester 100 along that route. Feed rate controller 236 can control various subsystems, such as propulsion subsystem 250 and machine actuators 248, to control a feed rate based upon the predictive map 264 or predictive control zone map 265 or both. For instance, as agricultural harvester 100 approaches an area containing crop having a downed crop condition that is greater than a selected threshold, feed rate controller 236 may reduce the speed of agricultural harvester 100 to ensure that crop feeding performance is acceptable and that the crop material is gathered. Header and reel controller 238 can generate control signals to control a header or a reel or other header functionality. For example, in an area of down crop, it may be beneficial to adjust header height or reel positions. Draper belt controller 240 can generate control signals to control a draper belt or other draper functionality based upon the predictive map 264, predictive control zone map 265, or both. Deck plate position controller 242 can generate control signals to control a position of a deck plate included on a header based on predictive map 264 or predictive control zone map 265 or both, and residue system controller 244 can generate signals to control a residue subsystem 138 based upon predictive map 264 or predictive control zone map 265, or both. Machine cleaning controller 245 can generate control signals to control machine cleaning subsystem 254. For instance, based upon the different types of seeds or weeds passed through agricultural harvester 100, a particular type of machine cleaning operation or a frequency with which a cleaning operation is performed may be controlled. Other controllers included on the agricultural harvester 100 can control other subsystems based on the predictive map 264 or predictive control zone map 265 or both as well.

FIGS. 3A and 3B (collectively referred to herein as FIG. 3) show a flow diagram illustrating one example of the operation of agricultural harvester 100 in generating a predictive map 264 and predictive control zone map 265 based upon information map 258.

At 280, agricultural harvester 100 receives information map 258. Examples of information map 258 or receiving information map 258 are discussed with respect to blocks 282, 284, 285 and 286. As discussed above, information map 258 maps values of a variable, corresponding to a first characteristic, to different locations in the field, as indicated at block 282. As indicated at block 281, receiving the information map 258 may involve selecting one or more of a plurality of possible information maps that are available. For instance, one information map may be a vegetative index map generated from aerial imagery. Another information map may be a map generated during a prior pass through the field which may have been performed by a different machine performing a previous operation in the field, such as a sprayer or other machine. The process by which one or more information maps are selected can be manual, semi-automated, or automated. The information map 258 is based on data collected prior to a current harvesting operation. This is indicated by block 284. For instance, the data may be collected based on aerial images or the data may be measured values taken during a previous year, earlier in the current growing season, or at other times. The information may be based on data detected in other ways (other than using aerial images) as well. For instance, information map 258 can be transmitted to agricultural harvester 100 using communication system 206 and stored in data store 202.

The information map 258 can be a predictive map as well, this is indicated by block 285. As indicated above the predictive map may include a predictive yield map or a predictive biomass map generated based, for example, in part on a prior vegetative index map or other information map and in-situ sensor values. In some examples, a predictive yield map or a predictive biomass map may be based in whole or in part on a topographic map, a soil type map, a soil constituent map, or a soil health map. The predictive yield or biomass map can be predicted and generated in other ways as well.

Information map 258 can be loaded onto agricultural harvester 100 using communication system 206 in other ways as well, and this is indicated by block 286 in the flow diagram of FIG. 3. In some examples, the information map 258 can be received by communication system 206.

Upon commencement of a harvesting operation, in-situ sensors 208 generate sensor signals indicative of one or more in-situ data values indicative of a plant characteristic, such as a crop state, as indicated by block 288. Examples of in-situ sensors 288 are discussed with respect to blocks 222, 290, and 226. As explained above, the in-situ sensors 208 include on-board sensors 222; remote in-situ sensors 224, such as UAV-based sensors flown at a time to gather in-situ data, shown in block 290; or other types of in-situ sensors, designated by in-situ sensors 226. In some examples, data from on-board sensors is georeferenced using position heading or speed data from geographic position sensor 204.

Predictive model generator 210 controls the information variable-to-in-situ variable model generator 228 to generate a model that models a relationship between the mapped values contained in the information map 258 and the in-situ values sensed by the in-situ sensors 208 as indicated by block 292. The characteristics or data types represented by the mapped values in the information map 258 and the in-situ values sensed by the in-situ sensors 208 may be the same characteristics or data type or different characteristics or data types.

The relationship or model generated by predictive model generator 210 is provided to predictive map generator 212. Predictive map generator 212 generates a predictive map 264 that predicts a value of the characteristic sensed by the in-situ sensors 208 at different geographic locations in a field being harvested, or a different characteristic that is related to the characteristic sensed by the in-situ sensors 208, using the predictive model and the information map 258, as indicated by block 294.

It should be noted that, in some examples, the information map 258 may include two or more different maps or two or more different map layers of a single map. Each map layer may represent a different data type from the data type of another map layer or the map layers may have the same data type that were obtained at different times. Each map in the two or more different maps or each layer in the two or more different map layers of a map maps a different type of variable to the geographic locations in the field. In such an example, predictive model generator 210 generates a predictive model that models the relationship between the in-situ data and each of the different variables mapped by the two or more different maps or the two or more different map layers. Similarly, the in-situ sensors 208 can include two or more sensors each sensing a different type of variable. Thus, the predictive model generator 210 generates a predictive model that models the relationships between each type of variable mapped by the information map 258 and each type of variable sensed by the in-situ sensors 208. Predictive map generator 212 can generate a functional predictive map 263 that predicts a value for each sensed characteristic sensed by the in-situ sensors 208 (or a characteristic related to the sensed characteristic) at different locations in the field being harvested using the predictive model and each of the maps or map layers in the information map 258.

Predictive map generator 212 configures the predictive map 264 so that the predictive map 264 is actionable (or consumable) by control system 214. Predictive map generator 212 can provide the predictive map 264 to the control system 214 or to control zone generator 213 or both. Some examples of different ways in which the predictive map 264 can be configured or output are described with respect to blocks 296, 295, 299 and 297. For instance, predictive map generator 212 configures predictive map 264 so that predictive map 264 includes values that can be read by control system 214 and used as the basis for generating control signals for one or more of the different controllable subsystems of the agricultural harvester 100, as indicated by block 296.

Control zone generator 213 can divide the predictive map 264 into control zones based on the values on the predictive map 264. Contiguously-geolocated values that are within a threshold value of one another can be grouped into a control zone. The threshold value can be a default threshold value, or the threshold value can be set based on an operator input, based on an input from an automated system, or based on other criteria. A size of the zones may be based on a responsiveness of the control system 214, the controllable subsystems 216, based on wear considerations, or on other criteria as indicated by block 295. Predictive map generator 212 configures predictive map 264 for presentation to an operator or other user. Control zone generator 213 can configure predictive control zone map 265 for presentation to an operator or other user. This is indicated by block 299. When presented to an operator or other user, the presentation of the predictive map 264 or predictive control zone map 265 or both may contain one or more of the predictive values on the predictive map 264 correlated to geographic location, the control zones on predictive control zone map 265 correlated to geographic location, and settings values or control parameters that are used based on the predicted values on predictive map 264 or zones on predictive control zone map 265. The presentation can, in another example, include more abstracted information or more detailed information. The presentation can also include a confidence level that indicates an accuracy with which the predictive values on predictive map 264 or the zones on predictive control zone map 265 conform to measured values that may be measured by sensors on agricultural harvester 100 as agricultural harvester 100 moves through the field. Further where information is presented to more than one location, an authentication and authorization system can be provided to implement authentication and authorization processes. For instance, there may be a hierarchy of individuals that are authorized to view and change maps and other presented information. By way of example, an on-board display device may show the maps in near real time locally on the machine, or the maps may also be generated at one or more remote locations, or both. In some examples, each physical display device at each location may be associated with a person or a user permission level. The user permission level may be used to determine which display elements are visible on the physical display device and which values the corresponding person may change. As an example, a local operator of agricultural harvester 100 may be unable to see the information corresponding to the predictive map 264 or make any changes to machine operation. A supervisor, such as a supervisor at a remote location, however, may be able to see the predictive map 264 on the display but be prevented from making any changes. A manager, who may be at a separate remote location, may be able to see all of the elements on predictive map 264 and also be able to change the predictive map 264. In some instances, the predictive map 264 accessible and changeable by a manager located remotely may be used in machine control. This is one example of an authorization hierarchy that may be implemented. The predictive map 264 or predictive control zone map 265 or both can be configured in other ways as well, as indicated by block 297.

At block 298, input from geographic position sensor 204 and other in-situ sensors 208 are received by the control system. Particularly, at block 300, control system 214 detects an input from the geographic position sensor 204 identifying a geographic location of agricultural harvester 100. Block 302 represents receipt by the control system 214 of sensor inputs indicative of trajectory or heading of agricultural harvester 100, and block 304 represents receipt by the control system 214 of a speed of agricultural harvester 100. Block 306 represents receipt by the control system 214 of other information from various in-situ sensors 208.

At block 308, control system 214 generates control signals to control the controllable subsystems 216 based on the predictive map 264 or predictive control zone map 265 or both and the input from the geographic position sensor 204 and any other in-situ sensors 208. At block 310, control system 214 applies the control signals to the controllable subsystems. It will be appreciated that the particular control signals that are generated, and the particular controllable subsystems 216 that are controlled, may vary based upon one or more different things. For example, the control signals that are generated and the controllable subsystems 216 that are controlled may be based on the type of predictive map 264 or predictive control zone map 265 or both that is being used. Similarly, the control signals that are generated and the controllable subsystems 216 that are controlled and the timing of the control signals can be based on various latencies of crop flow through the agricultural harvester 100 and the responsiveness of the controllable subsystems 216.

By way of example, a generated predictive map 264 in the form of a predictive crop state map can be used to control one or more controllable subsystems 216. For example, the functional predictive crop state map can include crop state values georeferenced to locations within the field being harvested. The functional predictive crop state map can be extracted and used to control, for example, the steering and propulsion subsystems 252 and 250. By controlling the steering and propulsion subsystems 252 and 250, a feed rate of material or grain moving through the agricultural harvester 100 can be controlled. Or for example, by controlling the steering and propulsion subsystems 252 and 250, a direction opposite the direction the crop is leaning of the downed crop can be maintained. Similarly, the header height can be controlled to take in more or less material (in some cases the header has to be lowered to ensure crop is contacted) and thus the header height can also be controlled to control feed rate of material through the agricultural harvester 100. In other examples, if the predictive map 264 maps a crop state forward of the machine in which crop is in a downed condition along one portion of the header and not on another portion of the header or if crop is in a downed condition to a greater extent along one portion of the header compared to another portion of the header, the header can be controlled to tilt, roll, or both to gather the downed crop in a more effective manner. The preceding examples involving feed rate and header control using a functional predictive crop state map is provided merely as an example. Consequently, a wide variety of other control signals can be generated using values obtained from a predictive crop state map or other type of functional predictive map to control one or more of the controllable subsystems 216.

At block 312, a determination is made as to whether the harvesting operation has been completed. If harvesting is not completed the processing advances to block 314 where in-situ sensor data from geographic position sensor 204 and in-situ sensors 208 (and perhaps other sensors) continue to be read.

In some examples, at block 316, agricultural harvester 100 can also detect learning trigger criteria to perform machine learning on one or more of the predictive map 264, predictive control zone map 265, the model generated by predictive model generator 210, the zones generated by control zone generator 213, one or more control algorithms implemented by the controllers in the control system 214, and other triggered learning.

The learning trigger criteria can include any of a wide variety of different criteria. Some examples of detecting trigger criteria are discussed with respect to blocks 318, 320, 321, 322 and 324. For instance, in some examples, triggered learning can involve recreation of a relationship used to generate a predictive model when a threshold amount of in-situ sensor data are obtained from in-situ sensors 208. In such examples, receipt of an amount of in-situ sensor data from the in-situ sensors 208 that exceeds a threshold triggers or causes the predictive model generator 210 to generate a new predictive model that is used by predictive map generator 212. Thus, as agricultural harvester 100 continues a harvesting operation, receipt of the threshold amount of in-situ sensor data from the in-situ sensors 208 triggers the creation of a new relationship represented by a predictive model generated by predictive model generator 210. Further, new predictive map 264, predictive control zone map 265, or both can be regenerated using the new predictive model. Block 318 represents detecting a threshold amount of in-situ sensor data used to trigger creation of a new predictive model.

In other examples, the learning trigger criteria may be based on how much the in-situ sensor data from the in-situ sensors 208 are changing, such as over time or compared to previous values. For example, if variations within the in-situ sensor data (or the relationship between the in-situ sensor data and the information in information map 258) are within a selected range or is less than a defined amount, or below a threshold value, then a new predictive model is not generated by the predictive model generator 210. As a result, the predictive map generator 212 does not generate a new predictive map 264, predictive control zone map 265, or both. However, if variations within the in-situ sensor data are outside of the selected range, are greater than the defined amount, or are above the threshold value, for example, then the predictive model generator 210 generates a new predictive model using all or a portion of the newly received in-situ sensor data that the predictive map generator 212 uses to generate a new predictive map 264. At block 320, variations in the in-situ sensor data, such as a magnitude of an amount by which the data exceeds the selected range or a magnitude of the variation of the relationship between the in-situ sensor data and the information in the information map 258, can be used as a trigger to cause generation of a new predictive model and predictive map. Keeping with the examples described above, the threshold, the range, and the defined amount can be set to default values; set by an operator or user interaction through a user interface; set by an automated system; or set in other ways.

Other learning trigger criteria can also be used. For instance, if predictive model generator 210 switches to a different information map (different from the originally selected information map 258), then switching to the different information map may trigger re-learning by predictive model generator 210, predictive map generator 212, control zone generator 213, control system 214, or other items. In another example, transitioning of agricultural harvester 100 to a different topography or to a different control zone may be used as learning trigger criteria as well.

In some instances, operator 260 can also edit the predictive map 264 or predictive control zone map 265 or both. The edits can change a value on the predictive map 264 or, change a size, shape, position or existence of a control zone on predictive control zone map 265, or both. Block 321 shows that edited information can be used as learning trigger criteria.

In some instances, it may also be that operator 260 observes that automated control of a controllable subsystem, is not what the operator desires. In such instances, the operator 260 may provide a manual adjustment to the controllable subsystem reflecting that the operator 260 desires the controllable subsystem to operate in a different way than is being commanded by control system 214. Thus, manual alteration of a setting by the operator 260 can cause one or more of predictive model generator 210 to relearn a model, predictive map generator 212 to regenerate map 264, control zone generator 213 to regenerate one or more control zones on predictive control zone map 265, and control system 214 to relearn a control algorithm or to perform machine learning on one or more of the controller components 232 through 246 in control system 214 based upon the adjustment by the operator 260, as shown in block 322. Block 324 represents the use of other triggered learning criteria.

In other examples, relearning may be performed periodically or intermittently based, for example, upon a selected time interval such as a discrete time interval or a variable time interval, as indicated by block 326.

If relearning is triggered, whether based upon learning trigger criteria or based upon passage of a time interval, as indicated by block 326, then one or more of the predictive model generator 210, predictive map generator 212, control zone generator 213, and control system 214 performs machine learning to generate a new predictive model, a new predictive map, a new control zone, and a new control algorithm, respectively, based upon the learning trigger criteria. The new predictive model, the new predictive map, and the new control algorithm are generated using any additional data that has been collected since the last learning operation was performed. Performing relearning is indicated by block 328.

If the harvesting operation has been completed, operation moves from block 312 to block 330 where one or more of the predictive map 264, predictive control zone map 265, and predictive model generated by predictive model generator 210 are stored. The predictive map 264, predictive control zone map 265, and predictive model may be stored locally on data store 202 or sent to a remote system using communication system 206 for later use.

It will be noted that while some examples herein describe predictive model generator 210 and predictive map generator 212 receiving an information map in generating a predictive model and a functional predictive map, respectively, in other examples, the predictive model generator 210 and predictive map generator 212 can receive, in generating a predictive model and a functional predictive map, respectively other types of maps, including predictive maps, such as a functional predictive map generated during the harvesting operation.

FIG. 4 is a block diagram of a portion of the agricultural harvester 100 shown in FIG. 1. Particularly, FIG. 4 shows, among other things, examples of the predictive model generator 210 and the predictive map generator 212 in more detail. FIG. 4 also illustrates information flow among the various components shown therein. As shown, the predictive model generator 210 receives one or more of a vegetative index map 332, a seeding characteristic map 333, a predictive yield map 335, or a predictive biomass map 337 as an information map. Vegetative index map 332 includes georeferenced vegetative index values. Seeding characteristic map 333 includes georeferenced seed characteristic values. For example, seed characteristics can include the location and quantity of seeds planted. Additionally, seed characteristics can include the type of seed, genetic stalk or stem strength, genetic susceptibility to lodging, coating on the seed, genotype of the seed, etc.

Predictive yield map 335 includes georeferenced predictive yield values. Predictive yield map 335 can be generated using a process described in FIGS. 2 and 3, where the information map includes a vegetative index map or a historical yield map and the in-situ sensor includes a yield sensor. Predictive yield map 335 can be generated in other ways as well.

Predictive biomass map 337 includes georeferenced predictive biomass values. Predictive biomass map 337 can be generated using a process described in FIGS. 2 and 3, where the information map includes a vegetative index map and the in-situ sensor includes a rotor drive pressure or optical sensor, that generate sensor signals indicative of biomass. Predictive biomass map 337 can be generated in other ways as well.

Besides receiving one or more of a vegetative index map 332, seeding characteristic map 333, predictive yield map 335, or predictive biomass map 337 as an information map, predictive model generator 210 also receives a geographic location 334, or an indication of geographic location, from geographic position sensor 204. In-situ sensors 208 illustratively include an on-board crop state sensor 336 as well as a processing system 338. The processing system 338 processes sensor data generated from the on-board crop state sensors 336.

In some examples, on-board crop state sensor 336 may be an optical sensor on agricultural harvester 100. The optical sensor may be arranged at the front of agricultural harvester 100 to collect images of the field in front of agricultural harvester 100 as agricultural harvester 100 moves through the field during a harvesting operation. Processing system 338 processes one or more images obtained via the on-board crop state sensor 336 to generate processed image data identifying one or more characteristics of the crop plants in the image. For example, the magnitude and orientation of crop plant in a downed condition. Processing system 338 can also geolocate the values received from the in-situ sensor 208. For example, the location of agricultural harvester 100 at the time a signal from in-situ sensor 208 is received is typically not the accurate location of the sensed crop state. This is because it takes time from forward sensing to the time agricultural harvester 100 (equipped with the geographic position sensor) contacts the crop plants that were sensed for crop state. In some examples, to account for the forward sensing, a camera field of view can be calibrated such that areas of downed crop in an image captured by the camera can be geolocated based on their location in the image.

Other crop state sensors may also be used. In some examples, raw or processed data from on-board crop state sensor 336 may be presented to operator 260 via operator interface mechanism 218. Operator 260 may be onboard of the work agricultural harvester 100 or at a remote location.

The present discussion proceeds with respect to an example in which on-board crop state sensor 336 includes an optical sensor, such as a camera. It will be appreciated that this is just one example, and the sensors mentioned above, as other examples of on-board crop state sensor 336, are contemplated herein as well. As shown in FIG. 4, the predictive model generator 210 includes a vegetative index-to-crop state model generator 342, a yield-to-crop state model generator 344, and a biomass-to-crop state model generator 346. In other examples, the predictive model generator 210 may include additional, fewer, or different components than those shown in the example of FIG. 4. Consequently, in some examples, the predictive model generator 210 may include other items 348 as well, which may include other types of predictive model generators to generate other types of crop state models.

Model generator 342 identifies a relationship between in-situ crop state data 340 at a geographic location corresponding to where in-situ crop state data 340 were geolocated and vegetative index values from the vegetative index map 332 corresponding to the same location in the field where crop state data 340 were geolocated. Based on this relationship established by model generator 342, model generator 342 generates a predictive crop state model. The crop state model is used to predict a crop state at different locations in the field based upon the georeferenced vegetative index values contained in the vegetative index map 332 at the same locations in the field. In some examples, model generator 342 may use a time series of vegetative index maps to identify rate of crop senescence following green snap, increased crop stress from stalk damage, and other.

Model generator 344 identifies a relationship between the crop state represented in the in-situ crop state data 340, at a geographic location corresponding to where the in-situ crop state data 340 were geolocated, and the seeding characteristic value at the same location. The seeding characteristic value is the georeferenced value contained in the seeding characteristic map 333. Model generator 344 generates a predictive crop state model that predicts the crop state at a location in the field based upon the seeding characteristic value. The crop state model is used to predict a crop state at different locations in the field based upon the georeferenced seeding characteristic values contained in the seeding characteristic map 333 at the same locations in the field. The seeding characteristic, for instance, could be the seed planting density.

Model generator 345 identifies a relationship between the crop state represented in the in-situ crop state data 340, at a geographic location corresponding to where the in-situ crop state data 340 were geolocated, and the predicted yield at the same location. The predicted yield value is the georeferenced value contained in the predictive yield map 335. Model generator 345 generates a predictive crop state model that predicts the crop state at a location in the field based upon the predicted yield value. The crop state model is used to predict a crop state at different locations in the field based upon the georeferenced predictive yield values contained in the predictive yield map 335 at the same locations in the field.

Model generator 346 identifies a relationship between the crop state represented in the in-situ crop state data 340, at a geographic location corresponding to where the in-situ crop state data 340 were geolocated, and the predicted biomass at the same location. The predicted biomass value is the georeferenced value contained in the predictive biomass map 337. Model generator 346 generates a predictive crop state model that predicts the crop state at a location in the field based upon the predicted biomass value. The crop state model is used to predict a crop state at different locations in the field based upon the georeferenced predictive biomass values contained in the predictive biomass map 337 at the same locations in the field.

In light of the above, the predictive model generator 210 is operable to produce a plurality of predictive crop state models, such as one or more of the predictive crop state models generated by model generators 342, 344, 345, 346, and 348. In another example, two or more of the predictive crop state models described above may be combined into a single predictive crop state model that predicts a crop state based upon the vegetative index value, seeding characteristic value, predictive yield value, or predictive biomass values at different locations in the field. Any of these crop state models, or combinations thereof, are represented collectively by crop state model 350 in FIG. 4.

The predictive crop state model 350 is provided to predictive map generator 212. In the example of FIG. 4, predictive map generator 212 includes a crop state map generator 352. In other examples, the predictive map generator 212 may include additional, fewer, or different map generators. Crop state map generator 352 receives the predictive crop state model 350 that predicts crop state based upon a relationship between a sensed crop state value and a value from one or more of the vegetative index map 332, seeding characteristic map 333, predictive yield map 335, and predictive biomass map 337 at a corresponding location where the crop state was sensed.

Crop state map generator 354 can also generate a functional predictive crop state map 360 that predicts crop state at different locations in the field based upon the vegetative index value, seeding characteristic value, predictive yield value, or predictive biomass value at those locations in the field and the predictive crop state model 350. The generated functional predictive crop state map 360 may be provided to control zone generator 213, control system 214, or both. Control zone generator 213 generates control zones and incorporates those control zones into the functional predictive map, i.e., predictive map 360, to produce predictive control zone map 265. One or both of functional predictive maps 264 or predictive control zone map 265 may be presented to the operator 260 or anther user or be provided to control system 214, which generates control signals to control one or more of the controllable subsystems 216 based upon the predictive map 264, predictive control zone map 265, or both.

FIG. 5 is a flow diagram of an example of operation of predictive model generator 210 and predictive map generator 212 in generating the predictive crop state model 350 and the functional predictive crop state map 360. At block 362, predictive model generator 210 and predictive map generator 212 receive one or more of prior vegetative index map 332, seeding characteristic map 333, predictive yield map 335, and predictive biomass map 337.

At block 363, information map selector 209 selects one or more specific information maps 250 for use by predictive model generator 210. In some examples, information map selector 209 can change which information map is being used upon detection that one of the other candidate information maps is more closely correlating to the in-situ sensed crop state. For example, a change from vegetative index map 332 to seeding characteristic map 333 may occur where the seeding characteristic map 333 is correlating better to the crop state sensed by in-situ sensor.

At block 364, a crop state sensor signal is received from an on-board crop state sensor 336. As discussed above, the on-board crop state sensor 336 may be an optical sensor 365 or some other crop state sensor 370.

At block 372, processing system 338 processes the one or more received in-situ sensor signals received from the on-board crop state sensors 336 to generate a crop state value indicative of a crop state characteristic of the crop plants in the field proximate agricultural harvester 100.

At block 382, predictive model generator 210 also obtains the geographic location corresponding to the sensor signal. For instance, the predictive model generator 210 can obtain the geographic position from geographic position sensor 204 and determine, based upon machine delays (e.g., machine processing speed), machine speed and sensor considerations (e.g., a camera field of view, sensor calibration, etc.), a precise geographic location where the in-situ sensed crop state is to be attributed. For example, the exact time a crop state sensor signal is captured typically does not correspond to the crop state of the crop at a current geographic position of agricultural harvester 100. Instead, the current in-situ crop state sensor signal corresponds to a location on the field forward of agricultural harvester 100 since the current in-situ crop state sensor signal was sensed in an image take in front of agricultural harvester 100. This is indicated by block 378.

At block 384, predictive model generator 210 generates one or more predictive crop state models, such as crop state model 350, that model a relationship between at least one of a vegetative index value, a seeding characteristic, a predictive yield value, or a predictive biomass value obtained from an information map, such as information map 258, and a crop state being sensed by the in-situ sensor 208. For instance, predictive model generator 210 may generate a predictive crop state model based on seeding density values, which can also indicate a high crop plant population, and a sensed crop state indicated by the sensor signal obtained from in-situ sensor 208.

At block 386, the predictive crop state model, such as predictive crop state model 350, is provided to predictive map generator 212, which generates a functional predictive crop state map that maps a predicted crop state to different geographic locations in the field based on the prior vegetative index map 332, seeding characteristic map 333, predictive yield map 335, or predictive biomass map 337 and the predictive crop state model 350. For instance, in some examples, the functional predictive crop state map 360 predicts crop state. In other examples, the functional predictive crop state map 360 map predicts other items. Further, the functional predictive crop state map 360 can be generated during the course of an agricultural harvesting operation. Thus, as an agricultural harvester is moving through a field performing an agricultural harvesting operation, the functional predictive crop state map 360 is generated.

At block 394, predictive map generator 212 outputs the functional predictive crop state map 360. At block 393, predictive map generator 212 configures the functional predictive crop state map 360 for consumption by control system 214. At block 395, predictive map generator 212 can also provide the map 360 to control zone generator 213 for generation of control zones. At block 397, predictive map generator 212 configures the map 360 in other ways as well. The functional predictive crop state map 360 (with or without the control zones) is provided to control system 214. At block 396, control system 214 generates control signals to control the controllable subsystems 216 based upon the functional predictive crop state map 360.

It can thus be seen that the present system takes an information map that maps a characteristic such as vegetative index, a seeding characteristic, a predictive yield, or a predictive biomass values to different locations in a field. The present system also uses one or more in-situ sensors that sense in-situ sensor data that is indicative of a characteristic, such as crop state, and generates a model that models a relationship between the crop state sensed in-situ using the in-situ sensor and the characteristic mapped in the information map. Thus, the present system generates a functional predictive map using a model and an information map and may configure the generated functional predictive map for consumption by a control system or for presentation to a local or remote operator or other user. For example, the control system may use the map to control one or more systems of a combine harvester.

The present discussion has mentioned processors and servers. In some examples, the processors and servers include computer processors with associated memory and timing circuitry, not separately shown. The processors and servers are functional parts of the systems or devices to which the processors and servers belong and are activated by and facilitate the functionality of the other components or items in those systems.

Also, a number of user interface displays have been discussed. The displays can take a wide variety of different forms and can have a wide variety of different user actuatable operator interface mechanisms disposed thereon. For instance, user actuatable operator interface mechanisms may include text boxes, check boxes, icons, links, drop-down menus, search boxes, etc. The user actuatable operator interface mechanisms can also be actuated in a wide variety of different ways. For instance, the user actuatable operator interface mechanisms can be actuated using operator interface mechanisms such as a point and click device, such as a track ball or mouse, hardware buttons, switches, a joystick or keyboard, thumb switches or thumb pads, etc., a virtual keyboard or other virtual actuators. In addition, where the screen on which the user actuatable operator interface mechanisms are displayed is a touch sensitive screen, the user actuatable operator interface mechanisms can be actuated using touch gestures. Also, user actuatable operator interface mechanisms can be actuated using speech commands using speech recognition functionality. Speech recognition may be implemented using a speech detection device, such as a microphone, and software that functions to recognize detected speech and execute commands based on the received speech.

A number of data stores have also been discussed. It will be noted the data stores can each be broken into multiple data stores. In some examples, one or more of the data stores may be local to the systems accessing the data stores, one or more of the data stores may all be located remote form a system utilizing the data store, or one or more data stores may be local while others are remote. All of these configurations are contemplated by the present disclosure.

Also, the figures show a number of blocks with functionality ascribed to each block. It will be noted that fewer blocks can be used to illustrate that the functionality ascribed to multiple different blocks is performed by fewer components. Also, more blocks can be used illustrating that the functionality may be distributed among more components. In different examples, some functionality may be added, and some may be removed.

It will be noted that the above discussion has described a variety of different systems, components, logic and interactions. It will be appreciated that any or all of such systems, components, logic and interactions may be implemented by hardware items, such as processors, memory, or other processing components, some of which are described below, that perform the functions associated with those systems, components, logic, or interactions. In addition, any or all of the systems, components, logic and interactions may be implemented by software that is loaded into a memory and is subsequently executed by a processor or server or other computing component, as described below. Any or all of the systems, components, logic and interactions may also be implemented by different combinations of hardware, software, firmware, etc., some examples of which are described below. These are some examples of different structures that may be used to implement any or all of the systems, components, logic and interactions described above. Other structures may be used as well.

Figure 6:
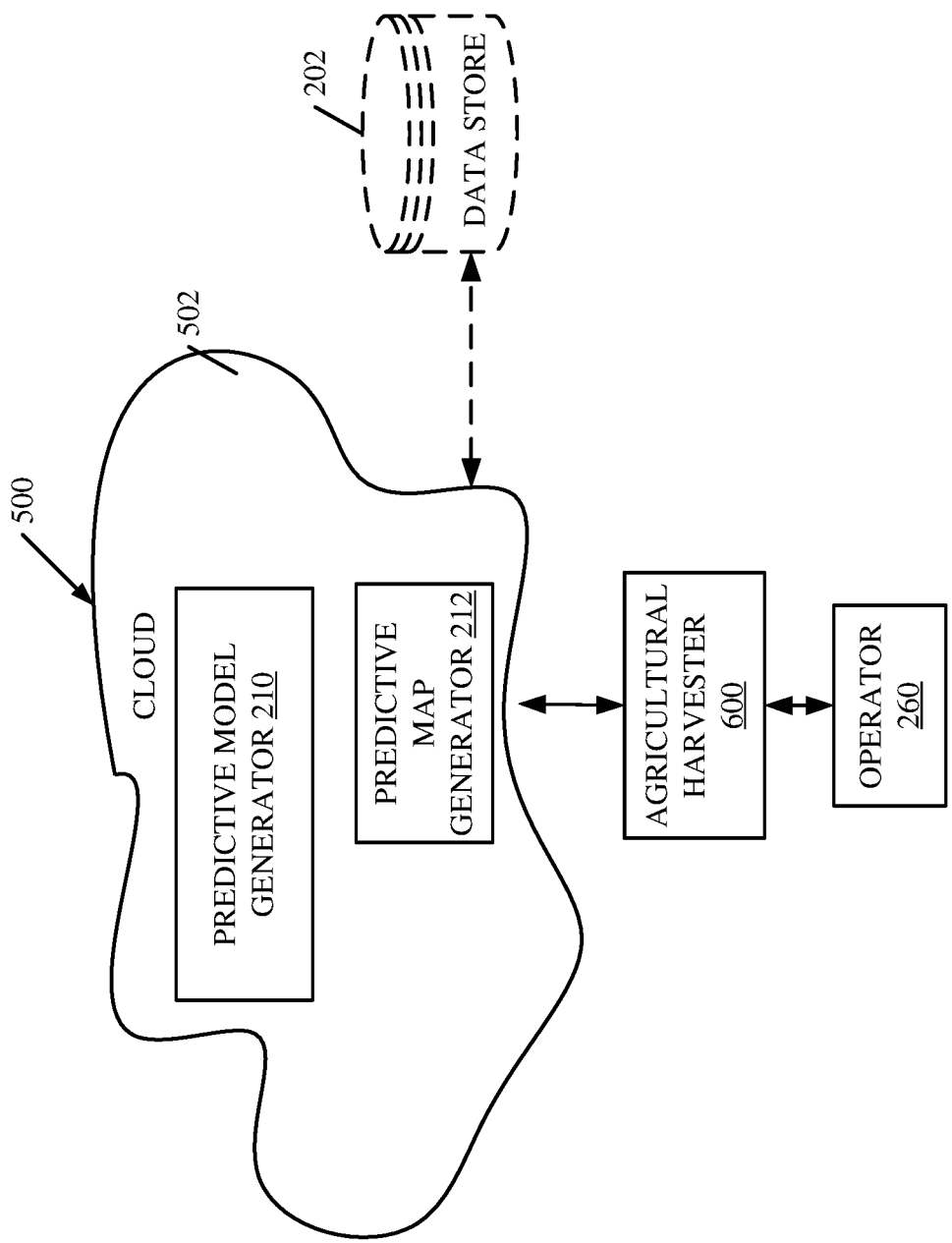
FIG. 6 is a block diagram showing one example of an agricultural harvester in communication with a remote server environment.

FIG. 6 is a block diagram of agricultural harvester 600, which may be similar to agricultural harvester 100 shown in FIG. 2. The agricultural harvester 600 communicates with elements in a remote server architecture 500. In some examples, remote server architecture 500 provides computation, software, data access, and storage services that do not require end-user knowledge of the physical location or configuration of the system that delivers the services. In various examples, remote servers may deliver the services over a wide area network, such as the internet, using appropriate protocols. For instance, remote servers may deliver applications over a wide area network and may be accessible through a web browser or any other computing component. Software or components shown in FIG. 2 as well as data associated therewith, may be stored on servers at a remote location. The computing resources in a remote server environment may be consolidated at a remote data center location, or the computing resources may be dispersed to a plurality of remote data centers. Remote server infrastructures may deliver services through shared data centers, even though the services appear as a single point of access for the user. Thus, the components and functions described herein may be provided from a remote server at a remote location using a remote server architecture. Alternatively, the components and functions may be provided from a server, or the components and functions can be installed on client devices directly, or in other ways.

In the example shown in FIG. 6, some items are similar to those shown in FIG. 2 and those items are similarly numbered. FIG. 6 specifically shows that predictive model generator 210 or predictive map generator 212, or both, may be located at a server location 502 that is remote from the agricultural harvester 600. Therefore, in the example shown in FIG. 6, agricultural harvester 600 accesses systems through remote server location 502.

FIG. 6 also depicts another example of a remote server architecture. FIG. 6 shows that some elements of FIG. 2 may be disposed at a remote server location 502 while others may be located elsewhere. By way of example, data store 202 may be disposed at a location separate from location 502 and accessed via the remote server at location 502. Regardless of where the elements are located, the elements can be accessed directly by agricultural harvester 600 through a network such as a wide area network or a local area network; the elements can be hosted at a remote site by a service; or the elements can be provided as a service or accessed by a connection service that resides in a remote location. Also, data may be stored in any location, and the stored data may be accessed by, or forwarded to, operators, users or systems. For instance, physical carriers may be used instead of, or in addition to, electromagnetic wave carriers. In some examples, where wireless telecommunication service coverage is poor or nonexistent, another machine, such as a fuel truck or other mobile machine or vehicle, may have an automated, semi-automated or manual information collection system. As the combine harvester 600 comes close to the machine containing the information collection system, such as a fuel truck prior to fueling, the information collection system collects the information from the combine harvester 600 using any type of ad-hoc wireless connection. The collected information may then be forwarded to another network when the machine containing the received information reaches a location where wireless telecommunication service coverage or other wireless coverage—is available. For instance, a fuel truck may enter an area having wireless communication coverage when traveling to a location to fuel other machines or when at a main fuel storage location. All of these architectures are contemplated herein. Further, the information may be stored on the agricultural harvester 600 until the agricultural harvester 600 enters an area having wireless communication coverage. The agricultural harvester 600, itself, may send the information to another network.

It will also be noted that the elements of FIG. 2, or portions thereof, may be disposed on a wide variety of different devices. One or more of those devices may include an on-board computer, an electronic control unit, a display unit, a server, a desktop computer, a laptop computer, a tablet computer, or other mobile device, such as a palm top computer, a cell phone, a smart phone, a multimedia player, a personal digital assistant, etc.

In some examples, remote server architecture 500 may include cybersecurity measures. Without limitation, these measures may include encryption of data on storage devices, encryption of data sent between network nodes, authentication of people or processes accessing data, as well as the use of ledgers for recording metadata, data, data transfers, data accesses, and data transformations. In some examples, the ledgers may be distributed and immutable (e.g., implemented as blockchain).

Figure 7:
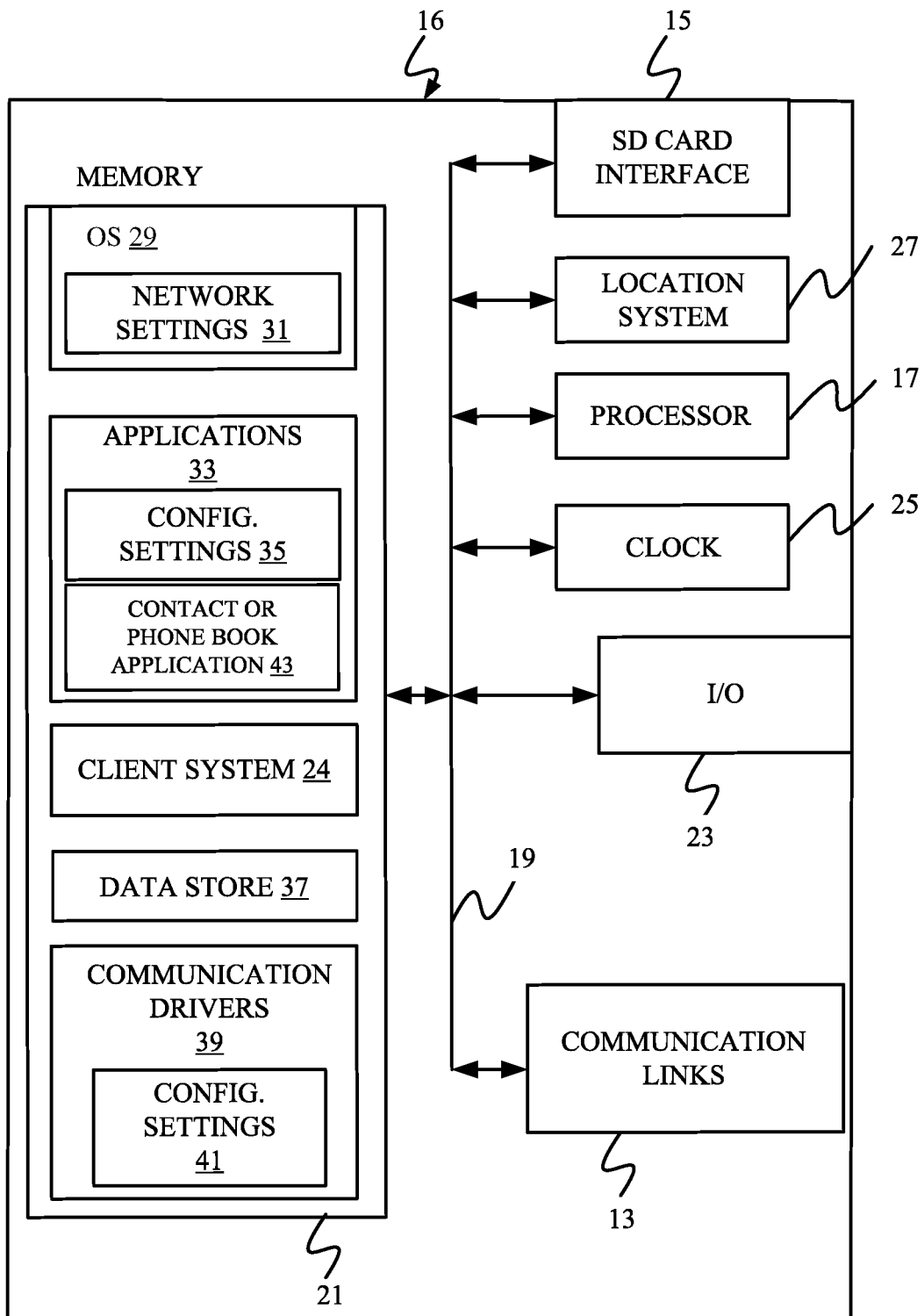
FIGS. 7-9 show examples of mobile devices that can be used in an agricultural harvester.
Figure 8:
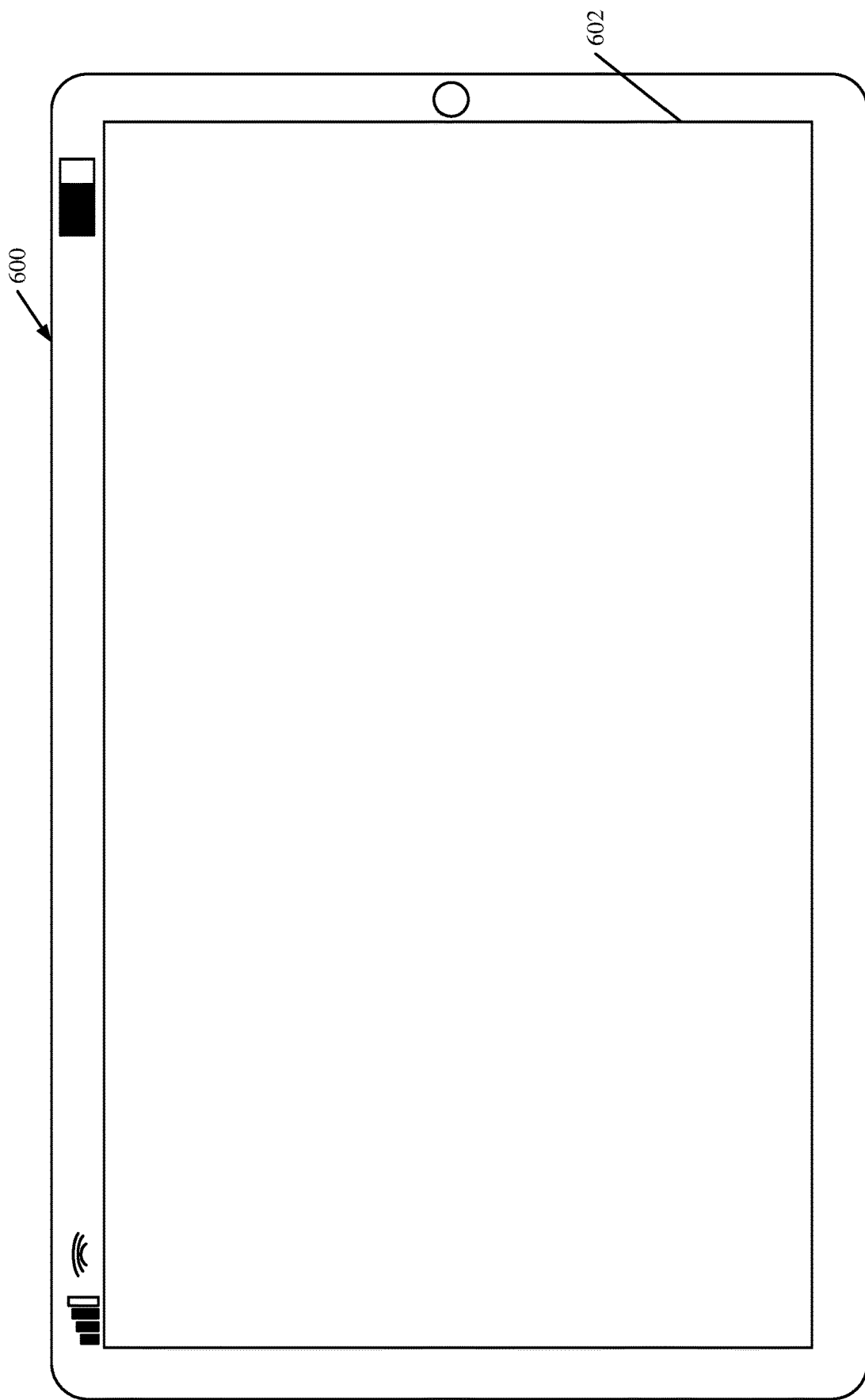
Figure 9:
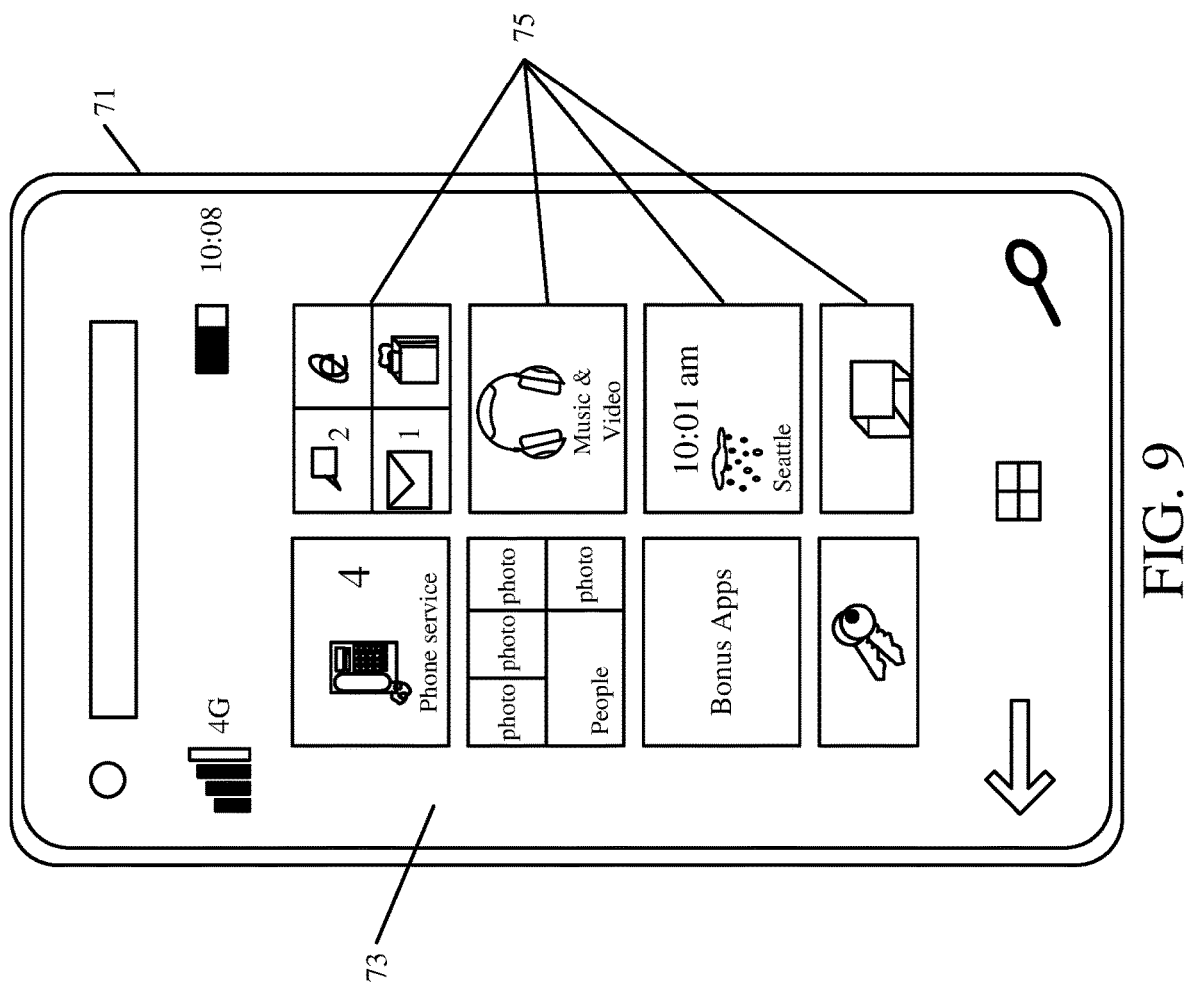

FIG. 7 is a simplified block diagram of one illustrative example of a handheld or mobile computing device that can be used as a user's or client's hand held device 16, in which the present system (or parts of it) can be deployed. For instance, a mobile device can be deployed in the operator compartment of agricultural harvester 100 for use in generating, processing, or displaying the maps discussed above. FIGS. 8-9 are examples of handheld or mobile devices.

FIG. 7 provides a general block diagram of the components of a client device 16 that can run some components shown in FIG. 2, that interacts with them, or both. In the device 16, a communications link 13 is provided that allows the handheld device to communicate with other computing devices and under some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from other FIGS.) along a bus 19 that is also connected to memory 21 and input/output (I/O) components 23, as well as clock 25 and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. Location system 27 can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. Memory 21 may also include computer storage media (described below). Memory 21 stores computer readable instructions that, when executed by processor 17, cause the processor to perform computer-implemented steps or functions according to the instructions. Processor 17 may be activated by other components to facilitate their functionality as well.

FIG. 8 shows one example in which device 16 is a tablet computer 600. In FIG. 8, computer 600 is shown with user interface display screen 602. Screen 602 can be a touch screen or a pen-enabled interface that receives inputs from a pen or stylus. Tablet computer 600 may also use an on-screen virtual keyboard. Of course, computer 600 might also be attached to a keyboard or other user input device through a suitable attachment mechanism, such as a wireless link or USB port, for instance. Computer 600 may also illustratively receive voice inputs as well.

FIG. 9 is similar to FIG. 8 except that the device is a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 10:
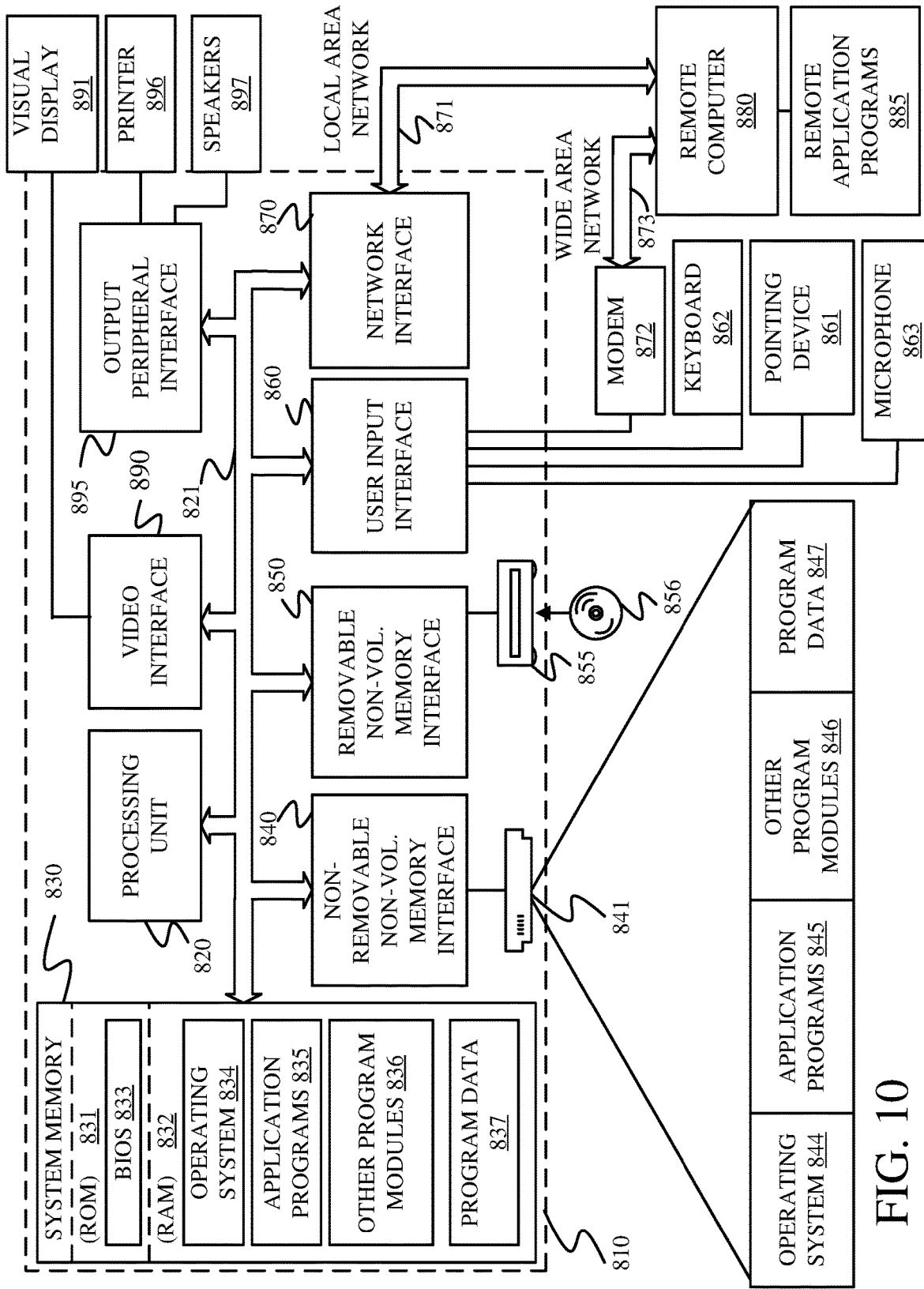
FIG. 10 is a block diagram showing one example of a computing environment that can be used in an agricultural harvester and the architectures illustrated in previous figures.

FIG. 10 is one example of a computing environment in which elements of FIG. 2 can be deployed. With reference to FIG. 10, an example system for implementing some embodiments includes a computing device in the form of a computer 810 programmed to operate as discussed above. Components of computer 810 may include, but are not limited to, a processing unit 820 (which can comprise processors or servers from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 2 can be deployed in corresponding portions of FIG. 10.

Computer 810 typically includes a variety of computer readable media. Computer readable media may be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. Computer readable media includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory or both such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data or program modules or both that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable volatile/nonvolatile computer storage media. By way of example only, FIG. 10 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a controller area network—CAN, local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 10 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is an agricultural work machine comprising:

a communication system that receives an information map that includes values of a first agricultural characteristic corresponding to different geographic locations in a field;

a geographic position sensor that detects a geographic location of the agricultural work machine;

an in-situ sensor that detects a crop state as a second agricultural characteristic corresponding to the geographic location;

a predictive model generator that generates a predictive agricultural model that models a relationship between the first agricultural characteristic and the second agricultural characteristic based on a value of the first agricultural characteristic in the information map at the geographic location and a value of the second agricultural characteristic sensed by the in-situ sensor at the geographic location; and a predictive map generator that generates a functional predictive agricultural map of the field that maps predictive values of the second agricultural characteristic to the different geographic locations in the field based on the values of the first agricultural characteristic in the information map and based on the predictive agricultural model.

Example 2 is the agricultural work machine of any or all previous examples, wherein the predictive map generator configures the functional predictive agricultural map for consumption by a control system that generates control signals to control a controllable subsystem on the agricultural work machine based on the functional predictive agricultural map.

Example 3 is the agricultural work machine of any or all previous examples, wherein the in-situ sensor generates sensor data indicative of the crop state and wherein the in-situ sensor comprises:

a processing system configured to analyze the sensor data and determine at least one of an orientation or a magnitude of the crop state.

Example 4 is the agricultural work machine of any or all previous examples, wherein the information map comprises a prior vegetative index map that maps, as the first agricultural characteristic, vegetative index values to the different geographic locations in the field.

Example 5 is the agricultural work machine of any or all previous examples, wherein the predictive model generator is configured to identify the relationship between the crop state detected at the geographic location and a vegetative index value of the vegetative index values in the prior vegetative index map at the geographic location, the predictive agricultural model being configured to receive an input vegetative index value as a model input and generate a predicted crop state value as a model output based on the identified relationship.

Example 6 is the agricultural work machine of any or all previous examples, wherein the information map comprises a seeding characteristic map that maps, as the first agricultural characteristic, seeding characteristic values to the different geographic locations in the field.

Example 7 is the agricultural work machine of any or all previous examples, wherein the predictive model generator is configured to identify the relationship between the crop state detected at the geographic location and a seeding characteristic in the seeding characteristic map at the geographic location, the predictive agricultural model being configured to receive an input seeding characteristic value as a model input and generate a predicted crop state value as a model output based on the identified relationship.

Example 8 is the agricultural work machine of any or all previous examples, wherein the seeding characteristic comprises genetic stalk or stem strength.

Example 9 is the agricultural work machine of any or all previous examples, wherein the seeding characteristic comprises genetic susceptibility to lodging.

Example 10 is the agricultural work machine of any or all previous examples, wherein the information map comprises a predictive map that maps, as the first agricultural characteristic, predictive yield or predictive biomass values to the different geographic locations in the field.

Example 11 is the agricultural work machine of any or all previous examples, wherein the predictive model generator is configured to identify the relationship between the crop state detected at the geographic location and the predictive yield or the predictive biomass in the predictive map at the geographic location, the predictive agricultural model being configured to receive an input yield or biomass value as a model input and generate a predicted crop state value as a model output based on the identified relationship.

Example 12 is a computer implemented method of generating a functional predictive agricultural map, the computer implemented method comprising:

receiving an information map at an agricultural work machine that indicates values of a first agricultural characteristic corresponding to different geographic locations in a field;

detecting a geographic location of the agricultural work machine;

detecting, with an in-situ sensor, a crop state as a second agricultural characteristic corresponding to the geographic location;

generating a predictive agricultural model that models a relationship between the first agricultural characteristic and the second agricultural characteristic; and controlling a predictive map generator to generate the functional predictive agricultural map of the field that maps predictive values of the second agricultural characteristic to the different locations in the field based on the values of the first agricultural characteristic in the information map and the predictive agricultural model.

Example 13 is the computer implemented method of any or all previous examples, and further comprising:

configuring the functional predictive agricultural map for a control system that generates control signals to control a controllable subsystem on the agricultural work machine based on the functional predictive agricultural map.

Example 14 is the computer implemented method of any or all previous examples, wherein receiving the information map comprises receiving a prior vegetative index map that maps, as the first agricultural characteristic, vegetative index values to the different geographic locations in the field.

Example 15 is the computer implemented method of any or all previous examples, wherein generating the predictive agricultural model comprises:

identifying the relationship between the vegetative index values and the crop state based on the crop state detected at the geographic location and a vegetative index value of the vegetative index values in the prior vegetative index map at the geographic location; and controlling a predictive model generator to generate the predictive agricultural model that receives an input vegetative index value as a model input and generates a predicted crop state value as a model output based on the identified relationship.

Example 16 is the computer implemented method of any or all previous examples, wherein receiving the information map comprises receiving a seeding characteristic map that maps, as the first agricultural characteristic, seeding characteristic values to the different geographic locations in the field.

Example 17 is the computer implemented method of any or all previous examples, wherein generating the predictive agricultural model comprises:

identifying the relationship between the seeding characteristic values and the crop state based on the crop state detected at the geographic location and the seeding characteristic values in the seeding characteristic map at the geographic location; and controlling a predictive model generator to generate the predictive agricultural model that receives an input seeding characteristic value as a model input and generates a predicted crop state value as a model output based on the identified relationship.

Example 18 is the computer implemented method of any or all previous examples, wherein the seeding characteristic values comprise seed planting density values.

Example 19 is an agricultural work machine comprising:

a communication system that receives a prior vegetative index map that indicates vegetative index values corresponding to different geographic locations in a field;

a geographic position sensor that detects a geographic location of the agricultural work machine;

an in-situ sensor that detects a crop state characteristic corresponding to the geographic location;

a predictive model generator that generates a predictive crop state model that models a relationship between the first characteristic values and the crop state characteristic based on a vegetative index value in the prior vegetative index map at the geographic location and the crop state characteristic sensed by the in-situ sensor at the geographic location; and a predictive map generator that generates a functional predictive crop state map of the field that maps predictive crop state values to the different locations in the field based on the vegetative index values in the prior vegetative index map and based on the predictive crop state model.

Example 20 is the agricultural work machine of any or all previous examples, wherein the in-situ sensor comprises an optical sensor and wherein the geographic position sensor detects the geographic location a given time after the in-situ sensor detects the crop state characteristic corresponding to the geographic location, a length of the given time being based at least in part on a machine speed and a field of view of the optical sensor.

Although the subject matter has been described in language specific to structural features or methodological acts, it is to be understood that the subject matter defined in the appended claims is not necessarily limited to the specific features or acts described above. Rather, the specific features and acts described above are disclosed as example forms of the claims

What is claimed is:

1. An agricultural work machine comprising:
   a communication system that receives an information map that includes values of a first agricultural characteristic corresponding to different geographic locations in a field;
   a geographic position sensor that detects a geographic location of the agricultural work machine;
   an in-situ sensor that detects a crop state as a second agricultural characteristic corresponding to the geographic location;
   a predictive model generator that generates a predictive agricultural model that models a relationship between the first agricultural characteristic and the second agricultural characteristic based on a value of the first agricultural characteristic in the information map at the geographic location and a value of the second agricultural characteristic sensed by the in-situ sensor at the geographic location; and
   a predictive map generator that generates a functional predictive agricultural map of the field that maps predictive values of the second agricultural characteristic to the different geographic locations in the field based on the values of the first agricultural characteristic in the information map and based on the predictive agricultural model.

2. The agricultural work machine of claim 1, wherein the predictive map generator configures the functional predictive agricultural map for consumption by a control system that generates control signals to control a controllable subsystem on the agricultural work machine based on the functional predictive agricultural map.

3. The agricultural work machine of claim 1, wherein the in-situ sensor generates sensor data indicative of the crop state and wherein the in-situ sensor comprises;
a processing system configured to analyze the sensor data and determine at least one of an orientation or a magnitude of the crop state.

4. The agricultural machine of claim 1, wherein the information map comprises a prior vegetative index map that maps, as the first agricultural characteristic, vegetative index values to the different geographic locations in the field.

5. The agricultural work machine of claim 4, wherein the predictive model generator is configured to identify the relationship between the crop state detected at the geographic location and a vegetative, index of the vegetative index values in the prior vegetative index map at the geographic location, the predictive agricultural model being configured to receive an input vegetative index value as a model input and generate a predicted crop state value as a model output based on the identified relationship.

6. The agricultural work machine of claim 1, wherein the information map comprises a seeding characteristic map that maps, as the first agricultural characteristic, seeding characteristic values to the different geographic locations in the field.

7. The agricultural work machine of claim 1, wherein the predictive model generator is configured to identify the relationship between the crop state detected at the geographic location and a seeding characteristic in the seeding characteristic map at the geographic location, the predictive agricultural model being configured to receive an input seeding characteristic value as a model input and generate a predicted crop state value as a model output based on the identified relationship.

8. The agricultural work machine of claim 7, wherein the seeding characteristic comprises genetic stalk or stem strength.

9. The agricultural work machine of claim 7, wherein the seeding characteristic comprises genetic susceptibility to lodging.

10. The agricultural work machine of claim 1, wherein the information map comprises a predictive map that maps, as the first agricultural characteristic, predictive yield or predictive biomass values to the different geographic locations in the field.

11. The agricultural work machine of claim 10, wherein the predictive model generator is configured to identify the relationship between the crop state detected at the geographic location and the predictive yield or the predictive biomass in the predictive map at the geographic location, the predictive agricultural model being configured to receive an input yield or biomass value as a model input and generate a predicted crop state value as a model output based on the identified relationship.

12. A computer implemented method of generating a functional predictive agricultural map, the computer implemented method comprising:

receiving an information map at an agricultural work machine that indicates values of a first agricultural characteristic corresponding to different geographic locations in a field,
detecting a geographic location of the agricultural work machine;
detecting, with an in-situ sensor, a crop state as a second agricultural characteristic corresponding to the geographic location;
generating a predictive agricultural model that models a relationship between the first agricultural characteristic and the second agricultural characteristic; and
controlling a predictive map generator to generate the functional predictive agricultural map of the field that maps predictive values of the second agricultural characteristic to the different locations in the field based on the values of the first agricultural characteristic in the information map and the predictive agricultural model.

13. The computer implemented method of claim 12, and further comprising:
configuring the functional predictive agricultural map for a control system that generates control signals to control a controllable subsystem on the agricultural work machine based on the functional predictive agricultural map.

14. The computer implemented method of claim 12, wherein receiving the information map comprises receiving a prior vegetative index map that maps, as the first agricultural characteristic, vegetative index values to the different geographic locations in the field.

15. The computer implemented method of claim 14, wherein generating the predictive agricultural model comprises:
identifying the relationship between the vegetative index values and the crop state based on the crop state detected at the geographic location and a vegetative index value of the vegetative index values in the prior vegetative index map at the geographic location; and
controlling a predictive model generator to generate the predictive agricultural model that receives an input vegetative index value as a model input and generates a predicted crop state value as a model output based on the identified relationship.

16. The computer implemented method of claim 12, wherein receiving the information map comprises receiving a seeding characteristic map that maps, as the first agricultural characteristic, seeding characteristic values to the different geographic locations in the field.

17. The computer implemented Method of claim 16, wherein generating the predictive agricultural model comprises:
identifying the relationship between the seeding characteristic values and the crop state based on the crop state detected at the geographic location and the seeding characteristic values in the seeding characteristic map at the geographic location; and
controlling a predictive model generator to generate the predictive agricultural model that receives an input seeding characteristic value as a model input and generates a predicted crop state value as a model output based on the identified relationship.

18. The computer implemented method of claim 17, wherein the seeding characteristic values comprise seed planting density values.

19. An agricultural work machine comprising:
a communication system that receives a prior vegetative index map that indicates vegetative index values corresponding to different geographic locations in a field;
a geographic position sensor that detects a geographic location of the agricultural work machine;
an in-situ sensor that detects a crop stale characteristic corresponding to the geographic location;
a predictive model generator that generates a predictive crop state model that models a relationship between the first characteristic values and the crop state characteristic based on a vegetative index value in the prior vegetative index map at the geographic location and the crop state characteristic sensed by the in-situ sensor the geographic location; and
a predictive map generator that generates a functional predictive crop state map of the field that maps predictive crop state values to the different locations in the field based on the vegetative index values its the prior vegetative index map and based on the predictive crop state model.

20. The agricultural work machine of claim 19, wherein the in-situ sensor comprises an optical sensor and wherein the geographic position sensor detects the geographic location a given time after the in-situ sensor detects the crop state characteristic corresponding to the geographic location, a length of the given time being based at least in part on a machine speed and a field of view of the optical sensor.

* * * * *